US012624069B2

(12) United States Patent  
Samish et al.

(10) Patent No.: US 12,624,069 B2  
(45) Date of Patent: May 12, 2026

(54) FLAVOR MODIFYING PROTEINS AND FOOD PRODUCTS COMPRISING THE SAME

(71) Applicant: AMAI PROTEINS LTD, Rehovot (IL)

(72) Inventors: Ilan Samish, Rehovot (IL); Itamar Kass, Rehovot (IL); Dalit Hecht, Rehovot (IL); Shmuel Marko, Rehovot (IL); Inbar Zuker, Rehovot (IL)

(73) Assignee: AMAI PROTEINS LTD, Rehovot (IL)

( * ) Notice: Subject to any disclaimer, the term of this patent is extended or adjusted under 35 U.S.C. 154(b) by 371 days.

(21) Appl. No.: 18/268,921

(22) PCT Filed: Dec. 21, 2021

(86) PCT No.: PCT/IB2021/062109  
§ 371 (c)(1),  
(2) Date: Jun. 21, 2023

(87) PCT Pub. No.: WO2022/137121  
PCT Pub. Date: Jun. 30, 2022

(65) Prior Publication Data  
US 2024/0076326 A1     Mar. 7, 2024

Related U.S. Application Data

(60) Provisional application No. 63/223,608, filed on Jul. 20, 2021, provisional application No. 63/174,550, filed on Apr. 14, 2021, provisional application No. 63/128,207, filed on Dec. 21, 2020.

(51) Int. Cl.  
| C07K 14/43 | (2006.01) |
| A23L 2/60 | (2006.01) |
| A23L 2/66 | (2006.01) |
| A23L 27/30 | (2016.01) |

(52) U.S. Cl.  
CPC ............... *C07K 14/43* (2013.01); *A23L 2/60* (2013.01); *A23L 2/66* (2013.01); *A23L 27/31* (2016.08)

(58) Field of Classification Search  
CPC ........... C07K 14/43; A23L 27/31; A23L 2/60; A23L 2/66  
See application file for complete search history.

(56) References Cited

U.S. PATENT DOCUMENTS

| 4,999,207 A | * | 3/1991 | Buckholz, Jr. | ........ C11B 9/0076 |
| | | | | 426/536 |
| 5,264,558 A | | 11/1993 | Kim et al. | |
| 6,001,410 A | * | 12/1999 | Bolen | ........................ C12C 5/02 |
| | | | | 426/534 |

FOREIGN PATENT DOCUMENTS

| CN | 109627307 A | 4/2019 |
| GB | 2 123 672 A | 2/1984 |
| KR | 20120052542 A | 5/2012 |
| RU | 2013115913 A | 10/2014 |
| WO | 1984/002450 A1 | 7/1984 |
| WO | 2019/215730 A1 | 11/2019 |

OTHER PUBLICATIONS

Collins, J., "Cheers to the Health Benefits of Beer!", 2020, Dr. Jim Collins, https://www.drjimcollins.com/cheers-to-the-health-benefits-of-beer/ (Year: 2020).*

Suez et al., "Artificial sweeteners induce glucose intolerance by altering the gut microbiota", Nature, 2014, vol. 514, pp. 181-186.

Johnson et al., "Low-Calorie Sweetened Beverages and Cardiometabolic Health", Circulation, 2018, vol. 138, No. 9, e126-e140.

GenBank Entry No. P02881, 2023.

GenBank Entry No. P02882, 2023.

International Search Report and Written Opinion issued in PCT/IB2021/062109 dated Apr. 11, 2022.

Zhao et al., "Structure basis of the improved sweetness and thermostability of a unique double-sites single-chain sweet-tasting protein monellin (MNEI)" mutant, Biochimie, 2018, vol. 154, pp. 156-163.

Leone et al., "Sweeter and stronger: enhancing sweetness and stability of the single chain monellin MNEI through molecular design", Scientific Reports, 2016, vol. 6, 34045, 10 pages.

Zheng et al., "Expression, purification and characterization of a novel double-sites mutant of the single-chain sweet-tasting protein monellin (MNEI) with both improved sweetness and stability", Protein Expression and Purification, 2018, vol. 143, pp. 52-56.

Yang et al., "The Flexible Loop is a New Sweetness Determinant Site of the Sweet-Tasting Protein: Characterization of Novel Sweeter Mutants of the Single-Chain Monellin (MNEI)", Chemical Senses, 2019, vol. 44, No. 8, pp. 607-614.

Esposito et al., "The Importance of Electrostatic Potential in the Interaction of Sweet Proteins with the Sweet Taste Receptor", Journal of Molecular Biology, 2006, vol. 360, No. 2, pp. 448-456.

Cal et al., "Expression of a high sweetness and heat-resistant mutant of sweet-tasting protein, monellin, in Pichia pastoris with a consitutive GAPDH promoter and modified N-terminus", Biotechnol Lett, 2016, vol. 38, pp. 1941-1946.

Weiffert et al., "Protein stabilization with retained function of monellin using a split GFP system", Scientific Reports, 2018, vol. 8, 12763, 18 pages.

Delfi et al., "A Super Stable Mutant of the Plant Protein Monellin Endowed with Enhanced Sweetness", Life, 2021, vol. 11, No. 236, 13 pages.

Song et al., "Design and development of a high temperature stable sweet protein base on monellin", Process Biochemistry, 2020, vol. 89, pp. 29-36.

Hobbs et al., "Monellin (MNEI) at 1.15 A resolution", Acta Cryst., 2007, F63, pp. 162-167.

(Continued)

*Primary Examiner* — Nikki H. Dees  
*Assistant Examiner* — Kelly P Kershaw  
(74) *Attorney, Agent, or Firm* — The Roy Gross Law Firm, LLC; Roy D. Gross

(57) ABSTRACT

The present invention relates to a modified MNEI protein comprising an amino acid sequence that has two or more amino acids deletions, insertions, replacements, or any combination thereof, from a reference MNEI protein, wherein the modified MNEI protein has at least one improved food-related property compared to the reference MNEI protein; and to uses thereof in the food industry.

19 Claims, 33 Drawing Sheets

Specification includes a Sequence Listing.

(56) References Cited

OTHER PUBLICATIONS

Kim et al., "Redesigning a sweet protein: increased stability and renaturability", Protein Engineering, 1989, vol. 2, No. 8, pp. 571-575.

Morris et al., "Purification of Monellin, the Sweet Principle of Dioscoreophyllum Cumminsh", Biochimica et Biophysica Acta, 1972, vol. 261, No. 1, pp. 114-122.

Weihrauch et al., "Künstliche Süßstoffe—Haben sie ein kanzerogenes Potential?", Medizinische Klinik, 2001, No. 96, pp. 670-675 (with English Abstract and Machine Translation).

Regan, "Protein redesign", Current Opinion in Structrual Biology, 1999, vol. 9, No. 4, pp. 494-499.

Pakula, A. A., & Sauer, R. T. (1989). Genetic analysis of protein stability and function. Annual review of genetics, 23, 289-310. doi: 10.1146/annurev.ge.23.120189.001445. PMID: 2694933.

Tokuriki, N., & Tawfik, D. S. (2009). Stability effects of mutations and protein evolvability. Current opinion in structural biology, 19(5), 596-604. doi: 10.1016/j.sbi.2009.08.003. Epub Sep. 16, 2009. PMID: 19765975.

Keskin, O., Tsai, C. J., Wolfson, H., & Nussinov, R. (2004). A new, structurally nonredundant, diverse data set of protein-protein interfaces and its implications. Protein Science, 13(4), 1043-1055. doi: 10.1110/ps.03484604. PMID: 15044734; PMCID: PMC2280042.

Esposito, V., Gallucci, R., Picone, D., Saviano, G., Tancredi, T., & Temussi, P. A. (2006). The importance of electrostatic potential in the interaction of sweet proteins with the sweet taste receptor. Journal of molecular biology, 360(2), 448-456. doi: 10.1016/j.jmb.2006.05.020. Epub May 23, 2006. PMID: 16764888.

Singer M. et al. (1998) Genes and genomes: A changing Perspective. University Science Books (Mill Valley, California) pp. 63-64.

* cited by examiner

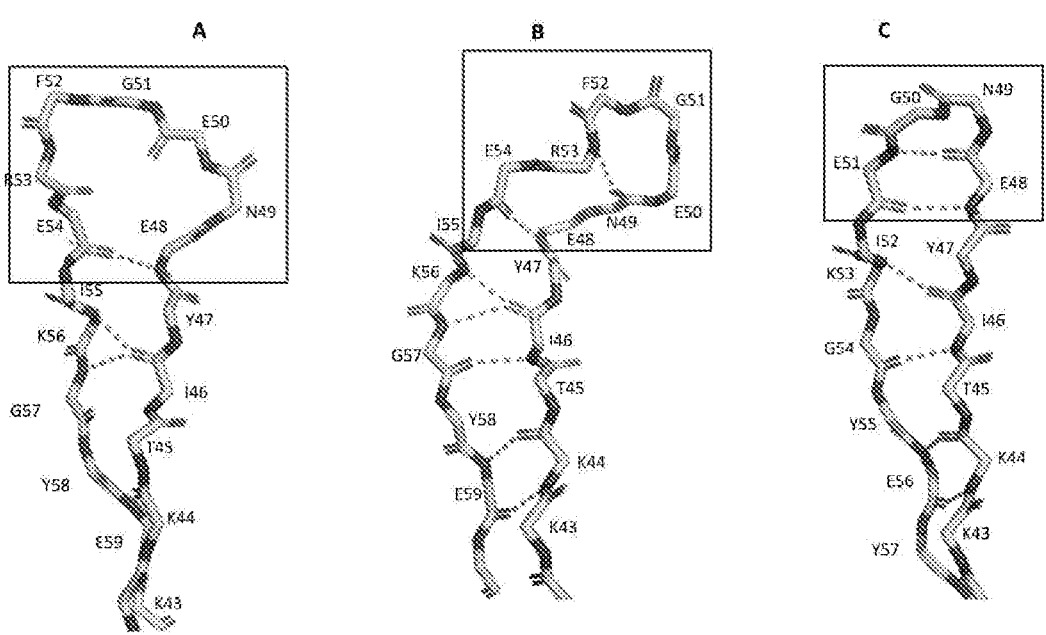
FIG. 32
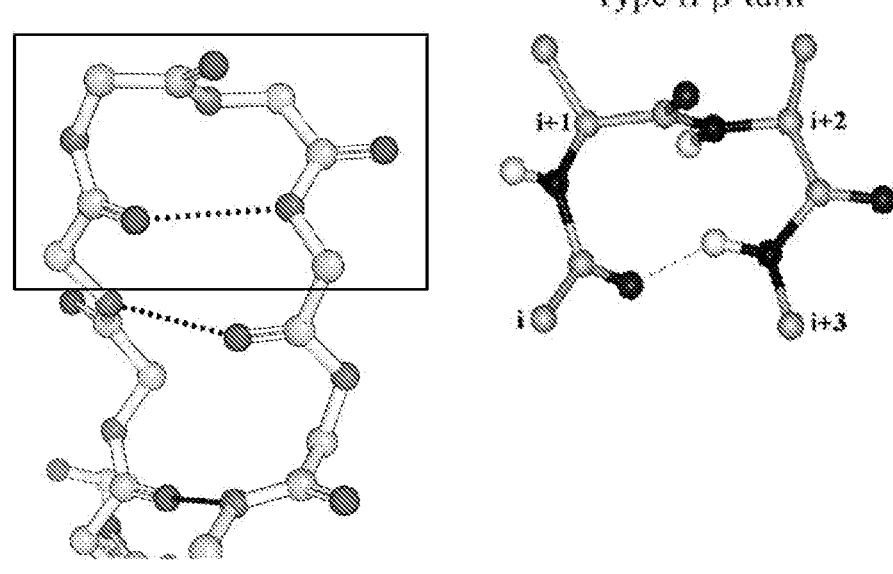
FIG. 33A
FIG. 33B

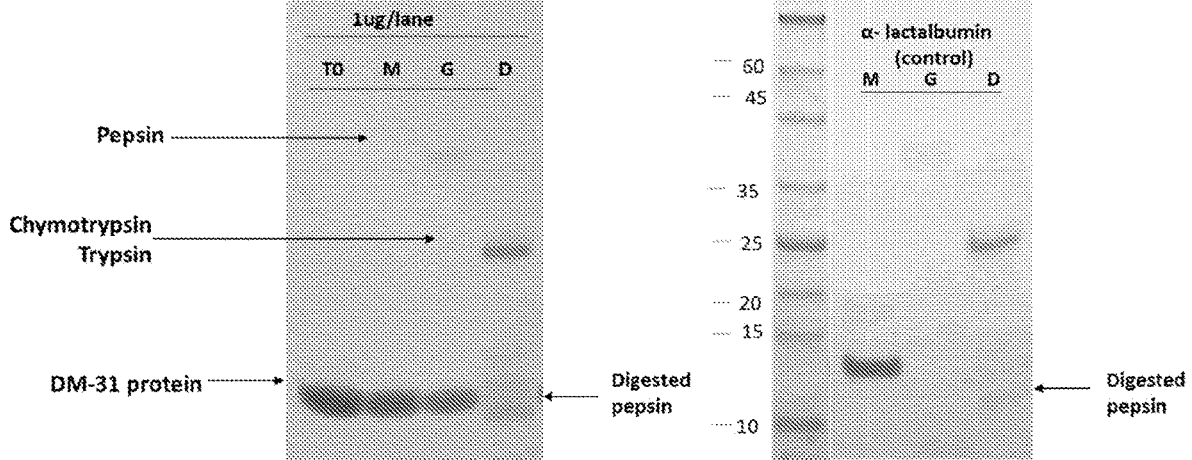
FIG. 34A                    FIG. 34B

SEQUENCE LISTING

```
<160> NUMBER OF SEQ ID NOS: 52

<210> SEQ ID NO 1
<211> LENGTH: 96
<212> TYPE: PRT
<213> ORGANISM: Artificial Sequence
<220> FEATURE:
<223> OTHER INFORMATION: Synthetic sequence

<400> SEQUENCE: 1

Gly Asn Trp Glu Ile Ile Asp Ile Gly Pro Phe Thr Gln Asn Leu Gly
1               5                   10                  15

Lys Phe Ala Val Asp Glu Val Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Lys Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 2
<211> LENGTH: 96
<212> TYPE: PRT
<213> ORGANISM: Artificial Sequence
<220> FEATURE:
<223> OTHER INFORMATION: Synthetic Sequence

<400> SEQUENCE: 2

Gly Asn Trp Glu Ile Ile Asp Ile Gly Pro Phe Thr Gln Asn Leu Gly
1               5                   10                  15

Lys Phe Ala Val Asp Glu Ala Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 3
<211> LENGTH: 96
<212> TYPE: PRT
<213> ORGANISM: Artificial Sequence
<220> FEATURE:
<223> OTHER INFORMATION: Synthetic

<400> SEQUENCE: 3

Gly Asn Trp Glu Ile Ile Asp Ile Gly Pro Phe Thr Gln Asn Leu Gly
1               5                   10                  15
```

Lys Phe Ala Val Asp Glu Glu Asn Lys Ile Gly Gln Tyr Gly Arg Leu
                20                      25                      30

Thr Phe Asn Lys Val Ile Arg Pro Cys Met Lys Lys Thr Ile Tyr Glu
                35                      40                      45

Asn Glu Gly Phe Arg Glu Ile Lys Gly Tyr Glu Tyr Gln Leu Tyr Val
        50                      55                      60

Lys Ala Ser Asp Lys Ile Phe Arg Ala Asp Ile Ser Glu Asp Tyr Lys
65                      70                      75                      80

Thr Arg Gly Arg Lys Leu Leu Arg Phe Asn Gly Pro Val Pro Pro Pro
                85                      90                      95

<210> SEQ ID NO 4
<211> LENGTH: 96
<212> TYPE: PRT
<213> ORGANISM: Artificial Sequence
<220> FEATURE:
<223> OTHER INFORMATION: Synthetic

<400> SEQUENCE: 4

Gly Asn Trp Glu Ile Ile Asp Ile Gly Pro Phe Thr Gln Asn Leu Gly
1                       5                       10                      15

Lys Phe Ala Val Asp Glu Val Asn Lys Ile Gly Gln Tyr Gly Arg Leu
                20                      25                      30

Thr Phe Asn Thr Val Ile Arg Pro Cys Met Lys Lys Thr Ile Tyr Glu
                35                      40                      45

Asn Glu Gly Phe Arg Glu Ile Lys Gly Tyr Glu Tyr Gln Leu Tyr Val
        50                      55                      60

Lys Ala Ser Asp Lys Ile Phe Arg Ala Asp Ile Ser Glu Asp Tyr Lys
65                      70                      75                      80

Thr Arg Gly Arg Lys Leu Leu Arg Phe Asn Gly Pro Val Pro Pro Pro
                85                      90                      95

<210> SEQ ID NO 5
<211> LENGTH: 96
<212> TYPE: PRT
<213> ORGANISM: Artificial Sequence
<220> FEATURE:
<223> OTHER INFORMATION: Synthetic

<400> SEQUENCE: 5

Gly Asn Trp Glu Ile Ile Asp Ile Gly Pro Phe Thr Gln Asn Leu Gly
1                       5                       10                      15

Lys Phe Ala Val Asp Glu Ala Asn Lys Ile Gly Gln Tyr Gly Arg Leu
                20                      25                      30

Thr Phe Asn Thr Val Ile Arg Pro Cys Met Lys Lys Thr Ile Tyr Glu
                35                      40                      45

Asn Glu Gly Phe Arg Glu Ile Lys Gly Tyr Glu Tyr Gln Leu Tyr Val
        50                      55                      60

Arg Ala Ser Asp Lys Ile Phe Arg Ala Asp Ile Ser Glu Asp Tyr Lys
65                      70                      75                      80

Thr Arg Gly Arg Lys Leu Leu Arg Phe Asn Gly Pro Val Pro Pro Pro
                85                      90                      95

<210> SEQ ID NO 6
<211> LENGTH: 96
<212> TYPE: PRT
<213> ORGANISM: Artificial Sequence
<220> FEATURE:
<223> OTHER INFORMATION: Synthetic -continued

<400> SEQUENCE: 6

```
Gly Asn Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Thr Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Lys Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95
```

<210> SEQ ID NO 7
<211> LENGTH: 96
<212> TYPE: PRT
<213> ORGANISM: Artificial Sequence
<220> FEATURE:
<223> OTHER INFORMATION: Synthetic

<400> SEQUENCE: 7

```
Gly Asn Trp Glu Ile Ile Asp Ile Gly Pro Phe Thr Gln Asn Leu Gly
1               5                   10                  15

Lys Phe Ala Val Asp Glu Ala Asn Lys Ile Gly Gln Tyr Gly Arg Leu
            20                  25                  30

Thr Phe Thr Thr Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95
```

<210> SEQ ID NO 8
<211> LENGTH: 96
<212> TYPE: PRT
<213> ORGANISM: Artificial Sequence
<220> FEATURE:
<223> OTHER INFORMATION: Synthetic

<400> SEQUENCE: 8

```
Gly Asn Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Thr Thr Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95
```

<210> SEQ ID NO 9

-continued

```
<211> LENGTH: 96
<212> TYPE: PRT
<213> ORGANISM: Artificial Sequence
<220> FEATURE:
<223> OTHER INFORMATION: Synthetic

<400> SEQUENCE: 9

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Thr Thr Val Ile Arg Pro Cys Met Lys Lys Thr Ile Tyr Glu
            35                  40                  45

Asn Glu Gly Phe Arg Glu Ile Lys Gly Tyr Glu Tyr Gln Leu Tyr Val
        50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 10
<211> LENGTH: 96
<212> TYPE: PRT
<213> ORGANISM: Artificial Sequence
<220> FEATURE:
<223> OTHER INFORMATION: Synthetic

<400> SEQUENCE: 10

Gly Asn Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Thr Val Ile Arg Pro Cys Met Lys Lys Thr Ile Tyr Glu
            35                  40                  45

Asn Glu Gly Phe Arg Glu Ile Lys Gly Tyr Glu Tyr Gln Leu Tyr Val
        50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 11
<211> LENGTH: 96
<212> TYPE: PRT
<213> ORGANISM: Artificial Sequence
<220> FEATURE:
<223> OTHER INFORMATION: Synthetic

<400> SEQUENCE: 11

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Thr Val Ile Arg Pro Cys Met Lys Lys Thr Ile Tyr Glu
            35                  40                  45

Asn Glu Gly Phe Arg Glu Ile Lys Gly Tyr Glu Tyr Gln Leu Tyr Val
        50                  55                  60

Arg Ala Ser Asp Lys Ile Phe Arg Ala Asp Ile Ser Glu Asp Tyr Lys
65                  70                  75                  80
```

-continued

```
Thr Arg Gly Arg Lys Leu Leu Arg Phe Asn Gly Pro Val Pro Pro Pro
            85                  90                  95

<210> SEQ ID NO 12
<211> LENGTH: 96
<212> TYPE: PRT
<213> ORGANISM: Artificial Sequence
<220> FEATURE:
<223> OTHER INFORMATION: Synthetic

<400> SEQUENCE: 12

Gly Asn Trp Glu Ile Ile Asp Ile Gly Pro Phe Thr Gln Asn Leu Gly
1               5                   10                  15

Lys Phe Ala Val Asp Glu Ala Asn Lys Ile Gly Gln Tyr Gly Arg Leu
            20                  25                  30

Thr Phe Thr Lys Val Ile Arg Pro Cys Met Lys Lys Thr Ile Tyr Glu
            35                  40                  45

Asn Glu Gly Phe Arg Glu Ile Lys Gly Tyr Glu Tyr Gln Leu Tyr Val
            50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
            85                  90                  95

<210> SEQ ID NO 13
<211> LENGTH: 96
<212> TYPE: PRT
<213> ORGANISM: Artificial Sequence
<220> FEATURE:
<223> OTHER INFORMATION: Synthetic

<400> SEQUENCE: 13

Gly Asn Trp Glu Ile Ile Asp Ile Gly Pro Phe Thr Gln Asn Leu Gly
1               5                   10                  15

Lys Phe Ala Val Asp Glu Ile Asn Lys Ile Gly Gln Tyr Gly Arg Leu
            20                  25                  30

Thr Phe Asn Lys Val Ile Arg Pro Cys Met Lys Lys Thr Ile Tyr Glu
            35                  40                  45

Asn Glu Gly Phe Arg Glu Ile Lys Gly Tyr Glu Tyr Gln Leu Tyr Val
            50                  55                  60

Arg Ala Ser Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
            85                  90                  95

<210> SEQ ID NO 14
<211> LENGTH: 96
<212> TYPE: PRT
<213> ORGANISM: Artificial Sequence
<220> FEATURE:
<223> OTHER INFORMATION: Synthetic

<400> SEQUENCE: 14

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Cys Met Lys Lys Thr Ile Tyr Glu
            35                  40                  45
```

```
Asn Glu Gly Phe Arg Glu Ile Lys Gly Tyr Glu Tyr Gln Leu Tyr Val
    50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 15
<211> LENGTH: 96
<212> TYPE: PRT
<213> ORGANISM: Artificial Sequence
<220> FEATURE:
<223> OTHER INFORMATION: Synthetic

<400> SEQUENCE: 15

Gly Asn Trp Glu Ile Ile Asp Ile Gly Pro Phe Thr Gln Asn Leu Gly
1               5                   10                  15

Lys Phe Ala Val Asp Glu Val Asn Lys Ile Gly Gln Tyr Gly Arg Leu
                20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Arg Ala Ser Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 16
<211> LENGTH: 93
<212> TYPE: PRT
<213> ORGANISM: Artificial Sequence
<220> FEATURE:
<223> OTHER INFORMATION: Synthetic

<400> SEQUENCE: 16

Gly Asn Trp Glu Ile Ile Asp Ile Gly Pro Phe Thr Gln Asn Leu Gly
1               5                   10                  15

Lys Phe Ala Val Asp Glu Ala Asn Lys Ile Gly Gln Tyr Gly Arg Leu
                20                  25                  30

Thr Phe Asn Lys Val Ile Arg Pro Cys Met Lys Lys Thr Ile Tyr Glu
        35                  40                  45

Asn Gly Glu Ile Lys Gly Tyr Glu Tyr Gln Leu Tyr Val Arg Ala Ser
    50                  55                  60

Asp Lys Leu Phe Arg Ala Asp Ile Ser Glu Asp Tyr Lys Thr Arg Gly
65                  70                  75                  80

Arg Lys Leu Leu Arg Phe Asn Gly Pro Val Pro Pro Pro
                85                  90

<210> SEQ ID NO 17
<211> LENGTH: 93
<212> TYPE: PRT
<213> ORGANISM: Artificial Sequence
<220> FEATURE:
<223> OTHER INFORMATION: Synthetic

<400> SEQUENCE: 17

Gly Glu Trp Glu Ile Ile Asp Ile Gly Pro Phe Thr Gln Asn Leu Gly
1               5                   10                  15
```

-continued

```
Lys Phe Ala Val Asp Glu Glu Asn Lys Ile Gly Gln Tyr Gly Arg Leu
        20                  25                  30

Thr Phe Asn Lys Val Ile Arg Pro Cys Met Lys Lys Thr Ile Tyr Glu
        35                  40                  45

Asn Gly Glu Ile Lys Gly Tyr Glu Tyr Gln Leu Tyr Val Tyr Ala Ser
    50                  55                  60

Asp Lys Leu Phe Arg Ala Asp Ile Ser Glu Asp Tyr Lys Thr Arg Gly
65                  70                  75                  80

Arg Lys Leu Leu Arg Phe Asn Gly Pro Val Pro Pro Pro
                85                  90
```

<210> SEQ ID NO 18
<211> LENGTH: 96
<212> TYPE: PRT
<213> ORGANISM: Artificial Sequence
<220> FEATURE:
<223> OTHER INFORMATION: Synthetic

<400> SEQUENCE: 18

```
Gly Asn Trp Glu Ile Ile Asp Ile Gly Pro Phe Thr Gln Asn Leu Gly
1               5                   10                  15

Lys Phe Ala Val Asp Glu Ile Asn Lys Ile Gly Gln Tyr Gly Arg Leu
        20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Arg Ala Ser Asp Lys Ile Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95
```

<210> SEQ ID NO 19
<211> LENGTH: 93
<212> TYPE: PRT
<213> ORGANISM: Artificial Sequence
<220> FEATURE:
<223> OTHER INFORMATION: Synthetic

<400> SEQUENCE: 19

```
Gly Asn Trp Glu Ile Ile Asp Ile Gly Pro Phe Thr Gln Asn Leu Gly
1               5                   10                  15

Lys Phe Ala Val Asp Glu Ala Asn Lys Ile Gly Gln Tyr Gly Arg Leu
        20                  25                  30

Thr Phe Asn Lys Val Ile Arg Pro Cys Met Lys Lys Thr Ile Tyr Glu
        35                  40                  45

Asn Gly Glu Ile Lys Gly Tyr Glu Tyr Gln Leu Tyr Val Arg Ala Ser
    50                  55                  60

Asp Lys Ile Phe Arg Ala Asp Ile Ser Glu Asp Tyr Lys Thr Arg Gly
65                  70                  75                  80

Arg Lys Leu Leu Arg Phe Asn Gly Pro Val Pro Pro Pro
                85                  90
```

<210> SEQ ID NO 20
<211> LENGTH: 93
<212> TYPE: PRT
<213> ORGANISM: Artificial Sequence
<220> FEATURE:
<223> OTHER INFORMATION: Synthetic -continued

```
<400> SEQUENCE: 20

Gly Asn Trp Glu Ile Ile Asp Ile Gly Pro Phe Thr Gln Asn Leu Gly
1               5                   10                  15

Lys Phe Ala Val Asp Glu Val Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Gly Glu Ile Lys Gly Tyr Glu Tyr Gln Leu Tyr Val Lys Ala Ser
    50                  55                  60

Asp Lys Ile Phe Arg Ala Asp Ile Ser Glu Asp Tyr Lys Thr Arg Gly
65                  70                  75                  80

Arg Lys Leu Leu Arg Phe Asn Gly Pro Val Pro Pro Pro
                85                  90

<210> SEQ ID NO 21
<211> LENGTH: 93
<212> TYPE: PRT
<213> ORGANISM: Artificial Sequence
<220> FEATURE:
<223> OTHER INFORMATION: Synthetic

<400> SEQUENCE: 21

Gly Asn Trp Glu Ile Ile Asp Ile Gly Pro Phe Thr Gln Asn Leu Gly
1               5                   10                  15

Lys Phe Ala Val Asp Glu Val Asn Lys Ile Gly Gln Tyr Gly Arg Leu
            20                  25                  30

Thr Phe Asn Thr Val Ile Arg Pro Cys Met Lys Lys Thr Ile Tyr Glu
        35                  40                  45

Asn Gly Glu Ile Lys Gly Tyr Glu Tyr Gln Leu Tyr Val Lys Ala Ser
    50                  55                  60

Asp Lys Ile Phe Arg Ala Asp Ile Ser Glu Asp Tyr Lys Thr Arg Gly
65                  70                  75                  80

Arg Lys Leu Leu Arg Phe Asn Gly Pro Val Pro Pro
                85                  90

<210> SEQ ID NO 22
<211> LENGTH: 96
<212> TYPE: PRT
<213> ORGANISM: Artificial Sequence
<220> FEATURE:
<223> OTHER INFORMATION: Synthetic

<400> SEQUENCE: 22

Gly Asn Trp Glu Ile Ile Asp Thr Gly Pro Phe Thr Gln Lys Leu Gly
1               5                   10                  15

Lys Phe Ala Val Asp Glu Ala Asn Lys Ile Gly Lys Tyr Gly Thr Leu
            20                  25                  30

Thr Phe Thr Lys Val Ile Arg Pro Thr Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Lys Ala Asn Asp Lys Leu Phe Arg Ala Asp Ile Ser Glu Asp Tyr Lys
65                  70                  75                  80

Thr Arg Gly Leu Lys Leu Leu Arg Phe Asn Gly Pro Val Pro Pro Pro
                85                  90                  95

<210> SEQ ID NO 23
<211> LENGTH: 96
```

-continued

```
<212> TYPE: PRT
<213> ORGANISM: Artificial Sequence
<220> FEATURE:
<223> OTHER INFORMATION: Synthetic

<400> SEQUENCE: 23

Gly Asn Trp Glu Ile Ile Asp Ile Gly Pro Phe Thr Gln Asn Leu Gly
1               5                   10                  15

Lys Phe Ala Val Asp Glu Val Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
        50                  55                  60

Lys Ala Ser Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 24
<211> LENGTH: 96
<212> TYPE: PRT
<213> ORGANISM: Artificial Sequence
<220> FEATURE:
<223> OTHER INFORMATION: Synthetic

<400> SEQUENCE: 24

Gly Asn Trp Glu Ile Ile Asp Ile Gly Pro Phe Thr Gln Asn Leu Gly
1               5                   10                  15

Lys Phe Ala Val Asp Glu Ala Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
        50                  55                  60

Arg Ala Ser Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 25
<211> LENGTH: 96
<212> TYPE: PRT
<213> ORGANISM: Artificial Sequence
<220> FEATURE:
<223> OTHER INFORMATION: Synthetic

<400> SEQUENCE: 25

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Lys Tyr Gly Thr Leu
            20                  25                  30

Thr Phe Thr Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
        50                  55                  60

Tyr Ala Asn Asp Lys Leu Phe Arg Ala Asp Ile Ser Glu Asp Tyr Lys
65                  70                  75                  80
```

```
Thr Arg Gly Arg Lys Leu Leu Arg Phe Asn Gly Pro Val Pro Pro Pro
                85                  90                  95

<210> SEQ ID NO 26
<211> LENGTH: 96
<212> TYPE: PRT
<213> ORGANISM: Artificial Sequence
<220> FEATURE:
<223> OTHER INFORMATION: Synthetic

<400> SEQUENCE: 26

Gly Glu Trp Glu Ile Ile Asp Thr Gly Pro Phe Thr Gln Lys Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Thr Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Tyr Ala Ser Asp Lys Leu Phe Arg Ala Asp Ile Ser Glu Asp Tyr Lys
65                  70                  75                  80

Thr Arg Gly Leu Lys Leu Leu Arg Phe Asn Gly Pro Val Pro Pro Pro
                85                  90                  95

<210> SEQ ID NO 27
<211> LENGTH: 96
<212> TYPE: PRT
<213> ORGANISM: Artificial Sequence
<220> FEATURE:
<223> OTHER INFORMATION: Synthetic

<400> SEQUENCE: 27

Gly Glu Trp Glu Ile Ile Asp Thr Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Thr Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Tyr Ala Ser Asp Lys Leu Phe Arg Ala Asp Ile Ser Glu Asp Tyr Lys
65                  70                  75                  80

Thr Arg Gly Leu Lys Leu Leu Arg Phe Asn Gly Pro Val Pro Pro Pro
                85                  90                  95

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
aagcgataaa atctttcgtg cagatattag                                        30

<210> SEQ ID NO 29
<211> LENGTH: 23
<212> TYPE: DNA
<213> ORGANISM: Artificial Sequence
<220> FEATURE:
<223> OTHER INFORMATION: Synthetic
```

-continued

```
<400> SEQUENCE: 29
gctttcacat acagctgata ttc                                            23

<210> SEQ ID NO 30
<211> LENGTH: 32
<212> TYPE: DNA
<213> ORGANISM: Artificial Sequence
<220> FEATURE:
<223> OTHER INFORMATION: Synthetic

<400> SEQUENCE: 30
aagcgataaa atctttcgtg cagatattag cg                                  32

<210> SEQ ID NO 31
<211> LENGTH: 18
<212> TYPE: DNA
<213> ORGANISM: Artificial Sequence
<220> FEATURE:
<223> OTHER INFORMATION: Synthetic

<400> SEQUENCE: 31
gcgcgcacat acagctga                                                  18

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
agttgacgaa gaaaacaaaa ttgg                                           24

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
gcaaatttac ccaggttc                                                  18

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
acctttaaca ccgttattcg tccgtgcatg                                     30

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
cagacgacca tactggcc                                                  18

<210> SEQ ID NO 36
```

-continued

```
<211> LENGTH: 23
<212> TYPE: DNA
<213> ORGANISM: Artificial Sequence
<220> FEATURE:
<223> OTHER INFORMATION: Synthetic

<400> SEQUENCE: 36
ctgaccttta ccaccgttat tcg                                          23

<210> SEQ ID NO 37
<211> LENGTH: 18
<212> TYPE: DNA
<213> ORGANISM: Artificial Sequence
<220> FEATURE:
<223> OTHER INFORMATION: Synthetic

<400> SEQUENCE: 37
acgaccatac tggccaat                                                18

<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
taccatgggc gaatgggaga tta                                          23

<210> SEQ ID NO 39
<211> LENGTH: 33
<212> TYPE: DNA
<213> ORGANISM: Artificial Sequence
<220> FEATURE:
<223> OTHER INFORMATION: Synthetic

<400> SEQUENCE: 39
tatctccttc ttaaagttaa acaaaattat ttc                               33

<210> SEQ ID NO 40
<211> LENGTH: 31
<212> TYPE: DNA
<213> ORGANISM: Artificial Sequence
<220> FEATURE:
<223> OTHER INFORMATION: Synthetic

<400> SEQUENCE: 40
gacctttacc aaagttattc gtccgtgcat g                                 31

<210> SEQ ID NO 41
<211> LENGTH: 18
<212> TYPE: DNA
<213> ORGANISM: Artificial Sequence
<220> FEATURE:
<223> OTHER INFORMATION: Synthetic

<400> SEQUENCE: 41
agacgaccat actggcca                                                18

<210> SEQ ID NO 42
<211> LENGTH: 26
<212> TYPE: DNA
<213> ORGANISM: Artificial Sequence
<220> FEATURE:
<223> OTHER INFORMATION: Synthetic
```

-continued

<400> SEQUENCE: 42
agttgacgaa attaacaaaa ttggcc                                                                    26

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
gcaaatttac ccaggttc                                                                             18

<210> SEQ ID NO 44
<211> LENGTH: 26
<212> TYPE: DNA
<213> ORGANISM: Artificial Sequence
<220> FEATURE:
<223> OTHER INFORMATION: Synthetic

<400> SEQUENCE: 44
gctgtatgtg cgcgcaagcg ataaac                                                                    26

<210> SEQ ID NO 45
<211> LENGTH: 96
<212> TYPE: PRT
<213> ORGANISM: Artificial Sequence
<220> FEATURE:
<223> OTHER INFORMATION: Synthetic

<400> SEQUENCE: 45

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Tyr Ala Ser Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 46
<211> LENGTH: 23
<212> TYPE: DNA
<213> ORGANISM: Artificial Sequence
<220> FEATURE:
<223> OTHER INFORMATION: Synthetic

<400> SEQUENCE: 46
tgatattcat agcctttaat ctc                                                                       23

<210> SEQ ID NO 47
<211> LENGTH: 22
<212> TYPE: DNA
<213> ORGANISM: Artificial Sequence
<220> FEATURE:
<223> OTHER INFORMATION: Synthetic -continued

```
<400> SEQUENCE: 47
gttgacgaag tgaacaaaat tg                                                    22

<210> SEQ ID NO 48
<211> LENGTH: 19
<212> TYPE: DNA
<213> ORGANISM: Artificial Sequence
<220> FEATURE:
<223> OTHER INFORMATION: Synthetic

<400> SEQUENCE: 48
tgcaaattta cccaggttc                                                        19

<210> SEQ ID NO 49
<211> LENGTH: 18
<212> TYPE: DNA
<213> ORGANISM: Artificial Sequence
<220> FEATURE:
<223> OTHER INFORMATION: Synthetic

<400> SEQUENCE: 49
gcgagattaa aggctatg                                                         18

<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
cattttcata gatggttttt ttc                                                   23

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
caagcgataa aatctttcgt gcag                                                  24

<210> SEQ ID NO 52
<211> LENGTH: 17
<212> TYPE: DNA
<213> ORGANISM: Artificial Sequence
<220> FEATURE:
<223> OTHER INFORMATION: Synthetic

<400> SEQUENCE: 52
cgcgcacata cagctga                                                          17
```

FLAVOR MODIFYING PROTEINS AND FOOD PRODUCTS COMPRISING THE SAME

CROSS-REFERENCE TO RELATED APPLICATIONS

This application is a U.S. National Phase of International Patent Application No. PCT/IB2021/062109, filed on Dec. 21, 2021, which claims priority to U.S. Provisional Application No. 63/223,608, filed on Jul. 20, 2021, 63/174,550, filed on Apr. 14, 2021, and 63/128,207, filed on Dec. 21, 2020. The entire contents of each of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created On Dec. 21, 2021, is named 264737.000003_SL.txt and is 30,354 bytes in size.

FIELD OF THE INVENTION

The present invention relates to flavor modifying proteins and to formulations and food products comprising the same. The flavor modifying proteins may be provided in various formulations for animal feed and human consumption.

BACKGROUND OF THE INVENTION

Sugar alternatives are receiving increased attention due to increased disease awareness as a result of sugar overconsumption as the underlying cause of the metabolic syndrome. Known manifestations of the metabolic syndrome are diabetes, obesity, tooth decay, several types of cancers and many additional ailments. The food and beverage industry are being challenged to produce healthier, reduced-calorie foods to meet the demands of consumers and public policy officials. As part of this numerous countries are applying sugar taxes and warning labeling.

The food industry faces the challenge of making more natural 'better for you' foods and beverages that fit consumer trends, while providing the taste necessary for successful products. Low-calorie sweetener ingredients have expanded options for consumers looking to reduce calories and sugar levels in their diets, but these ingredients are limited by taste, stability, and versatility.

There is an urgent global need for a healthy sweetening alternative for food and beverage products with optimal sensory properties and good stability to successfully compete in the global market. Artificial high-intensity sweeteners (HIS), such as Saccharin, Aspartame, Cyclamate, and Acesulfame K, Sucralose, Neotame, and Advantame are used worldwide as low-calorie sweeteners for patients suffering from sugar-related illnesses such as diabetes, hyperlipidemia, metabolic syndrome, etc. HIS have various side effects, e.g., these zero-calorie sweeteners have been reported to interact with the microbiome and cause obesity and a pre-diabetic condition (Suez et al., 2014, Nature volume 514, pages 181-186), even if to a lesser extent than sugar. The American Heart Association published an advisory against HIS, claiming that there is "a dearth of evidence for adverse health effects" (Johnson et al., 2018, Circulation, Vol. 138, No. 9). In this advisory, all HIS, natural (steviol glycosides and monk fruit) and artificial, were put under the same scrutiny. Additionally, low-intensity sweeteners (LIS), namely rare sugars and polyols (e.g., xylitol, mannitol, allulose, etc.), are associated with high costs and are not fully digested by the human body, limiting their use in order to avoid bloating, diarrhea, and other adverse gastrointestinal effects. Thus, currently, there is no good sugar substitute that enables significant (>30%) sugar reduction and fully addresses taste, health, cost, and product fitness.

Sweet proteins (SP) have the potential to replace HIS by providing natural, palatable, low-calorie sweeteners with no glycemic index since proteins do not induce an insulin response, unlike sucrose (Weihrauch 2001 and Cohen 2001). SPs are found in exotic fruits and are 700-3,000 times sweeter than sugar. These healthy sweeteners bind to sweet receptors like sugar but are digested as proteins. They are expected to have a zero glycemic index, ~0 calories, and no adverse effects on our health or microbiome. Thaumatin is currently the only globally approved sweet protein in the market. Due to high price, limited supply, and suboptimal sensory profile, SPs are not generally used as a significant (>30%) sugar-reduction solution. Other than thaumatin, SPs have not entered the mass food market due to expense, limited supply, low stability, short shelf life, especially in a fatty environment, and lingering taste. Therefore, there is a need to develop compositions and formulations to overcome one or more of the aforementioned problems.

GB2123672 describes sweet proteins, such as Thaumatin and Monellin, and an incorporated weakly acidic polysaccharide gum, optionally together with a food acid or bulking agent, in various beverages, mouthwashes, or as a pharmaceutical base.

WO8402450 describes the application of Thaumatin or Monellin to the surface of a chewing gum composition comprising gum base, sweetener, and flavoring.

WO2019215730 discloses modified proteins with improved food-related properties.

SUMMARY OF THE INVENTION

In accordance with some aspects, the present disclosure provides a modified version of a single-chain Monellin (MNEI) protein comprising an amino acid sequence that has two or more amino acids deletions, insertions, replacements, or any combination thereof from an MNEI reference protein, wherein the modified MNEI protein has at least one improved food-related property compared to the reference MNEI protein.

In accordance with some other aspects, the present disclosure provides a food product comprising a modified MNEI protein comprising an amino acid sequence that has two or more amino acids deletions, insertions, replacements, or any combination thereof from an MNEI reference protein, wherein the modified MNEI protein has at least one improved food-related property compared to the reference MNEI protein. In accordance with some embodiments, the modified protein comprises at least three amino acid deletions, insertions, replacements, or any combination thereof from the reference MNEI protein.

According to some embodiments, the two or more amino acid deletions, insertions, replacements, or any combination thereof are located on the reference MNEI protein's surface or in the reference MNEI protein's core. According to some embodiments, the two or more amino acid deletions, insertions, replacements, or any combination thereof, are located within the modified MNEI loop (also termed 'linker region'), and beta-strand edges. According to some embodiments, the two or more amino acid deletions, insertions, replacements, or any combination thereof, are located within the modified MNEI loop and beta-strand edges spanning residues 46-56.

According to some embodiments, said amino acid deletions, substitutions replacements, grafting, or any combinations thereof stabilizing a loop region by at least one of (i) adding at least one hydrogen bond, (ii) extending the beta strands holding the loop region, (iii) decreasing the relative Debye-Waller factors at the loop region, or (iv) any combination thereof. According to some embodiments, said stabilizing is associated with at least one of (i) decreases aggregation, (ii) increases melting temperature (iii) increases shelf-life stability or (iv) any combination thereof.

According to some embodiments, the modified MNEI protein has energy lower than −182 given in Rosetta Energy Unit (REU).

According to some embodiments, the at least one food-related property is at least one of sweetness potency, sweetness kinetics, masking effect, enhancing taste, off-taste or any combination thereof. According to some embodiments, the modified MNEI protein has at least 1.5-fold increased sweetness potency compared to the reference MNEI protein.

According to some embodiments, the modified MNEI protein is characterized by at least one of the following, compared to the reference MNEI protein: (1) increased thermal stability, (2) increased pH stability, (3) increased solubility, (4) decreased binding to hydrophobic regions, (5) high pressure stability, (6) increased shelf-life stability, and any combination thereof.

According to some embodiments, the modified MNEI protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21, or of a fragment or variant thereof.

According to some embodiments, the reference MNEI protein has the sequence set forth in SEQ ID NO:45.

According to some embodiments, the modified MNEI protein or any combination thereof is used in the preparation of a product for oral delivery.

According to some embodiments, the product is a food product, a food supplementary product, or a medicament.

According to some embodiments, the modified MNEI protein or any combination thereof is used as a flavor modifying or a flavor-enhancing agent.

According to some embodiments, the modified MNEI protein is used as a sweetener.

In accordance with some aspects, the present disclosure provides a food product comprising the modified protein of the present invention.

According to some embodiments, the food product comprises at least one food ingredient. According to some embodiments, the food ingredient is at least one of artificial flavor, food additive, food coloring, preservative, or sugar additive. According to some embodiments, the food ingredient is selected from the group consisting of stevia, sucrose, agave nectar, brown rice syrup, date sugar, honey, maple syrup, molasses, monk fruit, sugar alcohols, rare sugars, aspartame, sucralose, acesulfame potassium, saccharin, neotame, advantame, and dietary fibers.

According to some embodiments, said stevia is a rebaudioside or steviol glycoside. According to some embodiments, said rebaudioside is RebM.

According to some embodiments, there is a synergy between RebM and the modified MNEI protein of the present invention.

In accordance with some aspects, the present disclosure provides a sweetening composition comprising the modified MNEI protein of the present invention. According to some embodiments, the present disclosure provides an ingestible composition comprising said sweetening composition. According to some embodiments, the ingestible composition has low glycemic effects and is in the form of liquid or solid foodstuffs.

The present invention, according to some aspects, provides specific food and beverage formulations with improved food or beverage-related properties.

In accordance with some aspects, the present disclosure provides food or beverage formulations comprising one or more modified single-chain Monellin (MNEI) proteins in the range of about 0.2 mg to about 30 mg per 100 gr or 100 ml. According to some embodiments, the range is about 0.4 mg to about 10 mg per 100 gr or 100 ml.

According to some embodiments, said formulation has a pH in the range of about 2 to about 8.5.

According to some embodiments, said modified MNEI protein comprises an amino acid sequence having 40% to 99% identity with a reference MNEI protein comprises the amino acid sequence set forth in SEQ ID NO:45.

According to some embodiments, the modified MNEI comprises an amino acid sequence selected from the group consisting of SEQ ID NOs:1-27 or a fragment or variant thereof.

According to some embodiments, the modified MNEI protein is a digestible protein.

According to some aspects, the present invention provides a food or beverage composition formulated for consumption by a human subject, the composition comprising said formulation.

According to some embodiments, the beverage composition is selected from the group consisting of a carbonated soft drink, a non-carbonated soft drink, a fountain beverage, a frozen ready-to-drink beverage, a coffee beverage, a tea beverage, a dairy beverage, a fruit beverage, a flavored water, an enhanced water, a sport drink, an energy drink, an isotonic drink, low-calorie drink, and an alcoholic beverage.

According to some embodiments, the food compositions are selected from the group consisting of baked goods, cookies, biscuits, baking mixes, cereals, confectioneries, candies, toffees, chewing gum, dairy products, yogurts, flavored yogurts, soy sauce and other soy-based products, nondairy products, salad dressings, ketchup, mayonnaise, vinegar, frozen-desserts, meat products, fish products, bottled and canned foods, tabletop sweeteners, chocolate, fruits, dry fruits, and vegetables.

According to some embodiments, said composition has at least one improved food or beverage-related property compared to a food or beverage composition with the reference MNEI protein.

According to some embodiments, the at least one improved food or beverage related property is selected from the group consisting of improved sweetness profile, shortened sweet taste lingering, improved sweetness potency, improved sweetness kinetics, increased thermal stability, high pressure stability, increased pH stability, decreased binding to hydrophobic regions, improved freeze-thaw stability, improved reconstitutability after drying, increased solubility, a sensory profile that is closer to that of sugar, and increased shelf-life stability.

According to some embodiments, the food or beverage composition comprising at least one additional food ingredient.

According to some embodiments, the food ingredient is at least one of flavor, food additive, food coloring, preservative, or sweetness enhancer.

According to some embodiments, the food ingredient is selected from the group consisting of stevia, sucrose, agave nectar, brown rice syrup, date sugar, honey, maple syrup, molasses, steviol glycosides, monk fruit, sugar alcohols, rare sugars, aspartame, sucralose, acesulfame potassium, saccharin, neotame, advantame, and dietary fibers.

According to some embodiments, the rare sugars are allulose or tagatose.

According to some embodiments, the food or beverage composition has low glycemic effects.

According to some embodiments, the carbonated soft drink is selected from the group consisting of cola, lemon-lime flavored sparkling beverage, orange-flavored sparkling beverage, grapefruit-flavored sparkling beverage, grape-flavored sparkling beverage, raspberry-flavored sparkling beverage, strawberry-flavored sparkling beverage, pineapple-flavored sparkling beverage, ginger-ale, root beer, and malt beverage.

According to some embodiments, the non-carbonated soft drink is selected from the group consisting of fruit juice, fruit-flavored juice, juice drink, nectar, vegetable juice, vegetable-flavored juice, sports drink, energy drink, protein drink, enhanced water with vitamins, near water drink, coconut water, tea, coffee, cocoa drink, beverages containing milk components, beverages containing cereals extract, and smoothies.

According to some embodiments, the formulation is used in preparing a product for oral delivery.

According to some embodiments, the product is a food or beverage product, a dietary supplement product, or a medicament.

In accordance with some aspects, the present disclosure provides a food or beverage product comprising the formulation of the present invention.

According to some aspects, the present disclosure provides a reduced sugar or no-sugar added soft drink beverage comprising said formulation.

According to some aspects, the present disclosure provides a reduced sugar or no-sugar added dairy product comprising said formulation. According to some embodiments, said dairy product is yogurt or malabi.

According to some aspects, the present disclosure provides a reduced sugar or no-sugar added sauce product comprising said formulation. According to some embodiments, said sauce is ketchup.

According to some aspects, the present disclosure provides a reduced sugar or no-sugar added dried fruits comprising said formulation. According to some embodiments, said dried fruits are selected from the group consisting of cranberries, raisins. blueberries, prunes, cherries, apples, pineapple, watermelon, cantaloupe, figs, bananas, dates, currants, and apricots. According to some embodiments, said dried fruits is fruit leather.

According to some aspects, the present disclosure provides a reduced sugar or no-sugar added gum product comprising said formulation. According to some embodiments, said gum product is chewing gum or bubble gum product.

According to some aspects, the present disclosure provides a reduced sugar or no-sugar added spread product comprising said formulation. According to some embodiments, said spread product is peanut butter.

According to some aspects, the present disclosure provides a reduced sugar or no-sugar added syrup product comprising said formulation.

BRIEF DESCRIPTION OF THE DRAWINGS

In order to better understand the subject matter disclosed herein and to exemplify how it may be carried out in practice, embodiments will now be described, by way of a non-limiting example only, with reference to the accompanying drawings, in which:

FIG. 30A shows alignment of the crystal structure of DM31 (black) with a crystal structure of MNEI (PDB ID: 2o9u) (white). The smaller panels in FIG. 30A zoom-in on selected amino acid changes in DM31, as well as on a loop that was redesigned. The redesigned loop led to increased stability, as well as to new hydrogen bonds and two elongated beta-strands nearby (FIG. 30A, lower right-most panel). FIG. 30B shows the superposition of the same loop region of DM31 with additional MNEI structures available in the public database. DM31 is marked in black.

FIGS. 32A-32C show stabilizing hydrogen bonds in the crystal structures of MNEI (FIG. 32A), DM09 (FIG. 32B), and DM31 (FIG. 32C). The redesigned loop region is highlighted with a black frame.

FIGS. 33A-33B show the loop region in the crystal structure on DM31 (FIG. 33A), compared to a classical definition of a beta-turn (FIG. 33B). The loop structure of DM31 (FIG. 33A) matches schematic definition shown in FIG. 33B.

FIGS. 34A-34B are images of 16% SDS PAGE Tricine protein gels and stained with Coomassie blue, of 1 ug of in vitro digested samples before digestion (T0), at the end of oral phase (3 min, M), at the end of gastric digestion phase (2 hr, G), and at the end of the intestinal duodenal phase (2 hr, D), FIG. 34B shows an image of α-lactalbumin used as positive control, M, G and D as detailed in connection with FIG. 34A.

DETAILED DESCRIPTION OF THE INVENTION

Figure 1:
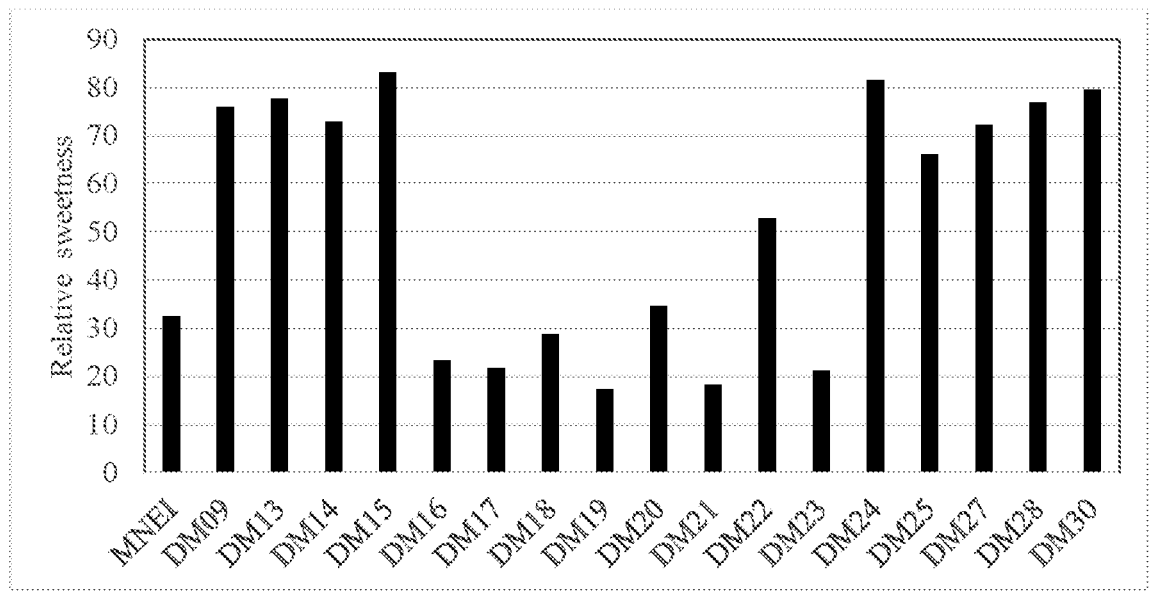
FIG. 1 is a histogram showing the relative sweetness of MNEI and MNEI modified proteins sweetness was evaluated at 6° Bx based on the potency of 1:4000, diluted in water, relative to DM09.

Artificial low-calorie sweeteners are readily available in the market, yet many have significant side effects. For example, saccharin, widely used to sweeten foods and beverages without added calories or carbohydrates, has been linked to cancers such as bladder cancer. Thus, there is a significant need for replacements of the currently available artificial low-calorie sweeteners that will provide both an optimal sensory profile and be suitable for use in food products and beverages.

The present disclosure relates to MNEI based sweet proteins and MNEI taste modifying proteins and is based on identification of proteins that exhibit improved properties relative to known sweeteners. Such proteins were identified by optimization methods, for example, various computational methods.

Surprisingly, the inventors have found that introducing various specific deletions, or substitutions in an amino acid sequence of MNEI (denoted herein as "reference protein") resulted in a protein having at least one improved property compared to the reference MNEI protein. It was suggested that the at least one improved property of the protein might be significant in the fitness and use of the modified MNEI protein in food and beverage applications.

Specifically, as shown in the Examples below, the proteins (denoted herein as "modified protein" or "designer protein") exhibited an improved sensory profile and/or stability as compared to their reference protein. The sensory profile, as described herein, relates to a taste profile (e.g., sweetness potency, aftertaste, and lingering).

Thus, the present disclosure, in its broadest aspect, relates to a modified MNEI protein comprising an amino acid sequence that has at least two amino acid deletions, replacements (substitutions) and/or insertions as compared with a sequence of a reference MNEI protein, wherein the modified protein has at least one improved food-related property as compared with the reference MNEI protein.

The at least one improved food-related property encompasses a property that increases the modified protein's fitness in food and beverage applications, such as flavor, texture, taste, sweetness threshold, sweetness level, sweetness profile, sensory profile, sweetness kinetics, stability (structural and functional), heat resistance, fitness to a food matrix, shelf-life, masking and/or enhancement of other flavors, off-taste, taste onset, lingering taste, taste roundness, or sugar-like taste.

In some embodiments, the at least one food-related property is a sensory-affecting property. The term "sensory-affecting property," as used herein, refers to a change in the sensory impression as determined, for example, by taste. The sensory-affecting property includes, for example, sweetness profiles such as sweetness potency (sugar-like flavor), sweetness kinetics (onset time, lingering time, taste duration), lack of off-taste (e.g., metallic taste), and masking or enhancing other tastes. For example, an improved property relates to increased sweetness, reduced onset time, or reduced lingering taste.

In accordance with some embodiments wherein the at least one property is the sensory-affecting property, the modified protein may be considered a sugar substitute. In some embodiments, the at least one food-related property is at least one of sweetness potency, reduced onset time, or reduced lingering taste.

In some embodiments, the at least one food-related property is stability. In some embodiments, the stability is at least one of thermal stability, longer shelf-life, stability to low-pH, salt concentration stability, ionic strength stability, or stability in a fat-containing or protein-containing matrix. In some embodiments, the at least one food-related property is thermal stability.

In some embodiments, the at least one food-related property is increased shelf-life stability. For example, the modified protein may be stable for at least a week, two weeks, a month, and even over a year.

Shelf-life stability is tasted by differential scanning calorimetry, differential scanning fluorometry, circular dichroism and sensory analysis. In some embodiments, the food taste is maintained, and the protein is intact.

As detailed above, the modified MNEI protein may be used in combination with at least one additional food ingredient. In some embodiments, the at least one food-related property may refer to a synergistic effect between the modified MNEI protein and at least one food ingredient. According to some embodiments, said synergistic effect may affect taste enhancement, taste blocking, or taste modification. Non-limiting examples of food ingredients include artificial or natural flavors, food additives, food coloring, preservatives, bulking agents, or additional sugar additives. The food ingredient may have masking or enhancing taste effects.

As described herein, the reference protein is a taste modifying protein and/or a taste enhancer protein and/or a taste protein and specifically a sweet protein. A taste modifying protein improves the sensory profile, e.g., may add a sweet taste to a non-sweet substance, for example, water and sour substances. A tasty protein, as used herein, is known to bind taste receptors and evoke a taste sensation. A sweet protein, as used herein, is known to bind the sweet receptor and evoke a sensation of sweetness. Non-limiting examples of a sweet receptor include Taste receptor heterodimer made of two subunits such as type 1 member 1 (TAS1R1, Uniprot ID for human gene: TS1R1_HUMAN), Taste receptor type 1 member 2 (TAS1R2, T1R2, TR2, UniProt-Q8TE23), Taste receptor type 1 member 3 (TAS1R3, T1R3, UniProt-Q7RTX0).

In some embodiments, the reference protein is a naturally occurring protein. In some other embodiments, the reference protein is found in plants, such as tropical plants. Non-limiting examples of plants include at least one of capparis masaikai, oubli, serendipity berry, katemfe, miracle fruit berry, or lemba.

In some embodiments, the reference protein is Monellin.

In some embodiments, the reference protein is Monellin made of chain A (GenBank Entry No. P02881) and chain B (GenBank Entry No. P02882).

In some embodiments, the reference protein is MNEI.

The main difference between wild-type Monellin and MNEI is a region in which a Gly-Phe dipeptide was used to connect the two subunits into a single-chain Monellin termed MNEI.

In some embodiments, the reference protein is a sequence not found in nature and is thus called a synthetic protein, or an engineered protein or a designer protein. The synthetic protein may comprise the entirety or part of the amino acid sequence of the naturally occurring protein (all or part of the protein's polypeptide chains) or part thereof. For example, the reference protein may comprise a bond modification of a naturally occurring protein, resulting in a single polypeptide chain that corresponds to a naturally occurring protein, such that the at least two polypeptide chains of the wild-type protein are covalently attached by other amino acids.

In some embodiments, the reference protein is a modified Monellin protein known as MNEI.

In some embodiments, the reference protein is a single chain Monellin (MNEI) protein (SEQ ID NO:45). The MNEI amino-acid numbers referred to herein are in accordance with Protein Databank (PDB) ID 2o9u.

The modified proteins described herein can be designed by various methods.

In some embodiments, protein design is done using computational tools or by expert protein design and structural biology methods, e.g., site-directed mutagenesis, protein engineering, or directed evolution, as further described below. The inventors have developed computational methodologies based on sequence data, structural data, and/or evolutionary data of the reference flavor proteins and other proteins that have local or global similarities to the reference flavor protein in sequence and/or structural features. The computational methods developed and applied herein enabled the inventors to design proteins with specific amino acid substitutions that are energetically favorable and thus are predicted to have improved traits such as thermostability, halostability, pH-stability, shelf-life, folding, and solubility features. Specifically, Computational Protein Design (CPD) was applied to specific sites or regions within the reference protein structure and/or sequence that are not necessary for functional binding to the receptor. In addition, CPD allowed the inventors to limit the substitutions to a predefined set of amino acids that fit the required improved features. The predefined set of amino acids is both in the input data, i.e., the regions of the protein subjected to CPD, and in the output data, i.e., the location and types of amino acids present in the resulting modified protein.

For example, by using CPD it is possible to replace "non-ideal" amino acids (such as hydrophilic amino acids within a hydrophobic core or hydrophobic amino acids on the external surface region) with "ideal" amino acids (such as hydrophilic amino acids in the external surface region and hydrophobic amino acids within a hydrophobic core).

Without being bound by theory, the inventors suggest that substituting hydrophobic amino acids with hydrophilic amino acids on the external surface region will reduce non-specific binding to the oral cavity and reduce the lingering aftertaste.

The methodologies developed herein comprise searching for "stabilizing substitutions," e.g., amino acid substitutions that will decrease the protein structure's overall energy. The overall energy may be calculated by applying known algorithms in the art. Non-limiting examples of such algorithms include Rosetta, OSPREY (M. Hallen, J. Martin, et al., Journal of Computational Chemistry 2018; 39 (30): 2494-2507), or EnCoM (Frappier V, Chartier M, Najmanovich R J. Nucleic Acids Res. 2015;43 (W1): W395-400). These CPD methods undergo focusing and filtering by an array of orthogonal methods such as evolutionary sequence and structural consensus, regular and high-temperature molecular dynamics (MD) and other dynamic simulations, correlated mutational analysis (CMA), surface electrostatics analysis, visual inspection, as well as analysis of cavities, hydrophobic patches, unsatisfied hydrogen bonds and alike.

The amino acid substitutions are based on the following considerations: (a) surface electrostatic potential and (lack of) hydrophobic patches on the surface, (b) retention of the protein's isoelectric point (pI) in a specific range, (c) analysis of the intra-protein cavities, (d) dynamic stability including correlated mutational analysis, normal mode analysis, and root mean square fluctuations (RMSF) in high-temperature or room temperature dynamics, (e) entropic and/or enthalpic components of the substitution energetics, (f) visualization of the specific substitution, (g) types of amino-acids permitted in the family of related proteins; as reflected by an evolutionary conservation analysis of a curated multiple sequence alignment (MSA), and (h) frequency of the substitution as reflected in low-pseudo-energy CPD calculations.

The computational methodologies include one or more of the following steps:

(1) Multiple Sequence Alignment (MSA) or Multiple Structural Alignment. In this step, DNA sequences and/or protein sequences with similarity to the target reference protein or fragments thereof are queried in public databases. Based on the obtained results, a multiple-sequence alignment (MSA) or multiple structural alignment is constructed and the conservation rate is calculated. According to MSA results, a decision regarding the level of CPD to be conducted is made. In non-conserved positions, all amino acids (with or without Cysteine) are allowed in CPD, whereas for more conserved positions, the CPD is limited to residues with similar properties (charge, size, internal dynamics, etc.). This step involves limiting the substitutions in each position based on biophysical knowledge and conservation data. The MSA may yield a Position Specific Substitution Matrix (PS SM) in which each location along the sequence is described in a way correlated with the relative abundance of each amino acid possibly taking into account a potential probability of substitution or of deletion or insertion of amino acids.

(2) Protein function analysis and analysis of structure-function-dynamics relationships. In this step, a database of substitutions with known impact (such as on activity, structure, binding, etc.) is constructed using prior knowledge. Substitutions and substitution-adjacent positions (e.g., a distance of 0.5-1 nm), known, based on prior knowledge, to disturb protein stability and/or function are limited during CPD and are not substituted.

(3) CPD. This step is partially done by designated software such as ROSETTA, OSPREY, SCWRL, PyMol, AlphaFold and alike. Before deterministic CPD is conducted, the reference protein 3D structure/model is energy minimized. The CPD may include site-directed amino-acid replacement where one amino-acid is replaced by another or replacement of protein regions by other amino-acid sequences such resulting in a protein with the different length. The latter can be done by rebuilding regions such as loop by ab initio methods or by taking regions from other proteins, a method that may be referred to as 'grafting'. For each reference protein, multiple models are considered.

(4) Selection: The models of proteins with the lowest energy are collected. An MSA is assembled on these models, and a conserved sequence is determined. Based on biochemical and biophysical pre-knowledge, subsets of substitutions are chosen. These subsets represent replacements at one or more positions that appear during CPD in high frequency. Each subset is then modeled on a 3D structure of the protein and energy minimized. The lowest energy subset is then selected for further computational and experimental validation.

One of the considerations used in CPD is the receptor binding site and whether to substitute amino acids in the binding region and its proximity. Determining the amino acids residues crucial to taste receptor binding may be generally done by single point substitution of various amino acids. As detailed here in the Examples, the inventors have used computational analysis for characterizing the putative binding sites to the taste receptor. The inventors have identified several novel binding sites in the taste receptor that bind to the reference and the modified proteins.

Another consideration in CPD is retaining the functional plasticity required for binding to the receptor while increasing the thermal stability, which intrinsically is often associated with protein rigidification. The protein must undergo some conformational changes (also known as 'functional plasticity') in order to activate the receptor. The inventors thus focused on regions which can be rigidified while conserving regions where functional plasticity must be retained.

The modified MNEI protein is based on the reference MNEI protein (amino acid sequence) and, as such, it should be noted that any feature/property/characterization described herein with respect to the modified MNEI protein is provided relative to the reference corresponding MNEI protein.

As described herein, the modified MNEI protein comprises an amino acid sequence having at least two, at least three, at least four, at least five, at least six, at least ten, at least fifteen, or at least eighteen amino acid substitutions, deletions, or insertions relative to a reference MNEI protein (reference amino acid sequence).

In some embodiments, the modified MNEI protein comprises between two and twenty amino acid substitutions, deletions, or insertions relative to a reference MNEI protein (reference amino acid sequence), between two and ten amino acid substitutions, between three and ten amino acid substitutions, between three and six amino acid substitutions. Ranges used herein are inclusive of the range limits, such that for example, between three and six includes 3, 4, 5, and 6.

In some embodiments, the modified MNEI protein comprises at least two, at least three, at least four, at least five, at least six, at least ten, at least fifteen, or at least eighteen amino acid substitutions, deletions, or insertions relative to a reference MNEI protein having the sequence set forth in SEQ ID NO:45.

In some embodiments, the modified MNEI protein comprises an amino acid sequence 40% to 98% identical to an amino acid sequence of the reference MNEI protein. In some embodiments, the modified MNEI protein comprises an amino acid sequence 90% to 98% identical to the reference amino acid sequence.

In some embodiments, the modified MNEI protein comprises an amino acid sequence 60% to 90% identical to the reference amino acid sequence. In some embodiments, the modified MNEI protein comprises an amino acid sequence 70% to 90% identical to the reference amino acid sequence.

In some embodiments, the modified MNEI protein comprises an amino acid sequence having at least 60%, at least 65%, at least 70%, at least 75%, at least 80%, at least 85%, at least 90%, at least 95%, or at least 98% identity the amino acid sequences set forth in SEQ ID NO:45.

In some embodiments, the modified MNEI protein comprises an amino acid sequence having 90% to 98% identity the amino acid sequences set forth in SEQ ID NO:45.

The % identity between two or more amino acid sequences is determined when the two or more sequences are compared and aligned for maximum correspondence. In the context of the present disclosure, sequences (amino acid) as described herein having % identity are considered to have the same function/activity as the reference sequence to which identity is calculated.

In some embodiments, the modified MNEI protein comprises an amino acid sequence 40% to 98%, similar to an amino acid sequence of the reference MNEI protein. In some embodiments, the modified MNEI protein comprises an amino acid sequence 90% to 98% similarity to the reference amino acid sequence.

In some embodiments, the modified MNEI protein comprises an amino acid sequence 60% to 90% similarity to the reference amino acid sequence. In some embodiments, the modified MNEI protein comprises an amino acid sequence 70% to 90% similar to the reference amino acid sequence.

In some embodiments, the modified MNEI protein comprises an amino acid sequence having at least 60%, at least 65%, at least 70%, at least 75%, at least 80%, at least 85%, at least 90%, at least 95%, or at least 98% similarity with the amino acid sequences set forth in SEQ ID NO:45.

In some embodiments, the modified MNEI protein comprises an amino acid sequence having 90% to 98% similarity with the amino acid sequences set forth in SEQ ID NO:45.

In some embodiments, the modified MNEI protein comprises the amino acid sequence set forth in one of SEQ ID NOs: 1-21, a variant thereof, or a fragment of the foregoing. In particular, the modified MNEI protein may comprise the amino acid sequence set forth in one of SEQ ID NO: 1, 4, 16, 19, or 24, a variant thereof, or a fragment of the foregoing. The modified MNEI protein may also comprise a sequence at least 90, 91, 92, 93, 94, 95, 96, 97, 98, or 99% identical to one of SEQ ID NOs: 1-21, particularly one of SEQ ID NOs: 1, 4, 16, 19, or 24.

Sequence similarity or sequence homology as used herein refers to the amount (%) of amino acids that are conserved with similar physicochemical properties, e.g., leucine and isoleucine.

In determining the sequence identity, gaps are not counted and sequence identity is relative to the shorter sequence of the two. In this context, it should be noted that the length of the reference MNEI protein (amino acid sequence) may be the same as the modified MNEI protein (amino acid sequence) or may be different from the modified MNEI protein (amino acid sequence).

The term "amino acid sequence" and/or "polypeptide chain" are used to describe a protein having an amino acid sequence or polypeptide chain. As such, the term "reference protein" is equivalent to the term "reference amino acid sequence," and the term "modified protein" is equivalent to the term "modified amino acid sequence." It should be noted that the terms "amino acid sequence" and/or "polypeptide chain" encompass sequences having a 3D structure as well as sequences with no 3D structure.

The term "fragment" as used herein in connection with the disclosure relates to proteins or peptides derived from full-length proteins that are shortened, i.e., lacking at least one amino acid. Such fragments may include at least 10, more such as 20, or 30 or more consecutive amino acids of the protein's primary sequence.

The term "variant" as used in the present disclosure relates to derivatives of a protein or peptide that include modifications of the amino acid sequence, for example, by substitution, deletion, insertion, or chemical modification. Such modifications, in some embodiments, do not reduce the functionality of the protein or peptide. Such variants include proteins, wherein one or more amino acids have been replaced by their respective D-stereoisomers or by amino acids other than the naturally occurring 20 amino acids, such as ornithine, hydroxyproline, citrulline, homoserine, hydroxylysine, and norvaline. However, such substitutions may also be conservative, i.e., an amino acid residue is replaced with a chemically similar amino acid residue.

As part of the computational optimization process, the modified proteins may be selected from a large output population of amino acid sequences following computational-, bioinformatic-, or structural-biology analysis, based on energetic considerations, i.e., those sequences with low energy.

Energetic calculations can be applied to the entire amino acid sequence or, alternatively, be restricted to specific regions or selected amino acids within the protein. In the latter (different regions or selected amino acids), the information may be integrated to measure the entire protein.

Calculation of each one of the amino acid sequences (e.g., a modified protein) may be done by combining physico-based (also known as biophysical methods) and statistics-based potentials (also known as knowledge-based potentials or informatics methods), such as by using the Rosetta Energy Unit (REU). Rosetta Energy Unit (REU) is an algorithm of the Rosetta software, a package of algorithms for computational modeling and protein structures analysis. The Rosetta software enables notable scientific advances in computational biology, including de novo protein design, enzyme design, ligand docking, and structure prediction of biological macromolecules and macromolecular complexes. Rosetta energy function is a combination of physical and statistical based potentials that does not match with any actual physical energy units. Rosetta energies are on an arbitrary scale and sometimes referred to as REU (for "Rosetta Energy Unit").

In some embodiments, the REU may be calculated for the entire protein sequence comprising the at least one amino acid substitution. In some other embodiments, the REU may be calculated for at least one region comprising the at least one amino acid substitution of the entire protein sequence. In some other embodiments, the REU may be calculated for at least one amino acid substitution in the entire protein sequence.

In some embodiments, the modified protein has an energy lower than −182 given in REU. In some embodiments, the modified protein has an energy of about −190 given in REU. In some embodiments, the modified protein has an energy of about −195 given in REU. In some embodiments, the modified protein has an energy lower than −195 given in REU. In some embodiments, the modified protein has an energy lower than −196 given in REU. In some embodiments, the modified protein has an energy lower than −197 given in REU. In some embodiments, the modified protein has an energy lower than −198 given in REU. In some embodiments, the modified protein has an energy of about −198 given in REU. In some embodiments, the modified protein has an energy lower than −198.4 given in REU. In some embodiments, the modified protein has an energy lower than −200 given in REU. In some embodiments, the modified protein has an energy lower −203 given in REU. In some embodiments, the modified protein has an energy lower than −206.4 given in REU. In some embodiments, the modified protein has an energy lower than −210 given in REU. In some embodiments, the modified protein has an energy lower than −214.6 given in REU.

In some embodiments, the modified protein has an energy lower than −270.11 given in REU. In some embodiments, the modified protein has an energy lower than −300 given in REU. In some embodiments, the modified protein has an energy lower than −350 given in REU. In some embodiments, the modified protein has an energy lower than −400 given in REU. In some embodiments, the modified protein has an energy lower than −410 given in REU. In some embodiments, the modified protein has an energy lower than −418 given in REU. In some embodiments, the modified protein has an energy lower than −420 given in REU. In some embodiments, the modified protein has an energy lower than −430 given in REU. In some embodiments, the modified protein has an energy lower than −433 given in REU.

In some embodiments, the modified protein has an energy of between −182 given in REU to about −214.6 given in REU. In some other embodiments, the modified protein has an energy of between −195 given in REU to about −214.6 given in REU. In some other embodiments, the modified protein has an energy of between −197 given in REU to about −214.6 given in REU.

As described herein, the modified protein may result from amino acid substitutions or deletions at various regions of the protein. "Regions of the protein" as used herein, refers to an amino acid sequence or structural motif that is part of the protein sequence (amino acid sequence) or structure. Non-limiting examples of protein regions include protein surface, protein core, protein loop, secondary structure elements, secondary structure capping, disulfide, binding-site, linker, hydrophobic-patch, or protein hydrophobic region.

The amino acid substitution in the reference protein is not limited to a specific protein region or sequence. Regions of the reference protein that may include the amino acid substitutions include the reference protein surface, hydrophobic core, or regions called loop regions (also denoted as regions lacking secondary structures), edges of secondary structures (also denoted secondary structure capping regions), disulfide regions, binding-site regions, linker regions, and hydrophobic-patch regions.

As used herein a "reference surface region," "reference core region," or "reference disulfide bond or loop region," may refer to the corresponding region of the reference protein, which may be a reference MNEI protein.

In some embodiments, the reference protein may be substituted within a confined region within the reference protein structure and/or sequence. In some embodiments, the reference protein may be substituted in the surface region. In some embodiments, the reference protein may be substituted in the core region. In some embodiments, the reference protein may be substituted by disulfide bonds. In some embodiments, the reference protein may be substituted in loop regions. In some embodiments, the two or more amino acid replacements are located on the surface of the reference protein.

In some embodiments, the reference protein may be substituted with a confined region that is not in the area adjacent to the predicted or known binding site of the reference protein to the receptor. In this context, 'adjacent' may mean 4-7 Å from the binding interface.

In some embodiments, the reference protein may be substituted at different regions within the reference protein structure and/or sequence. In some embodiments, the reference protein may be substituted at least in the surface region, the core region, the disulfide bond or loop regions, or any combination thereof.

As used herein, the protein surface region is the area with partial or full solvent accessibility (SASA—solvent accessible surface area). The protein core region as used herein, is the area not accessible to solvents with an amino-acid relative SASA (solvent accessible surface area) of less than 50% or, for the inner core, less than 20%.

In some embodiments, the modified protein comprises an amino acid sequence that has 10% to 98%, 20% to 98%, 30% to 98%, 40% to 98%, 50% to 90%, 40%, 50%, 60%, 70%, 80%, 90%, 95%, or 98% identity in the surface region relative to a reference surface region.

In some embodiments, the modified protein comprises an amino acid sequence that has 10% to 98%, 20% to 98%, 30% to 98%, 40% to 98%, 50% to 90%, 40%, 50%, 60%, 70%, 80%, 90%, 95%, or 98% identity in the hydrophobic core (hydrophobic-patch) region relative to a reference hydrophobic core (hydrophobic-patch) region.

In some embodiments, the modified protein comprises an amino acid sequence that has 10% to 98%, 20% to 98%, 30% to 98%, 40% to 98%, 50% to 90%, 40%, 50%, 60%, 70%, 80%, 90%, 95%, or 98% similarity in the hydrophobic core (hydrophobic-patch) region relative to a reference hydrophobic core (hydrophobic-patch) region.

In some embodiments, the modified protein comprises an amino acid sequence having three (3) to forty (40) amino acid substitutions, 4 to 30, 5 to 30 amino acid substitutions in the surface region relative to a reference surface region.

In some embodiments, the modified protein comprises an amino acid sequence having at least one (1), two (2), three (3), at least 4, at least 5, at least 6, at least 10, at least 15, at least 18, at least 20, at least 25 or at least 30 amino acid substitutions in the surface region relative to a reference surface region.

In some embodiments, the modified protein comprises an amino acid sequence that has 20%, 30%, 50%, 80%, 90%, 95%, or 98% identity in the core region relative to a reference core region.

In some embodiments, the modified protein comprises an amino acid sequence that is 20%, 30%, 50%, 80%, 90%, 95%, or 98% similar in the core region relative to a reference amino acid sequence core region.

In some embodiments, the modified protein comprises an amino acid sequence having one to five amino acid substitutions in the core region relative to a reference core region.

In some embodiments, the modified protein comprises an amino acid sequence with 90%, 95%, or 98% identity in the region that binds to the receptor (receptor binding site) relative to a reference region that binds to the receptor in the reference.

In some embodiments, the modified protein comprises an amino acid sequence with 90%, 95%, or 98% similarity in the receptor binding site relative to a reference receptor binding site.

In some embodiments, the receptor binding site of the reference protein is not substituted in the modified protein.

In some embodiments, at least one of the disulfide bonds is removed and the regions around them are redesigned with 8 to 20 substitutions around each of the removed disulfide bonds.

The amino acids may be referred to herein by either their commonly known three letter symbols or by the one-letter symbols recommended by the IUPAC-IUB Biochemical Nomenclature Commission. Amino acid substitution (replacement) as used herein, refers to a change from one amino acid to a different amino acid. This is typically due to a point mutation in the DNA sequence caused by a nonsynonymous missense mutation, which alters the codon sequence to code a different amino acid than the references. An amino acid replacement may affect protein function or structure, generally depending upon how similar or dissimilar the replaced amino acids are and their position in the sequence or structure. For example, the amino acid substitutions may be made based on similarity in size, polarity, charge, solubility, hydrophobicity, hydrophilicity, bulkiness (or flexibility), beta-branching, propensity for residing in a specific secondary structure or in a specific solvent accessibility region, aromaticity, ability to confer specific bonding interactions (hydrogen bonds, salt bridges, polar, and nonpolar interactions), pK, ability to bind sugars and other post-translational modifications, and/or the amphipathic nature of the residues involved.

In some embodiments, the amino acid substitutions may be a conservative replacement. Such a replacement encompasses a change of one amino acid into another amino acid exhibiting similar properties. A conservative amino acid replacement (also denoted as conservative amino acid "substitutions" or conservative amino acid mutations) is an amino acid replacement in a protein that changes a given amino acid to a different amino acid with similar biochemical, structural, and/or chemical properties.

For example, amino acids may be sorted into six main classes based on their structure and the general chemical characteristics of their side chains (R groups).

Aliphatic: Isoleucine (I), Leucine (L), Glycine (G), Alanine (A), Valine (V);

Hydroxyl or sulfur/selenium-containing: Serine (S), Cysteine (C), Threonine (T), Methionine (M);

Cyclic: Proline (P)

Aromatic: Phenylalanine (F), Tyrosine (Y), Tryptophan (W)

Basic: Histidine (H), Lysine (K), Arginine (R)

Acidic and their amides: Aspartate (D), Glutamate (E), Asparagine (N), Glutamine (Q)

In addition, each of the following groups contains other exemplary amino acids that are conservative substitutions for one another:

1) Very small: Alanine (A), Glycine (G);
2) Negative charge: Aspartic acid (D), Glutamic acid (E);
3) Polar (amidated carboxyl side chain): Asparagine (N), Glutamine (Q);
4) Positively charged: Arginine (R), Lysine (K);
6) Aromatic: Phenylalanine (F), Tyrosine (Y), Tryptophan (W), and occasionally also Histidine (H);
7) Small polar: Serine (S), Threonine (T);
8) Sulfur-containing: Cysteine (C), Methionine (M)
9) Small: Ala (A), Glycine (G), Serine (S).
10) Beta-branched: Valine (V), Isoleucine (I) and occasionally also Threonine (T);
11) Polar: Asparagine (N), Glutamine (Q), Serine (S), Threonine (T);

Nevertheless, there are numerous clusters of amino acids yielding multiple amino acids indexes, each highlighting a different aspect of the amino acid characteristics—e.g., see hundreds of such indexes in the aa index database https://wwx genome.jp/aaindex/. Consequently, some of the conservative replacements may represent other important features for protein fitness for industrial use in the food and beverage industry, e.g., non-specific binding to the tongue or other sensory profile aspects.

An additional conservation analysis is based on the following, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K);

"polar" amino acids are selected from the group consisting of Arginine (R), Lysine (K), Aspartic acid (D), Glutamic acid (E), Asparagine (N), Glutamine (Q);

"positively charged" amino acids are selected from the group consisting of Arginine (R), Lysine (K), and Histidine (H); and "acidic" amino acids are selected from the group consisting of Aspartic acid (D), Asparagine (N), Glutamic acid (E), and Glutamine (Q).

In some embodiments, the replacement is a radical replacement. A radical replacement (substitution) is an exchange of an amino acid into another amino acid with different properties.

The degree of sequence similarity and/or sequence identity between the reference protein and the modified protein may generally affect the modified protein's properties. For example, a large number of substitutions may affect the binding kinetics, folding kinetics, solubility, thermostability, halostability, pH stability, shelf-life, binding to non-aqueous particles (e.g., protein or fat in food matrix or hydrophobic regions in the oral cavity), 3D structure, as well as its activity and related properties. The computational methods developed and applied herein provide a thorough understanding of putative amino acid residues for substitution that will result in improved modified proteins.

In accordance with some aspects, the reference protein is MNEI having an amino acid sequence set forth in SEQ ID NO:45. As shown in Example 1 below, CPD analysis has revealed several amino acids as targets for substitution or deletion.

In some embodiments, the at least one amino acid substitution is a conservative substitution. In some embodiments, the at least one amino acid substitution is a radical substitution. In some embodiments, two or more amino acids are substituted.

Amino acid substitutions in MNEI were previously reported, including multiple mutations. For example, Zheng et al. reported novel double mutant MNEI-based proteins with improved sweetness and stability. Specifically, Zheng et al. demonstrated that a single substitution E2N in MNEI resulted in a 3-fold improved sweetness and slightly reduced stability. Zheng et al. further showed that introducing an additional substitution, E23A or Y65R, in addition to the E2N substitution (e.g., E2N/E23A, E2N/Y65R), did not affect sweetness.

In some embodiments, at least two or at least three of the at least three amino acid substitutions in a reference protein being MNEI is a conservative substitution.

As described herein, the modified MNEI protein described herein has an improved food-related property. The protein's sweetness profile, such as sweetness potency (sugar-like flavor), lack of off-taste, reduced onset time, and reduced lingering taste of the modified protein, may be determined by any known taste test known in the art. For example, a comparison to the sweetness of sucrose or other sweeteners can be made by a taste panel, and the sweetness potency may be graded as detailed in the examples below.

The comparison may be made by determining the modified protein's threshold as compared to a known sweetener, such as sucrose, for example, by determining the minimum concentration required to evoke the sensation of sweetness, or a sweetness profile assessment, including characteristics such as sweetness profile, sweetness onset time, lingering taste, mouthfeel, aftertaste, off-taste, and masking of unwanted tastes.

As used herein, the term sweetening-affecting properties encompass a sweet sensation determined by at least one of a sweetness threshold of about 0.28 mg/L, of about 0.5 mg/L, or higher, sweetness duration of about between 1 to 20 seconds, at times between 2 to 18 seconds, at times between 2-4 seconds The modified MNEI protein, like the reference MNEI protein, binds to the sweet receptor.

In some embodiments, the modified MNEI protein has a perceived sweetness threshold that is 300-16,000 higher than sugar on a per weight basis.

The sensory profile includes taste kinetics showing taste intensity over time, i.e., onset duration (time until feeling taste), taste duration, and time of lingering taste (corresponding to a gaussian tail). Additional features include off-taste (e.g., due to binding to other receptors), taste roundness, metallic and other side-tastes, synergy with other ingredients (e.g., masking and enhancing other flavors or unwanted tastes, such as stevia), mouthfeel, astringency, and alike.

In some embodiments, the modified protein is characterized by at least one of the following being equal or improved relative to the reference protein: (1) structural thermal stability, (2) functional thermal stability, (3) pH stability, (4) solubility in water or a partly aqueous milieu (e.g., foods containing fat), or (5) shelf-life stability.

The modified protein described herein is characterized by a sweet taste as well as other taste effects (masking unwanted tastes, less aftertaste, less lingering taste, less off-taste, umami taste, better mouthfeel) that may be used as a sweetener in the preparation of a product for oral delivery.

The modified proteins can be used as a flavor modifying agent or a flavor-enhancing agent.

The modified protein described herein is for use as an oral product. In some embodiments, the product is a food or beverage product, a dietary supplement product, or a medicament. For product preparation, the proteins described herein may be combined with any food-grade additive. The food or beverage product may be provided and used in any solid dry form, including, without being limited thereto, fine powder, lyophilizate, granulate, tablets, etc. In some embodiments, the composition is provided in liquid form, for example, as a solute in water (aqueous solution).

The product comprising the modified proteins may have various applications. This includes, without being limited thereto (each of the following constituting a separate embodiment of the present disclosure), utilization as a sweetener, flavor, enhancer, maskers, and proteins that have flavor characteristics in the food and beverage industry (fruit and vegetable juice and nectars, soft drinks, ready-to-drink beverages, syrups, functional drinks, sports drinks, etc.), in the dairy industry, i.e., dairy products, yogurts, and puddings; in the pharmaceutical industry; the naturopathic industry, the nutraceutical industry (e.g., nutraceutical bar), and other healthcare products (e.g., toothpaste and mouthwash), confectionery, candy and gum industry, vegetables (e.g., ketchup or sauces) or any other application that requires the use of a flavor modifying composition as an excipient or additive.

According to some embodiments, the additional food ingredient is selected from a group consisting of sucrose, fructose, glucose, agave nectar, brown rice syrup, date sugar, honey, maple syrup, molasses, monk fruit, sugar alcohols, rare sugars, steviol glycosides, aspartame, sucralose, acesulfame potassium, and dietary fibers.

In some embodiments, the modified protein has structural thermal stability equal or improved relative to the reference protein.

The term "structural thermal stability" or "thermal stability" as used herein refers to the ability of the modified protein to retain its 3D structure at temperatures above that of the reference protein. The 3D structural stability of a protein can be measured by any method known in the art, such as Circular Dichroism (CD), or thermal shift assays such as Differential Scanning Fluorimetry (DSF) or Differential Scanning calorimetry (DSC) or titration with protein denaturating agents such as guanidinium chloride. The 3D protein structure may influence protein function. Notably, the shelf-life and thermal stability required for food and beverage products may be related to the structural thermal stability and consists of different measurables, e.g., pasteurization (or heat treatment during preparation of the consumer-packaged good final product) can be applied by different protocols and is related to the heat resistance of retaining the protein structure over a very short time.

In some embodiments, the modified protein has functional thermal stability equal or higher relative to the reference protein. The term "functional thermal stability" as used herein refers to the ability of the modified protein to retain its function after exposure to high temperatures compared with the reference protein.

In some embodiments, the modified protein herein may maintain its sweetness effect at a higher temperature or after exposure to a higher temperature for a limited time. In other words, there is no apparent change in the sweetness or sensory profile after product exposure to a temperature above room temperature, at times, up to 50° C., at times up to 100° C., or even up to 150° C. The protein function, e.g., sweetness, may be measured by sensory tests after the protein is cooled down to a temperature in which it can be tasted.

In some embodiments, the modified protein has pH stability being equal or higher relative to the reference protein. pH stability refers to the long-term stability of the modified protein at a wider pH range relative to the reference protein, namely the modified protein maintains the 3D structure and/or function after exposure of the product to any pH from 3 to 8, at times, at a pH of between 4 to 8. For example, a soda like cola has a pH of 2.3-2.5, at which some of the sweet proteins are unstable and lose functionality immediately or after a time that is shorter than the regular shelf-life of the beverage.

In some embodiments, the modified MNEI protein has a solubility higher than the reference MNEI protein. Solubility may be in an aqueous, partly aqueous, or non-aqueous milieu, such as foods containing fat.

In some embodiments, the modified MNEI protein has an improved shelf-life relative to the reference MNEI protein. Improved shelf-life refers to no sensed change in sweetness (function) or physical deterioration of a product comprising the composition (e.g., color change, phase separation, etc.)

after exposure of the product to any temperature up to 150° C., at times, to any temperature between 4° C. to 150°, or 100°.

In some other embodiments, the modified MNEI protein is characterized by at least one of the following being equal or improved relative to the reference MNEI protein (1) folding kinetics, (2) post-translational modification (e.g., glycosylation or acetylation) pattern of the protein is different than the reference protein, (3) the number of disulfide bonds are higher relative to the reference MNEI protein, which has no disulfide bonds.

In some embodiments, the modified MNEI protein has folding kinetics equal or higher relative to the reference MNEI protein. Namely, the protein folding rate from an unfolded or partially folded structure is faster (as assessed in silico, e.g., by molecular dynamics or by experimental in vitro or in vivo methods). Alternatively, faster folding kinetics refers to slower unfolding kinetics in denaturation experiments, e.g., by denaturant titrations (e.g., guanidinium chloride and/or high-concentration urea) or other methods.

In some embodiments, the modified MNEI protein is characterized by an expression yield equal or higher relative to the reference MNEI protein in the host organism assessed.

In some embodiments, the modified MNEI protein has a pI value of between 8.6 to 9.5.

The modified MNEI protein described herein is characterized by a sweet taste as well as other taste effects (masking unwanted tastes, less aftertaste, less lingering taste, less off-taste, less lingering taste onset, and umami taste) may be used as a sweetener in the preparation of a product for oral delivery.

The modified MNEI protein can be used as a flavor modifying agent or a flavor-enhancing agent.

The modified MNEI protein described herein is for use as an oral product. In some embodiments, the product is a food product, a food supplementary product, or a medicament. For product preparation, the proteins described herein may be combined with any food-grade additive. The food product may be provided and used in any solid dry form, including, without being limited thereto, fine powder, lyophilizate, granulate, tablets, etc. In some embodiments, the composition is provided in liquid form, for example, as a solute in water (aqueous solution).

The product comprising the modified MNEI proteins may have various applications. This includes, without being limited thereto (each of the following constituting a separate embodiment of the present disclosure), utilization as a sweetener, flavor, enhancer, or masker in the food and beverages industry (fruit and vegetable juice and nectars, soft drinks, ready-to-drink beverages, syrups, functional drinks, sports drinks, etc.), in the dairy industry, i.e., dairy products, yogurts, and puddings, in the pharmaceutical industry, in the naturopathic industry, nutraceutical industry, and other healthcare products (e.g., toothpaste and mouthwash), confectionary, candy and gum industry, vegetables (e.g. ketchup or sauces) or any other application that requires the use of a flavor modifying composition as an excipient or additive.

The product may comprise additional food ingredients. In some embodiments, the food ingredient is a sweetener, for example, a steviol glycoside. The combination of the modified protein described herein and a steviol glycoside produce a synergetic effect. Thus, in some embodiments, the product comprises at least one modified protein denoted by SEQ ID NOs:1-21 and a steviol glycoside.

Wherein Stevia (denoted herein a steviol glycoside or mixture thereof) and/or its varieties are combined with the modified protein of the present invention at the range of 0.5° Bx to 8° Bx sucrose equivalent, the modified protein represents the replacement of 30% to 70% of Sucrose sweetness. The perceived sweetness intensity is at least 100% of stevia solution at a sucrose equivalent of 0.5° Bx to 8° Bx.The perceived lingering sensory profile is superior to 100% of a stevia solution at a sucrose equivalent of 0.5° Bx to 8° Bx. The perceived sourness sensory profile is superior to 100% of a stevia solution at a sucrose equivalent of 0.5° Bx to 8° Bx.

According to some embodiments, the additional food ingredient is selected from the group consisting of sucrose, agave nectar, brown rice syrup, date sugar, honey, maple syrup, molasses, monk fruit, sugar alcohols, rare sugars, aspartame, sucralose, acesulfame potassium, and dietary fibers.

In some embodiments, the formulations described herein provide a sugar-like taste profile with a decreased, eliminated, or masked aftertaste or off-flavor (e.g., metallic or licorice taste) or a decreased, eliminated, or masked bitterness or decreased, eliminated, or masked sweet taste lingering.

It should be noted that the modified MNEI proteins, according to the invention, can be produced by any method known in the art, for example, the protein can be produced synthetically, by recombinant DNA technology, or by protein production in microorganisms via fermenters, plants, plant callus, or other bioreactors. In some embodiments, the modified proteins may be produced in bacteria, such as *E. coli*. In some other embodiments, the modified proteins may be produced yeast, such as *Saccharomyces cerevisiae* or *Pichia pastoris*. In some other embodiments, the modified proteins may be produced in filamentous fungi such as *Trichoderma*, or *Aspergillus*.

The term "yeast and filamentous fungi" include, but are not limited to any *Kluyveromyces* sp., such as *Kluyveromyces lactis*, *Kluyveromyces marxianus*, *Saccharomyces* sp., such as *Saccharomyces cerevisiae*, *Pichia* sp., such as *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pyperi*, *Pichia stiptis*, *Pichia methanolica*, *Hansenula polymorpha*, *Candida albicans*, any *Aspergillus* sp., such as *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens*, *Myceliopthora* and *Neurospora crassa*.

In some embodiments, the DNA sequence of the chosen amino acid sequence is optimized at the RNA and DNA levels. At the RNA level, this includes minimization of RNA secondary structures to ensure quick insertion into the ribosome. At the DNA level, this includes codon optimization to the host organism (taking into account the RNA-level optimization). Codon-usage optimization provides preference for using the most abundant tRNA in the host organism for each amino acid expressed.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

All scientific and technical terms used herein have meanings commonly used in the art, unless otherwise specified. The definitions provided herein are to facilitate understanding of certain terms used frequently herein and are not meant to limit the scope of the present disclosure.

As used herein, the term "about" refers to ±10%. The terms "comprises," "comprising," "includes," "including," "having," and their conjugates mean "including but not limited to". The term "consisting essentially of" means that the composition, method, or structure may include additional ingredients, steps and/or parts, but only if the additional ingredients, steps and/or parts do not materially alter the basic and novel characteristics of the claimed composition, method or structure. The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

It must be noted that, as used in this specification and the appended claims, the singular forms "a", "an" and "the" include plural referents unless the content clearly dictates otherwise.

"Solution," as used herein, refers to a liquid mixture in which the minor component (the solute) is uniformly distributed within the major component (the solvent). A solution is clear and does not contain particulate matter, in contrast to a suspension or cloudy mixture.

"Syrup" or "Beverage syrup," as used herein, refers to a beverage precursor to which a fluid, typically water, is added to form a ready-to-drink beverage or a "beverage." Typically, the volumetric ratio of syrup to water is between 1:3 to 1:8, more typically between 1:4 and 1:6. The volumetric ratio of syrup to water also is expressed as a "throw." A 1:5 ratio, a ratio commonly used within the beverage industry, is known as a "1+5 throw."

The formulations can be used "as-is" or in combination with other sweeteners, flavors, and food ingredients.

Non-limiting examples of sweeteners include steviol glycosides, stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in Stevia Rebaudiana Bertoni plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols.

Non-limiting examples of flavors include cranberries, lemon, orange, banana, grape, pear, pineapple, guarana, apple, mango, bitter almond, cola, cinnamon, sugar, cotton candy, and vanilla flavors.

Non-limiting examples of other food ingredients include flavors, acidulants, organic and amino acids, coloring agents, bulking agents, modified starches, gums, texturizers, preservatives, antioxidants, emulsifiers, stabilizers, thickeners, and gelling agents.

As used herein, the phrases "sugar-like characteristic," "sugar-like taste," "sugar-like sweetness," "sugary," and "sugar-like" are synonymous. Sugar-like characteristics include any characteristic similar to that of sucrose and include, but are not limited to, maximal response, flavor profile, temporal profile, adaptation behavior, mouthfeel, concentration/response function behavior, taste and flavor/sweet taste interactions, spatial pattern selectivity, and temperature effects. These characteristics are dimensions in which the taste of sucrose is different from the tastes of natural and synthetic high-potency sweeteners. Whether or not a characteristic is more sugar-like is determined by an expert sensory panel's assessment of sugar and the functional taste-improving compositions. Such assessments quantify similarities in the composition characteristics. Suitable procedures for determining whether a composition has a more sugar-like taste are well known in the art.

The term "flavor" or "flavor characteristic," as used herein, is the combined sensory perception of the components of taste, odor, and/or texture. The term "enhance," as used herein, includes augmenting, intensifying, accentuating, magnifying, and potentiating the sensory perception of a flavor characteristic without changing the nature thereof. The term "modify," as used herein, includes altering, varying, suppressing, depressing, fortifying, and supplementing the sensory perception of a flavor characteristic where the quality or duration of such characteristic was deficient.

"Taste-modifying proteins (TMP)" as used herein are defined as proteins acting as substitutes of basic tastes such as, but not limited to, sweet, umami, as well as blockers, enhancers, maskers, and proteins that have flavor characteristics.

The "high-intensity sweetener" in the present invention means a protein with strong sweetness compared to sucrose and may be a naturally occurring protein, a recombinant protein, or a combination thereof. The high-intensity sweetener exhibits sweetness 5 times or more, 10 times or more, 50 times or more, 100 times or more, 500 times or more, 1000 times or more, 5000 times or more, 10000 times or more, 50000 times or more, 100000 times or more than sucrose in the same amount.

The "nutritional function components," as used herein, refer to nutrients for humans and refer to any one or more selected from the group consisting of mineral, organic acid, vitamin, polyphenol, protein, amino acid, dietary fiber, and glucide (except for saccharides).

The term "functional," as used herein, refers to the preservation of function (e.g., sweetness) following thermal or other processes (albeit possible structural changes).

The term "functional stability," as used herein, refers to stability in a formulation or consumer-packaged good conditions and the stability of maintaining the functional sensory properties rather than the chemical stability of pure material in dry, water, or buffer form.

As used herein, the term "foodstuff" means any edible oral composition, including beverages, confectionery products, chewing gum products, or food products.

The term "beverage" as used herein means any drinkable liquid or semi-liquid, including, for example, flavored water, soft drinks, fruit drinks, coffee-based drinks, tea-based drinks, juice-based drinks, milk-based drinks, jelly drinks, carbonated or non-carbonated drinks, alcoholic or non-alcoholic drinks.

As used herein, "orally ingestible composition" and "sweetening composition" are synonymous and refer to substances which contact the mouth of man or animal, including substances taken into and subsequently ejected from the mouth and substances which are drunk, eaten, swallowed, or otherwise ingested, and are safe for human or animal consumption when used in a generally acceptable range. These compositions include food, beverage, pharmaceutical, nutraceutical, oral hygienic/cosmetic products, and the like. Non-limiting examples of these products include non-carbonated and carbonated soft drinks (CSDs) such as colas, ginger ale, root beers, ciders, fruit-flavored soft drinks (e.g., citrus-flavored soft drinks such as lemon-lime, cranberries or orange); powdered soft drinks and the like; fruit juices originating in fruits or vegetables; fruit juices including squeezed juices or the like; fruit juices containing fruit particles, fruit beverages, fruit juice beverages, beverages containing fruit juices, beverages with fruit flavorings, vegetable juices, juices containing vegetables, and mixed juices containing fruits and vegetables; sports drinks, energy drinks, near water and the like drinks (e.g., water with natural or synthetic flavorings); tea type or beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; dairy products; bakery products; desserts such as yogurt, jellies, gummies, drinkable jellies, puddings, Bavarian cream, blancmange, cakes, brownies, mousse, peanut butter, and the like, sweetened food or beverage products eaten at tea time or following meals; frozen foods; cold confections, e.g., types of ice cream such as ice cream, ice milk, lactose-ice and the like (food or beverage products in which sweeteners and various other types of raw materials are added to milk products and the resulting mixture is agitated and frozen), and ice confections such as sherbets, dessert ices and the like (food or beverage products in which various other types of raw materials are added to a sugary liquid and the resulting mixture is agitated and frozen); ice cream; general confections, e.g., baked confections or steamed confections such as cakes, crackers, biscuits, buns with bean-jam filling and the like; rice cakes and snacks; table top products; general sugar confections such as chewing gum (e.g., including compositions which comprise a substantially water-insoluble, chewable gum base, such as chicle or substitutes thereof, including rubber or certain comestible natural synthetic resins or waxes), hard candy, soft candy, mints, nougat candy, jelly beans and the like; sauces including fruit flavored sauces, chocolate sauces and the like; edible gels; cremes including butter cremes, flour pastes, whipped cream and the like; jams including strawberry jam, marmalade and the like; breads including sweet breads, and the like or other starch products; spices; general condiments including seasoned soy sauce used on roasted meats, roast fowl, barbecued meat, and the like, as well as tomato catsup (ketchup), sauces, noodle broth, and the like; processed agricultural products, livestock products or seafood; processed meat products such as sausage and the like; retort food or beverage products, pickles, preserves, soy sauce, delicacies, side dishes; snacks such as potato chips, cookies, or the like; cereal products; drugs, quasi-drugs and dietary supplements, that are administered orally or used in the oral cavity (e.g., vitamins, cough syrups, cough drops, chewable medicine tablets, amino acids, bitter-tasting drug or pharmaceutical agents, acidulants, or the like), wherein the drug may be in solid, liquid, gel, or aerosol form such as a pill, tablet, spray, capsule, syrup, drop, troche agent, powder, and the like; personal care products such as oral compositions used in the oral cavity such as mouth freshening agents, gargling agents, mouth rinsing agents, toothpaste, tooth polish, dentrifices, mouth sprays, teeth-whitening agents, and the like; dietary supplements; animal feed; and nutraceutical products, which includes any food or part of a food that may provide medicinal or health benefits, including the prevention and treatment of disease (e.g., cardiovascular disease and levels of high blood cholesterol, diabetes, osteoporosis, inflammation, or autoimmune disorders).

As used herein, Stevia is the common name for Stevia rebaudiana (Bertoni), a perennial shrub of the Asteracae (Compositae) family native to Brazil and Paraguay. Stevia leaves, the aqueous extract of the leaves, and purified steviol glycosides isolated from Stevia, have been developed as sweeteners desirable as both non-caloric and natural in origin. Steviol glycosides isolated from Stevia rebaudiana include stevioside, rebaudioside A, rebaudioside C, dulcoside A, rubusoside, steviolbioside, rebaudioside B, rebaudioside D and rebaudioside F.

Reb M (also called rebaudioside X), (13-[(2-O-.beta.-D-glucopyranosyl-3-O-.beta.-D-glucopyranosyl-.beta.-D-glucopyranosyl)oxy] ent kaur-16-en-19-oic acid-[(2-O-.beta.-D-glucopyranosyl-3-O-.beta.-D-glucopyranosyl-.beta.-D-glucopyranosyl) ester], was isolated from Stevia rebaudiana and characterized.

As described herein, the food or beverage composition has an improved food or beverage related property. The composition's sweetness profile, such as sweetness potency, lack of off-taste, reduced onset time, and reduced lingering taste of the composition, may be determined by any known taste test known in the art. For example, a comparison to the sweetness of sucrose or other sweeteners can be made by a sensory panel, and the sweetness potency may be graded as detailed in the examples below.

NON-LIMITING EXAMPLES

Example 1: Design of MNEI Based Proteins

Design of MNEI-based proteins was conducted as follows: Single-chain monellin, MNEI (SEQ ID NO:45), is a polypeptide composed of 96 amino acids, with a molecular weight of ~11 kD and pI~8.7.

Computational Methods

As described above, the computational and human-expert analysis provides a reduced sequence space that can be further analyzed computationally, by an expert, experimentally, or by a combination of these methods. Such analyses can be applied to individual amino acids, to clusters of amino-acids, or to other combinations.

During the Computational Protein Design (CPD) process, amino acid replacements and/or deletions were allowed in specific regions less likely to be part of the receptor binding site, e.g., around the helix, the non-exposed side of the beta-sheet which forms the protein core, or the engineered loop which differentiates MNEI from wild-type Monellin. A ROSETTA run resulted in 600K models. When the energy of all models was drawn, the outcome graph had the form of a logit function. A logit function (also known as log-odds) is a logarithm of the odds p/(1−p) where p is the probability. It is the inverse of the sigmoidal "logistic" function.

For further analysis, the 5K lowest models were selected. Plotting the number of replacements (compared to MNEI) as a function of REU gave a Gaussian distribution, showing that the populations are normal and valid for further analysis.

Loop Design in MNEI

The Y47-K56 loop (i.e., a Gly-Phe peptide) in MNEI is a flexible loop, demonstrated at pH=2 and 7 by molecular dynamics (MD) simulations. This loop is not native to monellin and was introduced as a linker of the two subunits of the natural monellin (chain A & chain B). In this manner, MNEI was produced. The introduced loop had no impact on sweetness, thus MNEI has the same sweetness as Monellin, however, MNEI has a higher Tm (melting temperature), illustrating the impact that the loops can have on protein stability (Curr Opin Struct Biol. 1999 August; 9 (4):494-9). Identifying the importance of the loop, the inventors redesigned and shortened the loop to increase yield, stability, and sensory profile.

Procedure
Grafting

Following a 3D structure alignment of the loop and two adjacent beta-sheets of

MNEI, two similar proteins were identified. Based on those PDBs, four models were built and minimized using ROSETTA.

Size Based and Ab-initio Modeling

Separately from the grafting procedure outlined above, additional loop alterations were obtained based on physical and biophysical considerations. In order to study the effect of loop length on MNEI stability, loops with varying lengths were modeled using CPD software such as Rosetta or Swiss-PDB-Viewer. Loop modeling was done based on physical consideration using the MNEI sequence or based on homology modeling. Each model was then energy minimized, and the energy was calculated using GROMOS96 43B1 force field. Based on this analysis, loops with 6, 5, and 4 residues were further tested as loops with these lengths were found to be energetically more favorable.

Thermostability

Different variations of MNEI sequence were built and the energy of each model was predicted by Rosetta. For further analysis, the lowest energy sequence DM28 (with a 4mer loop, i.e. a loop of 4 amino acids, shortening the original MNEI loop by 3 amino acids) was selected, and an energy CPD calculation was conducted using Rosetta with 100K repeats. Additional variations were then built using DM28 as a template, combining the 4mer loop with specific amino acid substitutions (resulting in DM29, DM31, DM32 & DM33, see Table 3 and Table 4). One additional variant, DM30, was added, based on DM09. The lowest energy sequence, DM31, was chosen for further analyses.

TABLE 1A

Energy of different
sequences as calculated by ROSETTA.

| Protein | REU |
|---|---|
| MNEI | −198.410 |
| DM09_6mer.loop | −195.663 |
| DM09_5mer.loop | −189.168 |
| MNEI_5mer.loop | −192.917 |
| DM28 | −200.068 |
| DM29 | −198.603 |
| DM30 | −200.03 |
| DM31 | −203.534 |
| DM32 | −201.43 |
| DM33 | −203.061 |
| Crystal structure DM31 | −208.025 |

All calculations were done using Rosetta 3.8.
Note
that the REUs were calculated for theoretical structures of the proteins, with the exception of MNEI, where the calculation was based on PDB ID 2o9u, and the crystal structure of DM31, last row in the table.

Figure 30A:
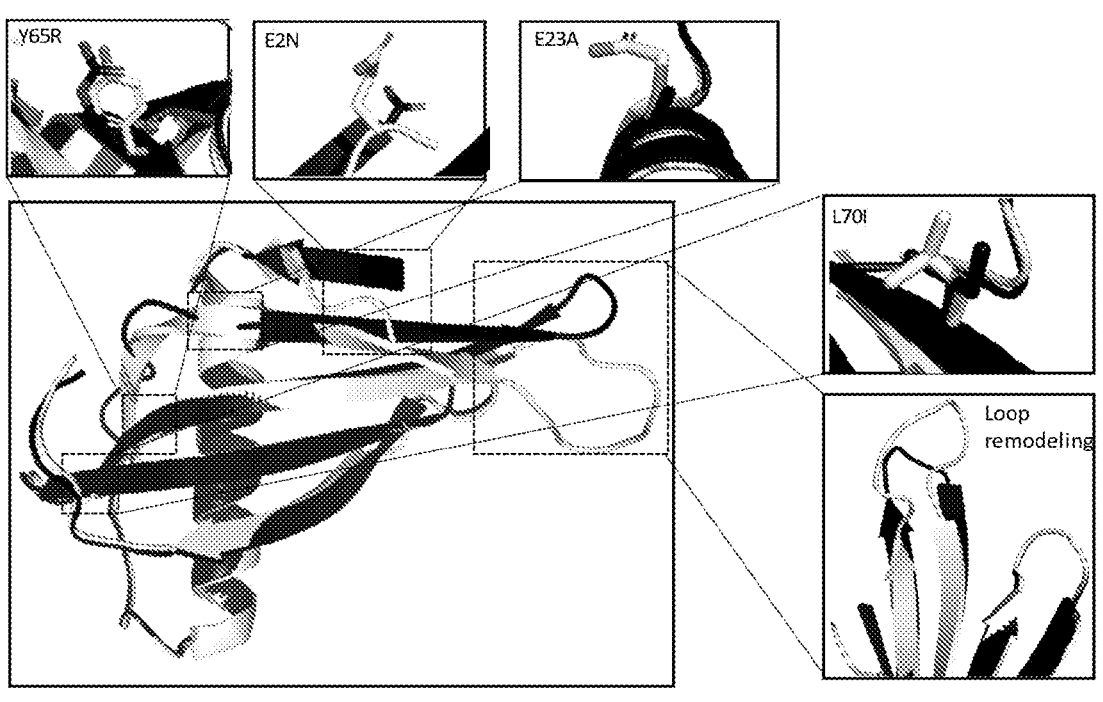
FIGS. 30A-B are crystal structure images highlighting the changes that were made in DM31.
Figure 30B:
Figure 31A:
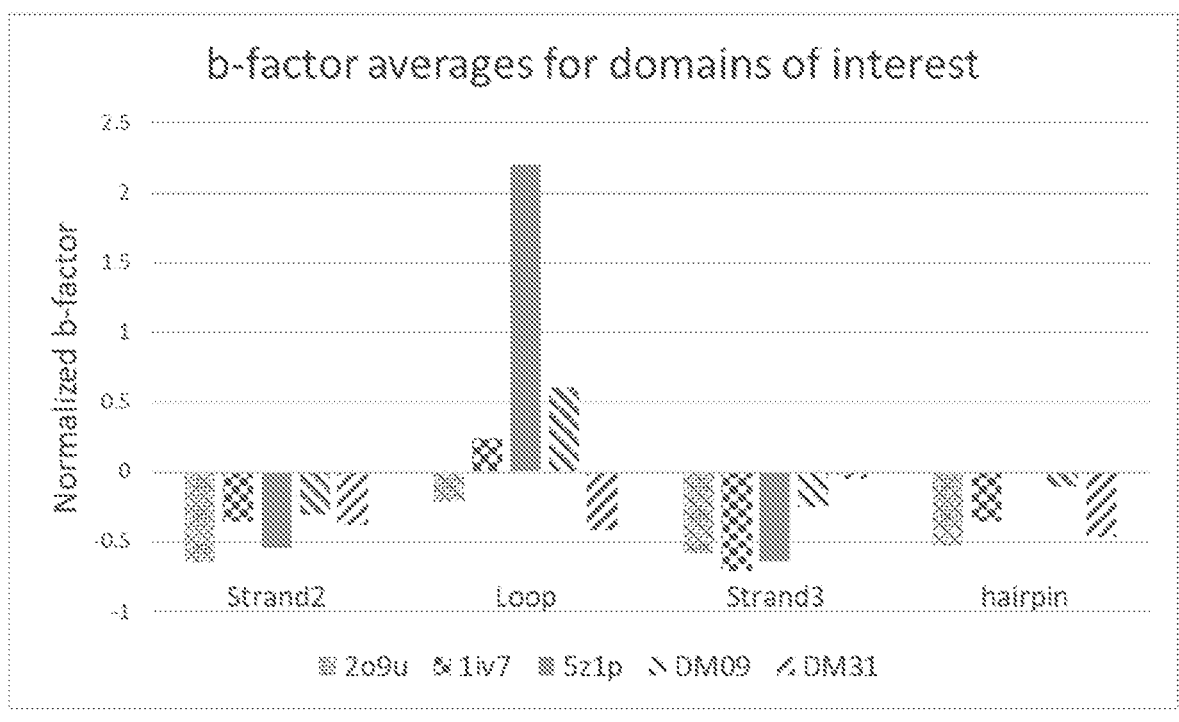
FIGS. 31A-31B are histograms showing the normalized B-factors for a few MNEI structures (2o9u, liv7, 5zlp), DM09, and DM31. Backbone B-factors were first normalized separately for each structure using Z-score normalization. B-factors are shown as averages for different secondary structure elements (FIG. 31A), as well as for specific residues (E48 to E54, numbered according to the sequence of MNEI) that are part of the redesigned loop regions (FIG. 31B).
Figure 31B:
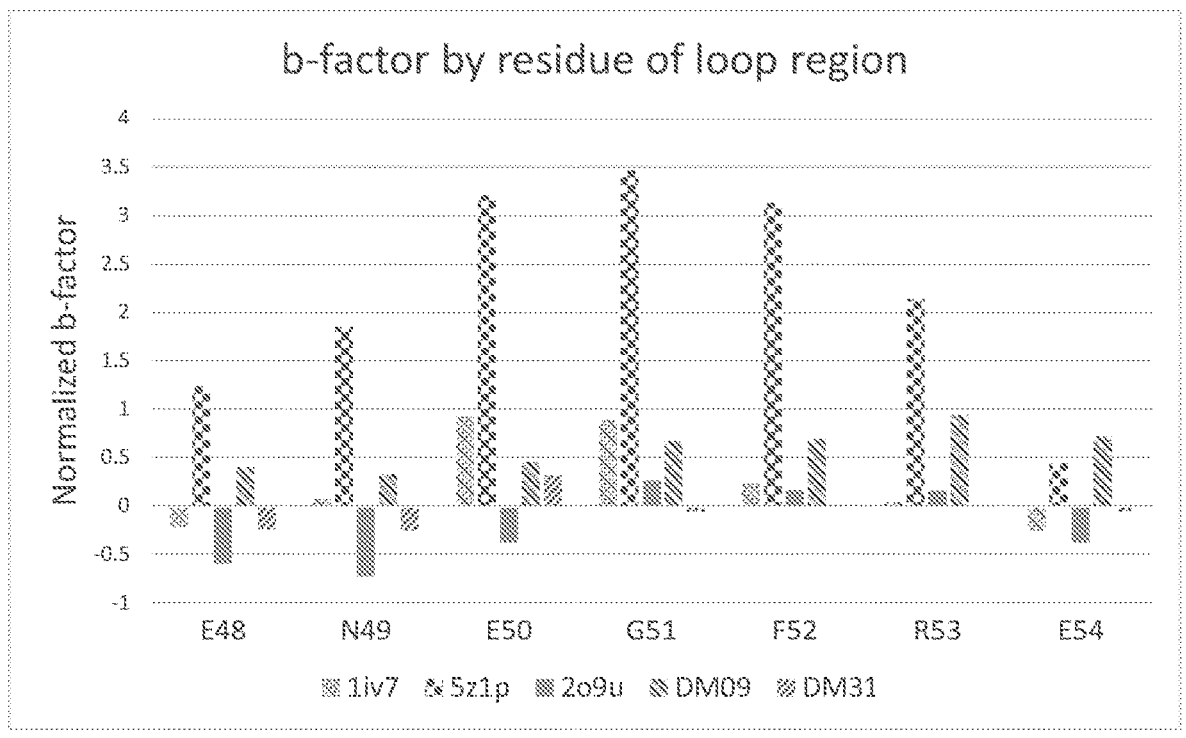

FIGS. 30-32 compare properties of DM31 to those of MNEI, using crystal structures available in the PDB and the crystal structure of DM31 solved by the inventors. These figures suggest that the substitutions, insertions and deletions, as well as the loop redesign, resulting in the new protein, DM31, made the protein more stable with significantly more rigid structural elements. Increased stability is suggested by the compact redesigned loop structure of DM31 as compared to MNEI's loop structures (FIG. 30B). In addition, the B-factor analyses shown in FIGS. 31A & 31B demonstrate reduced B-factors for loop residues of DM31 (FIG. 31B), as well as reduced averages for secondary structure elements (FIG. 31A). As B-factors indicate disorder, these results demonstrate the increased stability of DM31.

FIG. 32 shows backbone mediated hydrogen bonds in the redesigned loop and adjacent beta strands, demonstrating better optimized hydrogen bonds, as well as a new bond in this region of DM31 (FIG. 32C) as compared to the corresponding loop in MNEI (FIG. 32A, PDB ID: 2o9u). The new hydrogen bond denotes a stable beta turn, which replaces the disordered loop. Hydrogen bonds are also shown in Table 1B. This figure illustrates 19 hydrogen bonds that are present in DM31, and not present in at least one of the available MNEI structures. The numbers in the table indicate the distance of the participating hydrogen on the backbone nitrogen and the backbone oxygen as an acceptor. The table suggests that in the 2o9u structure, which is the highest resolution structure available for MNEI (resolution of 1.15A), there are less hydrogen bonds and some of these bonds are less optimized (in terms of distance and angle) compared to the DM31 crystal structure (resolution of 1.6 angstrom). Beyond the increase in B-factors that is described in FIG. 31, the 2o9u structure has three residues with double occupancies (E4, M42 and E48); highlighting the disorder in this high-resolution structure which was rigidified in the DM31 structure.

The inserts in FIG. 30A highlight selected amino acid substitutions as well as the redesigned loop region. These changes are the underpinnings of the increased stability and sweetness of the designer protein, DM31. The insert showing the loop region in FIG. 30A (also seen in FIG. 30B) illustrates that the residues in the loop area not only formed a novel hydrogen-bond (FIG. 32), but also participated in elongation of the two beta-strands nearby, also indicating increased stability. Overall, the replacement of the dirordered loop with a elongated beta strands linked by a beta turn rigidifies this region of the protein, resulting in increased stability, as shown a significant increase in the melting temperature.

TABLE 1B

Hydrogen bonds.

| # Hydrogen Bond | Donor | Acceptor | 1iv7 | 2O9U | DM31 |
|---|---|---|---|---|---|
| 1 | T45 N | N2 | 1.8 | — | 2.1 |
| 2 | E4 | K43 | 2.1 | 2, 2.5 | 2.1 |
| 3 | K43 | E4 | 1.8 | — | 1.8 |
| 4 | M42 | Q61 | 2.4 | 1.8, 2.3 | 2.1 |
| 5 | Q61 | M42 | 1.8 | — | 1.9 |
| 6 | I46 | G57 | 1.8 | — | 1.9 |
| 7 | G57 | I46 | 2.2 | 2.5 | — |
| 8 | E54 | E48 | — | — | 2.1 |
| 9 | E48 | E54 | 2 | 1.8 | 2 |
| 10 | Y58 | E77 | 1.8 | 2 | 1.8 |
| 11 | E77 | Y58 | 1.9 | — | 2 |
| 12 | E59 | K44 | 1.9 | — | 1.9 |
| 13 | K44 | E59 | 1.8 | 1.9 | 1.8 |
| 14 | F71 | V64 | 1.9 | 1.9 | 1.9 |
| 15 | V64 | F71 | 1.9 | — | 1.9 |
| 16 | D74 | R88 | 2.1 | — | 1.8 |
| 17 | R88 | D74 | 2.5 | 2.3 | 2.5 |
| 18 | N90 | R72 | 2.2 | 2 | 2 |
| 19 | R72 | N90 | 2 | — | 1.9 |

1-letter description of the amino acid followed by the number of the amino acid in the chain that is the donor or acceptor of the hydrogen bond.
Numbering is according to the numbering of MNEI (PDB ID: 2o9u).
All hydrogen bonds are between the hydrogen on the backbone nitrogen and the backbone oxygen as an acceptor.
The number denotes the angstrom distance is between the hydrogen of the donor and the acceptor.

B-factors (Debye-Waller Factors)

Debye Waller factors, also known as temperature-factors, B-factors, or atomic displacement parameters, are included for every atom in every X-ray structure deposited to the Protein Data Bank (PDB). These values are given for every protein atom and refer to the mean displacement of the atom as referred to from the experimental electron density map. Such distraction is the result of two different phenomena, dynamic disorder caused by the temperature-dependent vibration of the atoms, and static disorder.

To demonstrate the stability of the remodeled loop, the backbone B-factors of structures of MNEI (PDB IDs: 2O9U, 1IV7, 5Z1P) to the values of DM09 and DM31 were compared, based on the crystal structures prepared by the Structural Proteomic Center (Weizmann Institute of Science). For each protein, the backbone B-factor values were first normalized separately using Z-score normalization.

After normalization, it was evident that the loop design introduced to DM31 (deletion of 3 amino acids) decreased the B factors in the redesigned loop—both by removing positions with high B-factors, and by affecting neighborhood residues.

FIGS. 31A-B demonstrated the Normalized B-factors of MNEI structurers, DM09 & DM31. The backbone B-factors were first normalized for each structure separately using Z-score normalization. By region (A) and by loop residues (B).

Crystal Structure Quality Assurance Analysis

The software MolProbity preforms quality assurance analysis on the biophysical properties of protein structures. MolProbity was used to check MNEI structures and compare them to the crystal structures of DM09 and DM31. The comparison demonstrated that DM31 had favorable traits compared to the reference MNEI structures. Notably, DM31 has no poor rotamers, and over 96% of its rotamers are favored according to MolProbity. Another aspect that MolProbity examines are combinations of the backbone dihedral angles in relation to the known statistical distributions of these angles for different amino acids. With respect to these distributions, DM31 has no outlier angles and demonstrates over 97 percent of favorable values.

of new hydrogen bonds at the designer loop region, between E48 and E51 (equivalent to E54 in MNEI). This introduced bond, the result of a design which aimed at stabilizing the loop region, resulted in a classical rigid type-II beta-turn that is far more stable as than the random coil unstable loop found in the MNEI structures.

FIGS. 32A-C demonstrate the hydrogen bonds for MNEI (A), DM09(B) and DM31(C). The loop region is framed in squares.

FIG. 33 shows that the DM31 loop structure matches the structural definition of beta-turn: the structure of DM31 designed loop, and schematic beta-turn.

Example 2: Cloning, Expression, and Characterization of MNEI Designer Proteins DM13-DM33

Recombinant MNEI proteins were produced in *E. coli* BL21(DE3+) under a T7 promoter induced with Isopropyl β-D-1-thiogalactopyranoside (IPTG). Using this system, MNEI proteins were expressed as cytosolic protein (soluble fraction) in a high-density fermentation process. Designer MNEI (DM) are designed proteins with up to 11% amino acid substitutions. Two DM molecules were disclosed in WO2019215730 to the inventors of the present invention (DM08 and DM09). Both proteins contain three substitutions at positions 2, 23, and 65 of MNEI, leading to higher thermal stability and increased stability.

The present invention discloses novel DM molecules, which were produced to add up to three extra amino acid substitutions to either DM08 or DM09 at positions 35, 36, and 70, with or without reversing the replacements at positions 2 and 23. In addition, two unique DM molecules, in which four amino acids were removed from the loop connecting the monellin B and A chains, were produced (DM28 and DM29). Combining substitutions at positions 36 and 70 with the newly designed loop, three additional variants were then produced (DM31, DM32, and DM33). One additional variant was produced with only single amino acid substitution vs DM09 (DM30).

TABLE 1C

| | | | | | | | | Data of crystal structure analysis |
| Entity ID | Release Date | Resolution | Symmetry unit - Space Group | Clashscore, all atoms: | Poor rotamers | Favored rotamers | Ramachandran outliers | Ramachandran favored |
| --- | --- | --- | --- | --- | --- | --- | --- | --- |
| 1iv7 | 7 Oct. 2003 | 1.82 | P 1 2 2 | 16.69 | 4.76% | 84.52% | 0.00% | 97.34% |
| 5z1p | 21 Feb. 2018 | 1.89 | P 1 | 5.28 | 2.50% | 92.19% | 0.57% | 96.01% |
| 2o9u | 20 Feb. 2007 | 1.15 | P1 21 1 | 44.76 | 4.20% | 89.08% | 0.00% | 97.83% |
| DM09 | 6 Jul. 2021 | 1.5 | P 1 | 2.31 | 0.00% | 96.18% | 0.00% | 97.19% |
| DM31 | 13 Jul. 2021 | 1.6 | P 1 | 3.41 | 0.00% | 96.05% | 0.00% | 97.75% |

Hydrogen Bonds: Introducing a Beta-turn to the Loop Region

Proteins are stabilized by hydrogen bonds, which also determine their secondary structures. PyMol was used to analyze the hydrogen bonds of the crystal structures of DM31, DM09 and a representative high-quality MNEI structure, PDB id 2O9U. The Analysis revealed the presence All DMs were produced in *E. coli* fermentation and purified to a level of >95%.

Cloning

Site-directed mutagenesis (SDM), based on the sequences of DM08 and DM09, was used for creating DM13-DM33. For the loop removal in DM28-33, deletions were made in a similar way. Table 2 lists the primers used for this process. All final constructs sequences were confirmed.

TABLE 2

| Primer target | Name (F/R) (SEQ ID NO): | Sequence | Tm |
|---|---|---|---|
| DM13 | DM13_F (SEQ ID NO: 28) | AAGCGATAAAatcTTTCGTGCAGATATTAG | 60° C. |
| | DM13 R (SEQ ID NO: 29) | GCTTTCACATACAGCTGATATTC | 62° C. |
| DM14 | DM14_F (SEQ ID NO: 30) | AAGCGATAAAatcTTTCGTGCAGATATTAGCG | 64° C. |
| | DM14 R (SEQ ID NO: 31) | GCGCGCACATACAGCTGA | 69° C. |
| DM15/ DM20/ DM22 | DM15_F (SEQ ID NO: 32) | AGTTGACGAAgaaAACAAAATTGG | 56° C. |
| | DM15_R (SEQ ID NO: 33) | GCAAATTTACCCAGGTTC | 58° C. |
| DM16- 18 | SDM_K36T_F (SEQ ID NO: 34) | ACCTTTAACACCGTTATTCGTCCGTGCATG | 63° C. |
| | SDM_K36T_R (SEQ ID NO: 35) | CAGACGACCATACTGGCC | 65° C. |
| DM19 | DM19_F (SEQ ID NO: 36) | CTGACCTTTACCACCGTTATTCG | 60° C. |
| | DM19 R (SEQ ID NO: 37) | ACGACCATACTGGCCAAT | 64° C. |
| DM21/ DM23 | DM21_F (SEQ ID NO: 38) | TACCATGGGCgaaTGGGAGATTA | 63° C. |
| | DM21_R (SEQ ID NO: 39) | TATCTCCTTCTTAAAGTTAAACAAAATTATTTC | 61° C. |
| DM24 | DM24_F (SEQ ID NO: 40) | GACCTTTACCaaaGTTATTCGTCCGTGCATG | 63° C. |
| | DM24_R (SEQ ID NO: 41) | AGACGACCATACTGGCCA | 66° C. |
| DM25 | DM25_F (SEQ ID NO: 42) | AGTTGACGAAattAACAAAATTGGCC | 55° C. |
| | DM25 R (SEQ ID NO: 43) | GCAAATTTACCCAGGTTC | 58° C. |
| DM26 | Y65R_F (SEQ ID NO: 44) | GCTGTATGTGcgcGCAAGCGATAAAC | 62° C. |
| | Y65R_R (SEQ ID NO: 46) | TGATATTCATAGCCTTTAATCTC | 58° C. |
| DM27 | DM27_F (SEQ ID NO: 47) | GTTGACGAAGtGAACAAAATTG | 57° C. |
| | DM27_R (SEQ ID NO: 48) | TGCAAATTTACCCAGGTTC | 60° C. |
| DM28/ DM29/ DM31- 33 | Loop1_F (SEQ ID NO: 49) | GCGAGATTAAAGGCTATG | 58° C. |
| | Loop1_R (SEQ ID NO: 50) | CATTTTCATAGATGGTTTTTTTC | 55° C. |
| DM30 | L70I_F (SEQ ID NO: 51) | CAAGCGATAAAatcTTTCGTGCAG | 62° C. |
| | L70I_R (SEQ ID NO: 52) | CGCGCACATACAGCTGA | 55° C. |

The nucleotide sequences of DM13-DM33 and DM-3, 8-12 are listed in Table 3.

TABLE 3

Sequences of the modified proteins

| SEQ ID NO: | Sequence |
| --- | --- |
| SEQ ID NO: 1 (DM13) | GNWEIIDIGPFTQNLGKFAVDEVNKIGQYG RLTFNKVIRPCMKKTIYENEGFREIKGYEY QLYVKASDKIFRADISEDYKTRGRKLLRFN GPVPPP |
| SEQ ID NO: 2 (DM14) | GNWEIIDIGPFTQNLGKFAVDEANKIGQYG RLTENKVIRPCMKKTIYENEGFREIKGYEY QLYVRASDKIFRADISEDYKTRGRKLLRFN GPVPPP |
| SEQ ID NO: 3 (DM15) | GNWEIIDIGPFTQNLGKFAVDEENKIGQYG RLTFNKVIRPCMKKTIYENEGFREIKGYEY QLYVKASDKIFRADISEDYKTRGRKLLRFN GPVPPP |
| SEQ ID NO: 4 (DM016) | GNWEIIDIGPFTQNLGKFAVDEVNKIGQYG RLTENTVIRPCMKKTIYENEGFREIKGYEY QLYVKASDKIFRADISEDYKTRGRKLLRFN GPVPPP |
| SEQ ID NO: 5 (DM17) | GNWEIIDIGPFTQNLGKFAVDEANKIGQYG RLTFNTVIRPCMKKTIYENEGFREIKGYEY QLYVRASDKIFRADISEDYKTRGRKLLRFN GPVPPP |
| SEQ ID NO: 6 (DM18) | GNWEIIDIGPFTQNLGKFAVDEENKIGQYG RLTFNTVIRPCMKKTIYENEGFREIKGYEY QLYVKASDKIFRADISEDYKTRGRKLLRFN GPVPPP |
| SEQ ID NO: 7 (DM19) | GNWEIIDIGPFTQNLGKFAVDEANKIGQYG RLTFTTVIRPCMKKTIYENEGFREIKGYEY QLYVRASDKIFRADISEDYKTRGRKLLRFN GPVPPP |
| SEQ ID NO: 8 (DM20) | GNWEIIDIGPFTQNLGKFAVDEENKIGQYG RLTFTTVIRPCMKKTIYENEGFREIKGYEY QLYVRASDKIFRADISEDYKTRGRKLLRFN GPVPPP |
| SEQ ID NO: 9 (DM21) | GEWEIIDIGPFTQNLGKFAVDEENKIGQYG RLTFTTVIRPCMKKTIYENEGFREIKGYEY QLYVRASDKIFRADISEDYKTRGRKLLRFN GPVPPP |
| SEQ ID NO: 10 (DM22) | GNWEIIDIGPFTQNLGKFAVDEENKIGQYG RLTFNTVIRPCMKKTIYENEGFREIKGYEY QLYVRASDKIFRADISEDYKTRGRKLLRFN GPVPPP |
| SEQ ID NO: 11 (DM23) | GEWEIIDIGPFTQNLGKFAVDEENKIGQYG RLTFNTVIRPCMKKTIYENEGFREIKGYEY QLYVRASDKIFRADISEDYKTRGRKLLRFN GPVPPP |
| SEQ ID NO: 12 (DM24) | GNWEIIDIGPFTQNLGKFAVDEANKIGQYG RLTFTKVIRPCMKKTIYENEGFREIKGYEY QLYVRASDKIFRADISEDYKTRGRKLLRFN GPVPPP |
| SEQ ID NO: 13 (DM25) | GNWEIIDIGPFTQNLGKFAVDEINKIGQYG RLTFNKVIRPCMKKTIYENEGFREIKGYEY QLYVRASDKLFRADISEDYKTRGRKLLRFN GPVPPP |
| SEQ ID NO: 14 (DM26) | GEWEIIDIGPFTQNLGKFAVDEENKIGQYG RLTFNKVIRPCMKKTIYENEGFREIKGYEY QLYVRASDKIFRADISEDYKTRGRKLLRFN GPVPPP |

TABLE 3-continued

Sequences of the modified proteins

| SEQ ID NO: | Sequence |
| --- | --- |
| SEQ ID NO: 15 (DM27) | GNWEIIDIGPFTQNLGKFAVDEVNKIGQYG RLTENKVIRPCMKKTIYENEGFREIKGYEY QLYVRASDKLFRADISEDYKTRGRKLLRFN GPVPPP |
| SEQ ID NO: 16 (DM28) | GNWEIIDIGPFTQNLGKFAVDEANKIGQYG RLTENKVIRPCMKKTIYENGEIKGYEYQLY VRASDKLFRADISEDYKTRGRKLLRFNGPV PPP |
| SEQ ID NO: 17 (DM29) | GEWEIIDIGPFTQNLGKFAVDEENKIGQYG RLTFNKVIRPCMKKTIYENGEIKGYEYQLY VYASDKLFRADISEDYKTRGRKLLRFNGPV PPP |
| SEQ ID NO: 18 (DM30) | GNWEIIDIGPFTQNLGKFAVDEINKIGQYG RLTFNKVIRPCMKKTIYENEGFREIKGYEY QLYVRASDKIFRADISEDYKTRGRKLLRFN GPVPPP |
| SEQ ID NO: 19 (DM31) | GNWEIIDIGPFTQNLGKFAVDEANKIGQYG RLTENKVIRPCMKKTIYENGEIKGYEYQLY VRASDKIFRADISEDYKTRGRKLLRFNGPV PPP |
| SEQ ID NO: 20 (DM32) | GNWEIIDIGPFTQNLGKFAVDEVNKIGQYG RLTFNKVIRPCMKKTIYENGEIKGYEYQLY VKASDKIFRADISEDYKTRGRKLLRFNGPV PPP |
| SEQ ID NO: 21 (DM33) | GNWEIIDIGPFTQNLGKFAVDEVNKIGQYG RLTENTVIRPCMKKTIYENGEIKGYEYQLY VKASDKIFRADISEDYKTRGRKLLRFNGPV PPP |
| SEQ ID NO: 45 (MNEI) | GEWEIIDIGPFTQNLGKFAVDEENKIGQYG RLTFNKVIRPCMKKTIYENEGFREIKGYEY QLYVYASDKLFRADISEDYKTRGRKLLRFN GPVPPP |
| SEQ ID NO: 22 (DM03) | GNWEIIDTGPFTQKLGKFAVDEANKIGKYG TLTFTKVIRPTMKKTIYENEGFREIKGYEY QLYVKANDKLFRADISEDYKTRGLKLLRFN GPVPPP |
| SEQ ID NO: 23 (DM08) | GNWEIIDIGPFTQNLGKFAVDEVNKIGQYG RLTFNKVIRPCMKKTIYENEGFREIKGYEY QLYVKASDKLFRADISEDYKTRGRKLLRFN GPVPPP |
| SEQ ID NO: 24 (DM09) | GNWEIIDIGPFTQNLGKFAVDEANKIGQYG RLTFNKVIRPCMKKTIYENEGFREIKGYEY QLYVRASDKLFRADISEDYKTRGRKLLRFN GPVPPP |
| SEQ ID NO: 25 (DM10) | GEWEIIDIGPFTQNLGKFAVDEENKIGKYG TLTFTKVIRPCMKKTIYENEGFREIKGYEY QLYVYANDKLFRADISEDYKTRGRKLLRFN GPVPPP |
| SEQ ID NO: 26 (DM11) | GEWEIIDTGPFTQKLGKFAVDEENKIGQYG RLTFNKVIRPTMKKTIYENEGFREIKGYEY QLYVYASDKLFRADISEDYKTRGLKLLRFN GPVPPP |
| SEQ ID NO: 27 (DM12) | GEWEIIDTGPFTQNLGKFAVDEENKIGQYG RLTFNKVIRPTMKKTIYENEGFREIKGYEY QLYVYASDKLFRADISEDYKTRGLKLLRFN GPVPPP |

Fermentation

All DM clones were subjected to fermentation in 3 L vessels using the Sartorius BioStatB system or 2 L vessels of Solaris Jupiter system. Some DM clones were produced by outsourcing at VTT (Finland) and SciVac (Israel) All fermentations followed a protocol based on "High cell-density fermentation of *Escherichia coli*" by Arie Geerlof-EMBL Hamburg 29 Jan. 2008.

Purification

All DM samples were purified using the following steps:
1. Lysis by pressure homogenizer.
2. Capture of the protein on a multimode resin, elution with increasing NaCl concentration in the same buffer.
3. At least one polishing step using resins from the following groups:
   1. Ion exchange.
   2. Hydrophobic interaction.
   3. Size exclusion.
4. Final microbial filtration (0.2 um) and storage at −20° C.

Characterization

Purification Level

Purification level was evaluated using gel electrophoresis followed by Coomassie staining and densitometry analysis. Analysis by densitometry was conducted by running 20 μg/lane of each protein, using a BSA standard curve of 50-500 ng/lane. In all samples, maximal contamination reached 3% (i.e., 97% purity).

Sweetness Evaluation

A professional sensory panel includes panelists who were calibrated first with sugar solutions on a scale of 0-100 (magnitude estimation), with 0=not sweet at all and 100=very sweet. After calibration, tasters graded the tested samples on the same scale according to the validated tasting protocol. Linear scale for sucrose was obtained in concentrations of 2° Bx, 4° Bx, 6° Bx, and 8° Bx.

Brix(Bx)=gr/100 ml.

Initial sweetness evaluation was conducted by comparing to sugar at 6° Bx, DM09, and the new selected DMs in each test, at a selected potency X4000. All dilutions were done in water only. Samples were evaluated by an expert panel on different occasions, using 6° Bx sucrose and DM09 as controls (FIG. 1).

DSF and DSC Analysis—Heat Sensitivity

Relative Tm was determined by Differential Scanning Fluorimetry (DSF) using Nanotemper Prometheus. DSF is a method for easy, rapid, and accurate analysis of protein stability and aggregation. DSF detects changes in the fluorescence of tryptophan and tyrosine residues in the protein. The fluorescence of tryptophan and tyrosine residues is strongly dependent on their close surroundings. A change in protein conformation will be reflected as a fluorescence change. The 1$^{st}$ derivate of the fluorescence ratio (330/350) is used to determine the inflection point. Since no secondary reporter fluorophores are required, protein solutions can be analyzed independently of buffer compositions and over a concentration range of 250 mg/ml down to 10 μg/ml. DM13-33 were analyzed at a concentration of 0.5 mg/ml in a 10 mM phosphate buffer pH 7.

Table 4 summarizes the properties of the modifying proteins DM13-DM33. The results indicate the role of several amino acids in controlling protein sweetness and thermal stability. Besides E2, E23, and Y65, substituting Leucine at position 70 with Isoleucine increased the Tm by 2° C. Stability was further increased by substituting Lysine at position 36 with Threonine, however, this substitution also caused a reduction of protein sweetness. Loop design resulting in a 4 amino acids loop led to increased stability, expressed in increase of Tm of about 7-10° C.

TABLE 4

Summary of the properties of the modifying proteins DM13-DM33: Tm (° C.) Structural thermal stability is estimated according to the inflection point, determined by Differential Scanning Fluorimetry (DSF). Sweetness level was evaluated at 6° Bx sucrose equivalent based on the potency of 1:4000, diluted in water, compared to DM09.

| | E2 | E23 | N35 | K36 | Y65 | L70 | Loop | Tm | Sweet intensity vs. DM09 (1:4000) |
|---|---|---|---|---|---|---|---|---|---|
| MNEI | — | — | — | — | — | — | | 71.5 | 32.5 |
| DM09 | N | A | — | — | R | — | | 82.6 | 75.9 |
| DM13 | N | V | — | — | K | I | | 84.6 | 77.7 |
| DM14 | N | A | — | — | R | I | | 84.1 | 72.9 |
| DM15 | N | — | — | — | K | I | | 74.2 | 83.1 |
| DM16 | N | V | — | T | K | I | | 86.2 | 23.3 |
| DM17 | N | A | — | T | R | I | | 86 | 21.7 |
| DM18 | N | — | — | T | K | I | | 75.3 | 28.8 |
| DM19 | N | A | T | T | R | I | | 85 | 17.3 |
| DM20 | N | — | T | T | R | I | | 79.9 | 34.6 |
| DM21 | — | — | T | T | R | I | | 65.4 | 18.3 |
| DM22 | N | — | — | T | R | I | | 73 | 52.8 |
| DM23 | — | — | — | T | R | I | | 73.2 | 21.1 |
| DM24 | N | A | T | — | R | I | | 82.6 | 81.5 |
| DM25 | N | I | — | — | R | — | | | 66.1 |
| DM26 | — | — | — | — | K | I | | | |
| DM27 | N | V | — | — | R | — | | 80.1 | 72.2 |
| DM28 | N | A | — | — | R | — | 4mer | 91 | 76.9 |
| DM29 | — | — | — | — | — | — | 4mer | | — |
| DM30 | N | I | — | — | R | I | | 82.4 | 79.6 |
| DM31 | N | A | — | — | R | I | 4mer | | 74.6 |
| DM32 | N | V | — | — | K | I | 4mer | | 75.0 |
| DM33 | N | V | — | T | K | I | 4mer | | — |

Conclusions: The Effect of Specific Positions on Tm and Sweetness Level

E2—substitution with N=>increase in Tm and sweetness (comparison of DM22 to DM23 or DM20 to DM21).

E23—substitution with A or V=>increase in Tm (comparison of DM13 to DM15 or DM17 to DM22). No clear effect on sweetness (on the background of other substitutions)

E23—substitution with A Vs. V=>(comparison of DM09 to DM27).

E23—substitution with I:=>increase in Tm (comparison of DM13 to DM15 or DM17 to DM22). No clear effect on sweetness.

N35—substitution with T=>no clear effect on either parameter.

K36—substitution T=>increase in Tm, strong reduction in sweetness (comparison of DM14 to DM17, DM24 to DM14, DM13 to DM16)

Y65—substitution with R Vs. K=>(comparison of DM08 to DM27)

L70—substitution with I=>small increase in Tm, no clear effect on sweetness (comparison of DM09 to DM14, or DM08 to DM13).

Loop design—deletion of E50, F52, R53=>large increase in Tm, no clear effect or sweetness Example 3: Sensory Evaluation of Sweet Taste Intensity and Stability for Monellin Designer Protein DM13

Figure 2A:
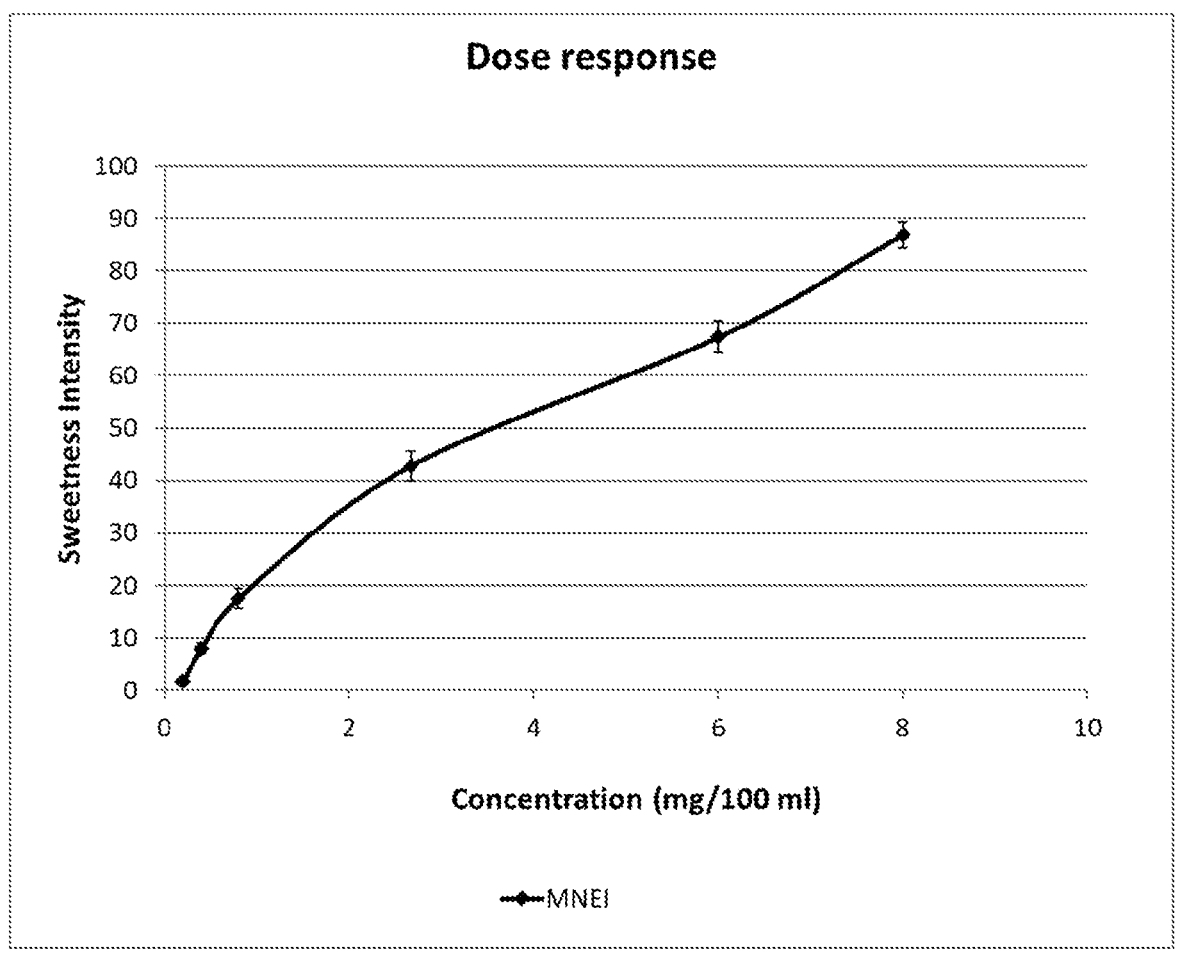
FIGS. 2A-2D are graphs showing a dose-response of sweetness intensity of MNEI (FIG. 2A), DM13 (FIG. 2B), DM28 (FIG. 2C), and DM31(FIG. 2D).
Figure 2B:
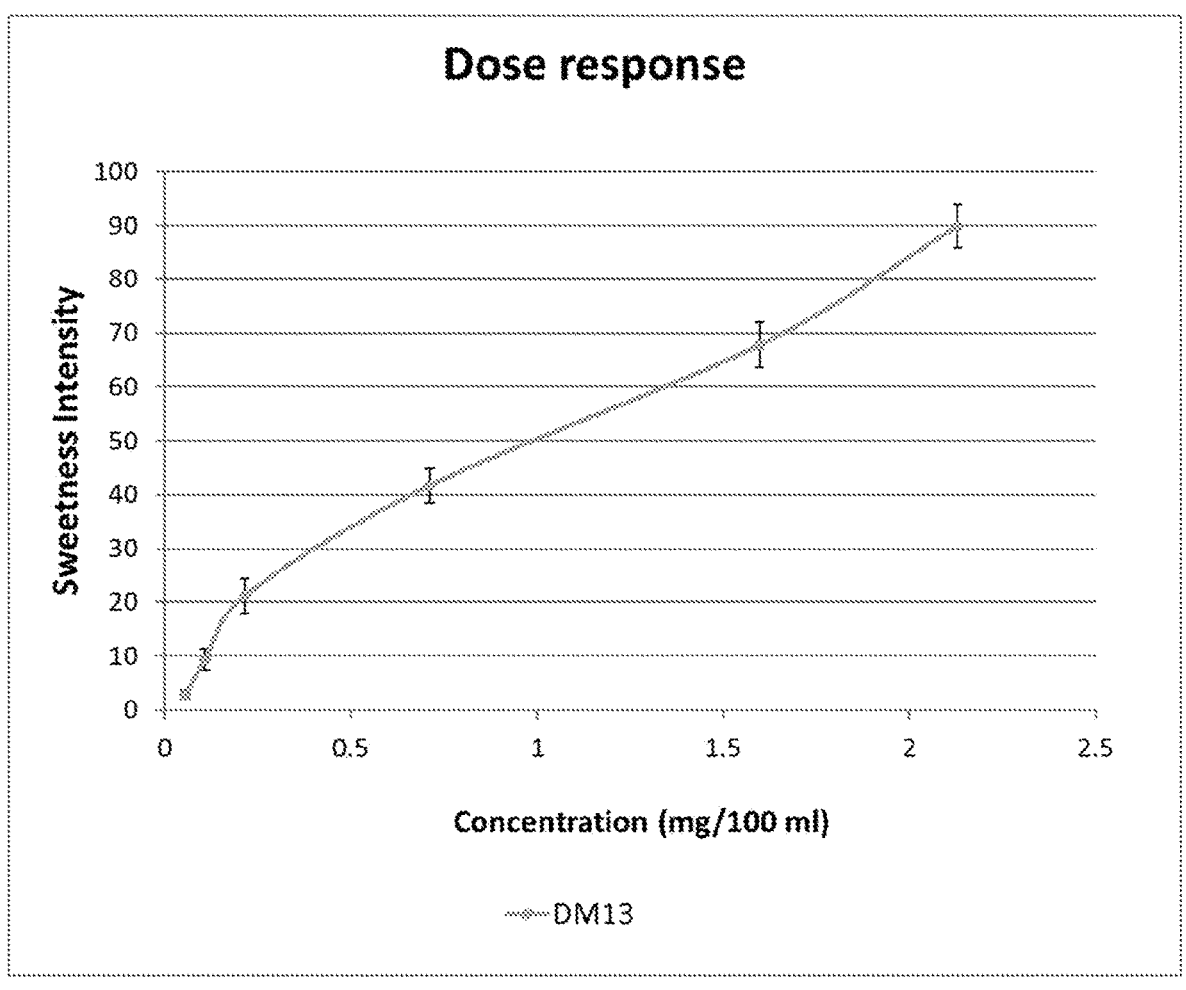
Figure 2C:
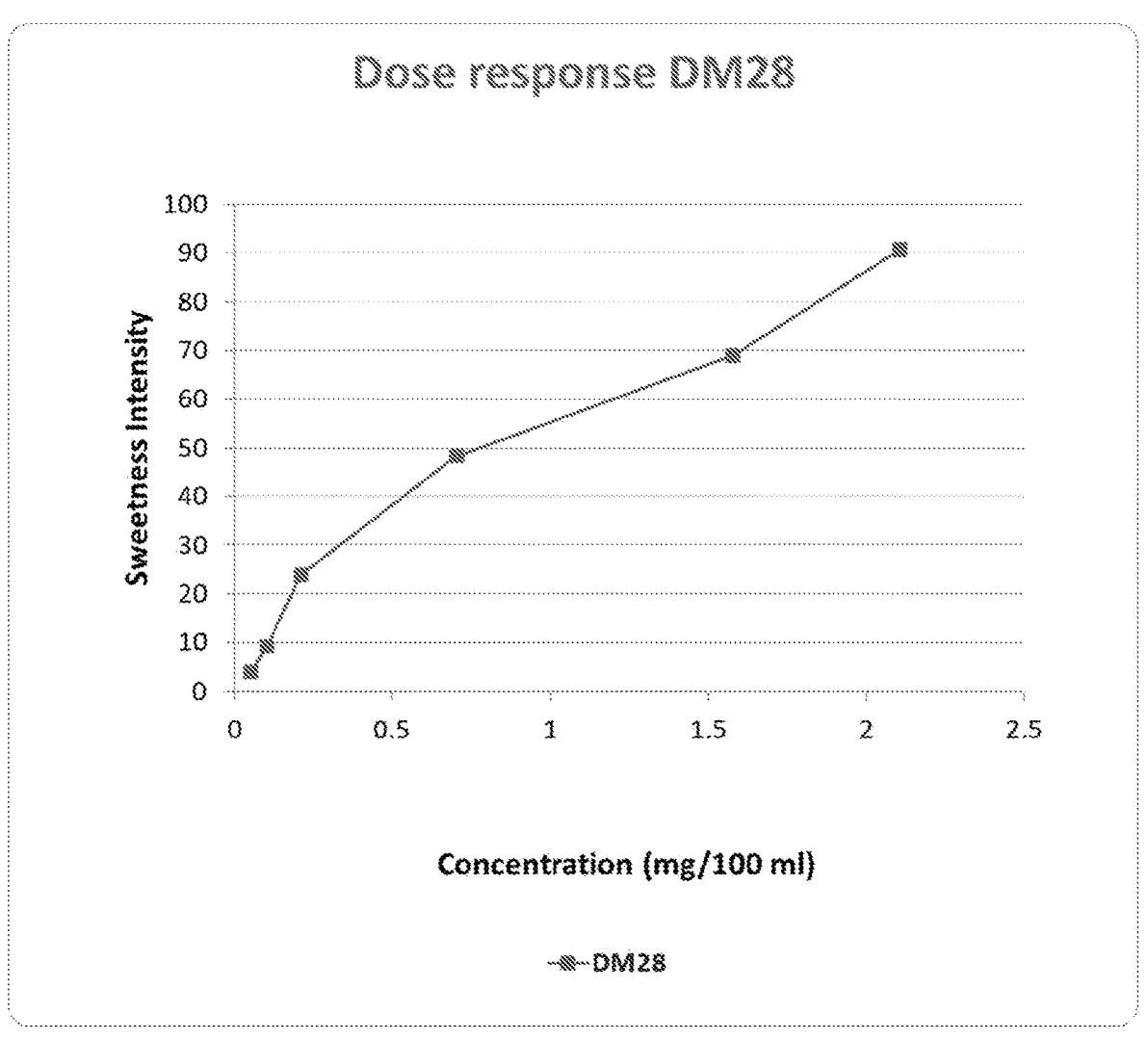
Figure 2D:
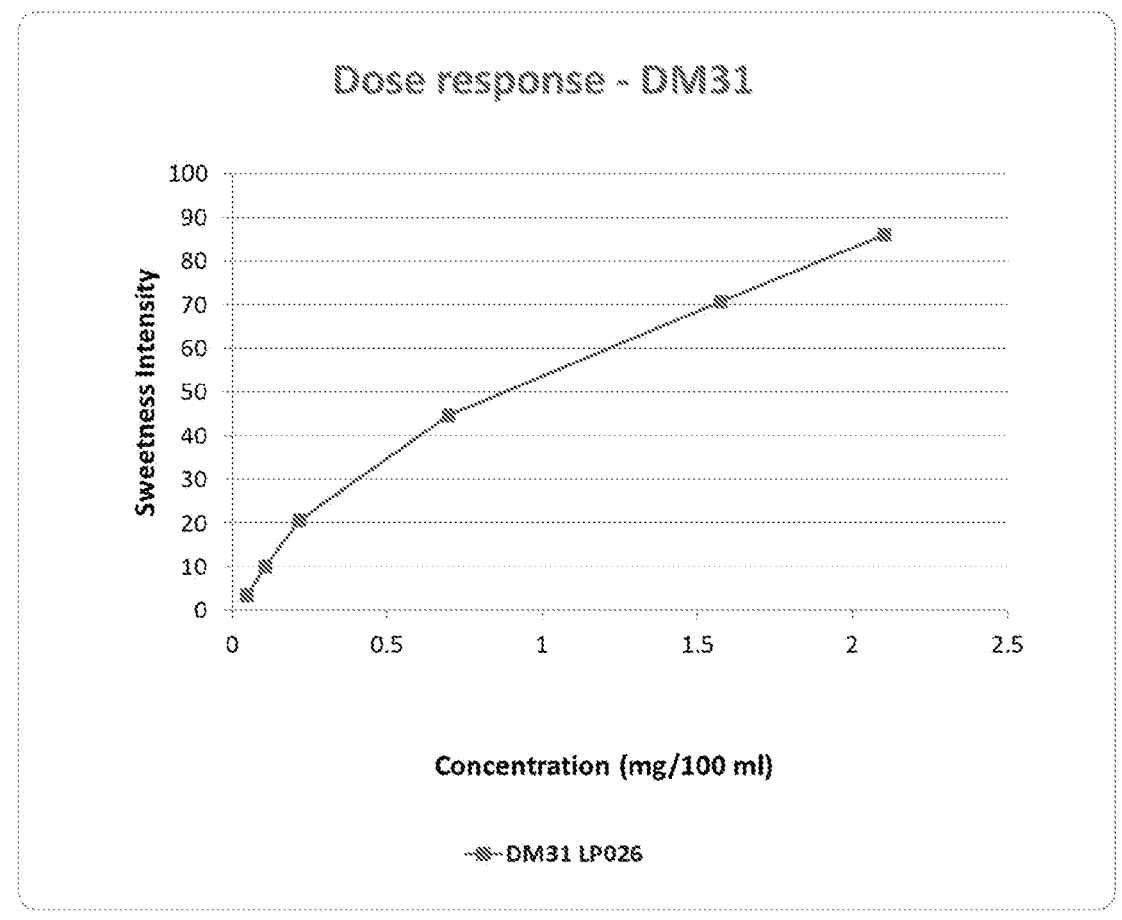

A dose response of sweetness intensity of DM13 (FIG. 2B), DM28 (FIG. 2C) and DM31 (FIG. 2D) compared to MNEI (FIG. 2A) was conducted. Panelists were first calibrated with sugar solutions on a scale of 0-100 (magnitude estimation), while 0=not sweet at all and 100=very sweet. A linear scale for sucrose was obtained in concentrations of 2° Bx, 4° Bx, 6° Bx, and 8° Bx. Brix (Bx)=gr/100 ml. After calibration, the tasters graded the tested samples at increasing concentrations on the same scale according to the validated tasting protocol.

As demonstrated by FIG. 2, DM13, DM28 and DM31 are four times sweeter than MNEI.

Heat Treatment in Buffer Citrate at 95° C. for 30 Sec

Buffer citrate (pH=3) was preheated in the thermomix to 95° C. At 95° C., DM13 (at a concentration of 5° Bx iso-sweet) was added to the buffer solution and kept at this temperature for 30 seconds. After 30 seconds, the solution was immediately cooled down in the freezer.

Figure 4:
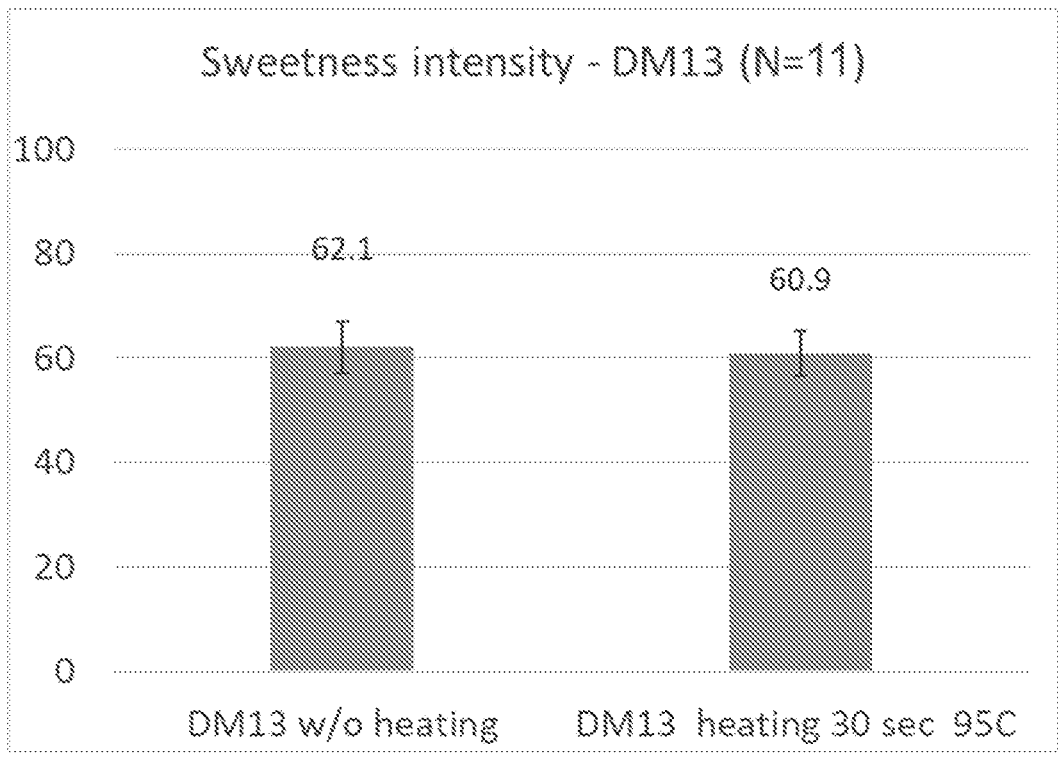
FIG. 4 is a histogram showing the stability of DM13 in a citrate buffer after heating to 95° C. for 30 seconds. Y-axis is sweetness intensity.

The expert panel (n=15) tasted the products and evaluated the sweetness intensity on a scale of 0-100. Each treated product was tasted compared to the reference (same solution without heating). All products were served in code numbers. As shown in FIG. 4, DM13 is stable in buffer citrate at 95° C. for 30 seconds.

Heat Treatment in Buffer Citrate at 90° C. for 10 Min

Buffer citrate (pH3) was preheated at the thermomix to 90° C. At 90° C., DM13 (at a concentration of 5° Bx iso-sweet) was added to the buffer solution and kept at this temperature for 1 min, 3 min, and 10 min accordingly.

After the relevant time, the solution was immediately cooled down in the freezer.

Figure 3:
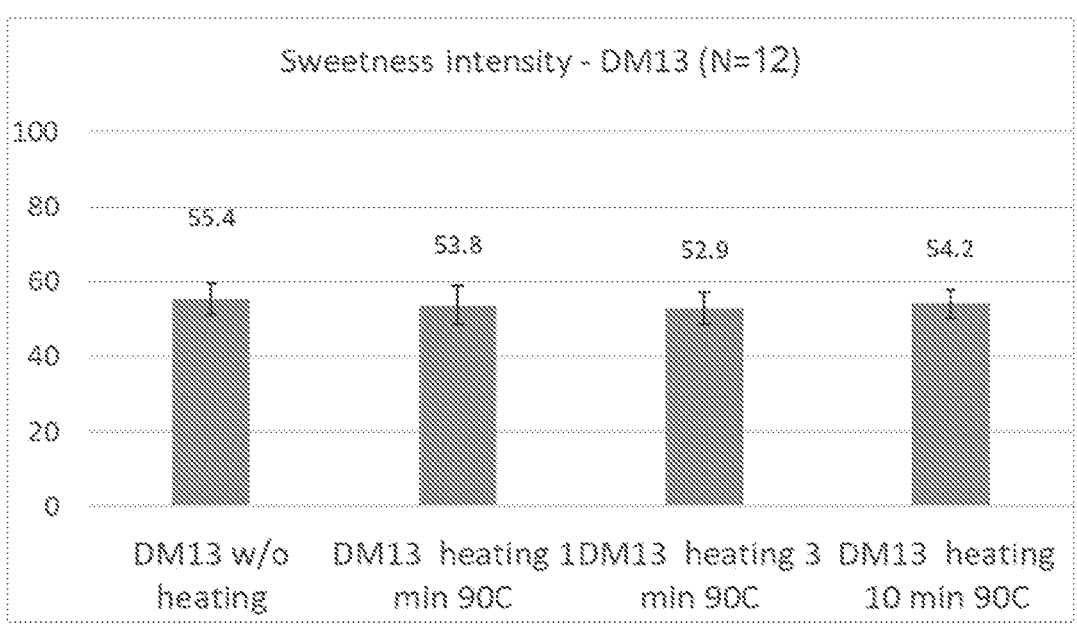
FIG. 3 is a histogram showing the stability of DM13 in a citrate buffer after heating to 90° C. up to 10 minutes. Y-axis is sweetness intensity.

The expert panel tasted the products and evaluated the sweetness intensity on a scale of 0-100. The treated products were tasted compared to the reference (same solution without heating). All products were served in code numbers. As shown in FIG. 3, DM13 is stable in buffer citrate at 90° C. for 10 minutes.

DM13 Sweetness Stability after 8 weeks at 21° C. and 32° C.

Shelf-life stability of DM13 was tested for 4 weeks and 8 weeks, at 21° C. and 32° C., in buffer citrate (0.113% citric acid, 0.016% tri-sodium citrate, 99.9% water). DM13 was added at 5 Brix equivalents (potency 1:4000).

Figure 5A:
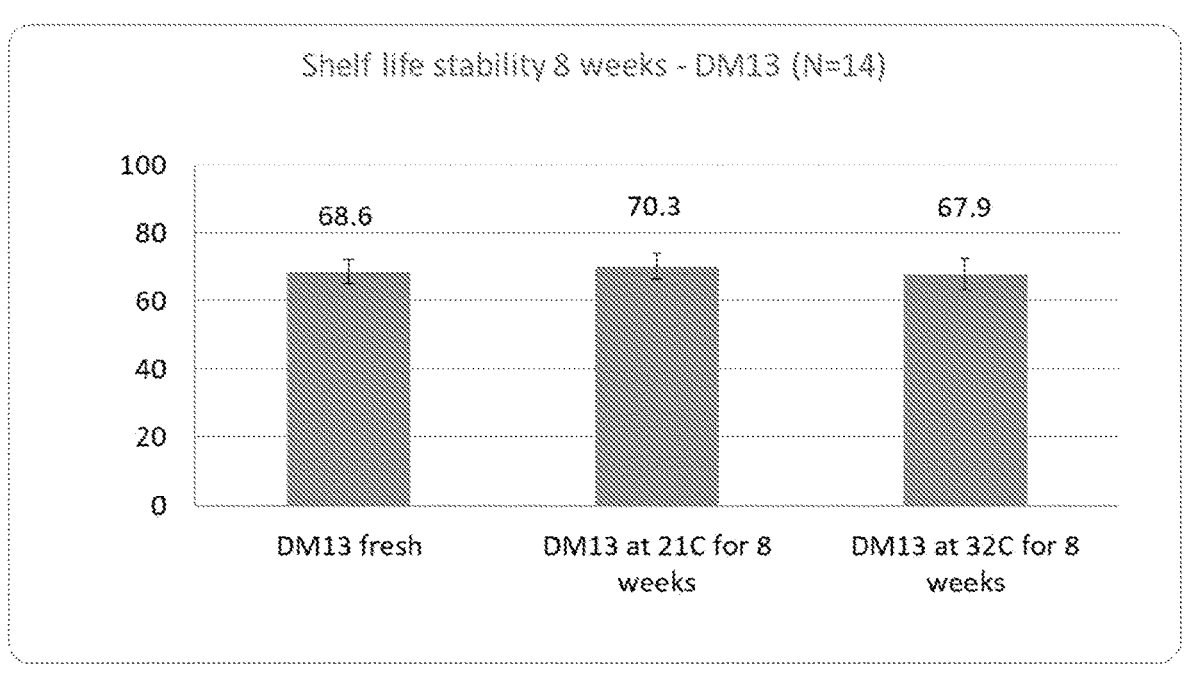
FIGS. 5A-5B are histograms showing the stability of DM13 after 8 weeks stored at 21° C. and 32° C. Y-axis is sweetness intensity.
Figure 5B:
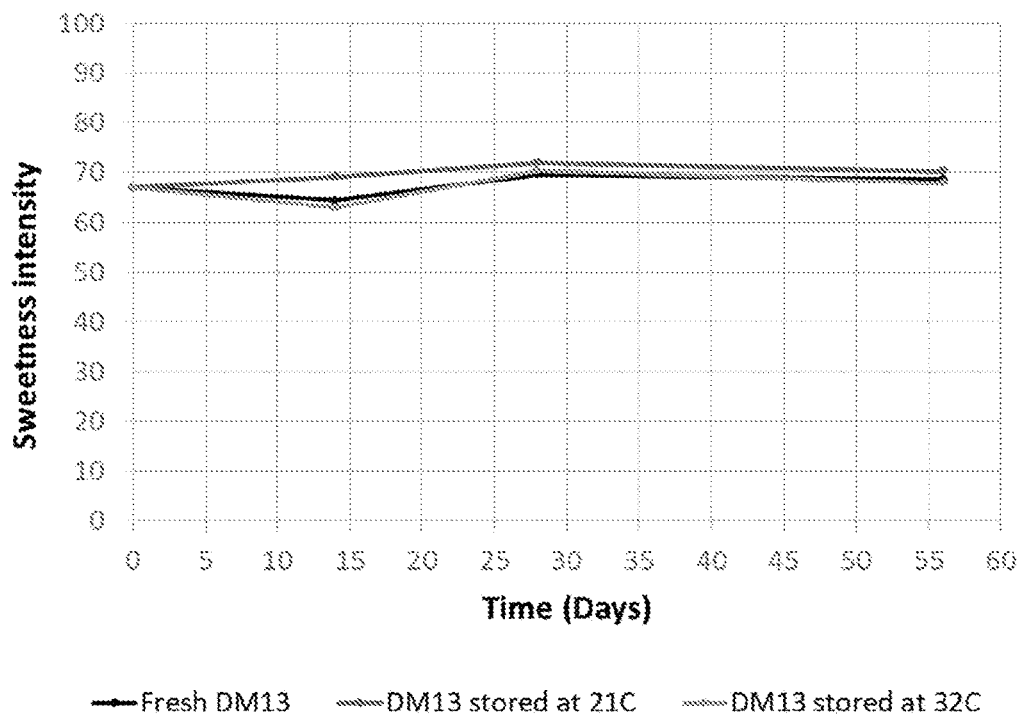

The treated products were tasted by the expert panel and compared to a fresh solution. As shown in FIG. 5A-B, DM13 is stable at both temperatures for 8 weeks.

Example 4: Ketchup and Plain Yogurt Formulations with Designer-MNEI (DM) Proteins Formulations of Ketchup with DM proteins are presented in Table 5.

TABLE 5

DM09, DM28 and DM31 based ketchup formulation
(69% added sugar reduction compared to regular ketchup)

| Ingredients [%] | With DM09 | With DM28 | With DM31 |
|---|---|---|---|
| Water (Solvent) | 34.6 | 34.8 | 34.3 |
| Tomato concentrate [22° Bx] (Base ingredient) | 48 | 48 | 48 |
| sugar bulk (sweetener & bulking agent) | 4 | 4 | 4 |
| DM09 (5.14 mg/ml)/ DM28 (9.6 mg/ml)/ DM31 (3.62 mg/ml)* | 0.614 | 0.378 | 0.871 |
| Inulin (orafti HIS) (Bulking agent) | 7 | 7 | 7 |
| Vinegar (Flavor) | 4.5 | 4.5 | 4.5 |
| Salt (Flavor) | 1 | 1 | 1 |

TABLE 5-continued

DM09, DM28 and DM31 based ketchup formulation
(69% added sugar reduction compared to regular ketchup)

| Ingredients [%] | With DM09 | With DM28 | With DM31 |
|---|---|---|---|
| Spices (kit for ketchup) (Flavor) | 0.04 | 0.04 | 0.04 |
| Xanthan (thickener) | 0.25 | 0.25 | 0.25 |

*Changes according to the protein solution concentration

Formulations of Yogurt with DM proteins are presented in Table 6.

TABLE 6

DM09, DM28 and DM31 based yogurt
(33% added sugar reduction compared to regular full sugar yogurt)

| | | Weight | | | % Sugar reduction |
|---|---|---|---|---|---|
| Full sugar | | | | | |
| Yogurt | 3% fat, | 100 | gr | 90% | 0% |
| Strawberry puree | Boiron, | 6.7 | gr | 6% | |
| Sucrose | Sugar | 5 | gr | 4% | |
| | | 111.7 | | 100% | |
| DM09 (−33%) | | | | | |
| Yogurt | 3% fat, | 100 | gr | 91% | 33% |
| Strawberry puree | Boiron, | 6.7 | gr | 6% | |
| Sucrose | Sugar | 3.3 | gr | 3% | |
| DM09 | (5.14 mg/ml) | 0.376 | ml | 0.3% | |
| | | 110.4 | | 100% | |
| DM28 (−33%) | | | | | |
| Yogurt | 3% fat, | 100 | gr | 91% | 33% |
| Strawberry puree | Boiron, | 6.7 | gr | 6% | |
| Sucrose | Sugar | 3.3 | gr | 3% | |
| DM28 | (9.6 mg/ml) | 0.231 | ml | 0.2% | |
| | | 110.2 | | 100% | |
| DM31 (−33%) | | | | | |
| Yogurt | 3% fat, | 100 | gr | 91% | 33% |
| Strawberry puree | Boiron, | 6.7 | gr | 6% | |
| Sucrose | Sugar | 3.3 | gr | 3% | |
| DM31 | (3.62 mg/ml) | 0.53 | ml | 0.5% | |
| | | 110.5 | | 100% | |

Testing Methods—Taste Proteins' Expert Panel

All sensory evaluations were determined using a trained expert panel for analytical discrimination. The sensory expert panel was established by a screening process of potential tasters. Screening tests, conducted according to ISO standard (IS 8586-1), examined the sensory sensitivity, consistency, and sensory memory of the taster. The panel is well trained and calibrated. The selected panel is trained regularly to maintain high performance output.

Sensory Profiles for Ketchup and Plain Yogurt Prototypes—Testing Procedure

For each category (Ketchup/plain yogurt), a sensory vocabulary was determined by the expert panel. The sensory vocabulary was built by tasting a large range of products from the category and raising all the relevant sensory attributes which describes the category. Using as diverse a language as possible to best describe the products.

After having the sensory vocabulary, selecting the key attributes that will be used to describe the products in the questionnaire.

Building sensory profiles for ketchup and for plain yogurt: the panelists rated each tested product versus a reference on a two-way scale (between −3 to +3) with a fixed reference point (0) across all the attributes selected from the glossary. When the tested product was evaluated "more" than the reference on a specific attribute (e.g., sweeter, thicker, and so on), it got positive rates (+1, +2, or +3), and when it was rated "less" than the reference on a specific attribute (e.g., less sweet, less thick, and so on) it got negative rates (−1, −2 or −3). Before and between attributes, the tasters were requested to rinse their mouths with mineral water, eat an unsalted cracker and cucumber, and drink water again.

Results

Ketchup Prototype

Figure 6:
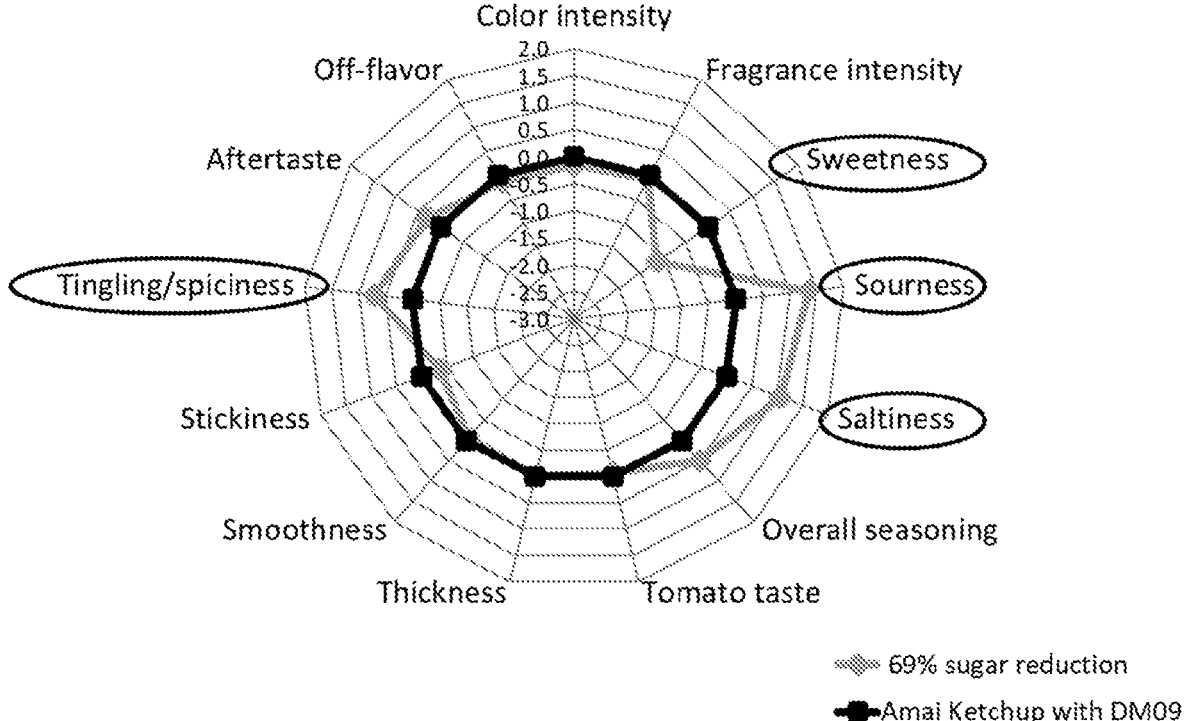
FIG. 6 is a spider graph showing properties of a control ketchup prototype with a 69% reduction of added sugar and of an exemplary ketchup with DM09, the results showing that the control ketchup is less sweet, sourer, saltier, and has more tongue tingling compared to the ketchup with DM09.

As demonstrated in FIG. 6, a ketchup prototype with a 69% reduction of added sugar is less sweet, sourer, saltier, and has more tingling on the tongue compared to a ketchup prototype with DM09.

Figure 7:
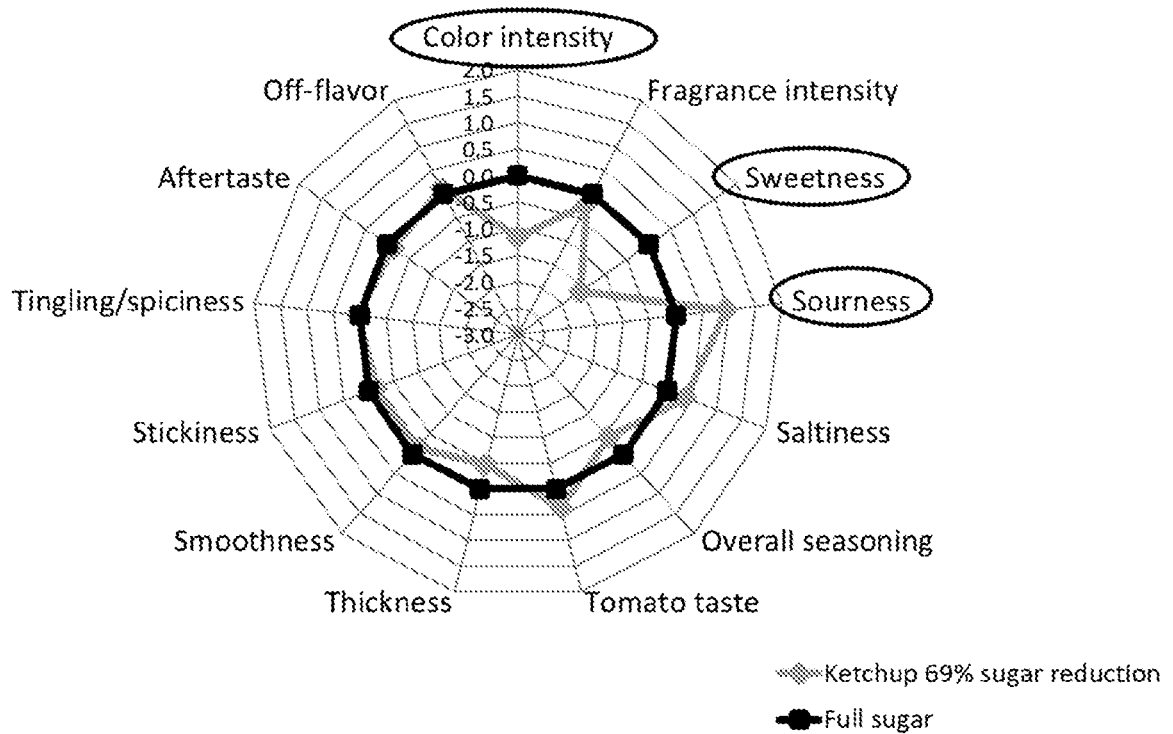
FIG. 7 is a spider graph showing that a ketchup prototype with a 69% reduction of added sugar is less sweet, sourer, and has a lighter color compared to ketchup with full sugar.

FIG. 7 shows that a ketchup prototype with a 69% reduction of added sugar is less sweet, sourer, and has a lighter color compared to a ketchup prototype with full sugar.

Figure 8:
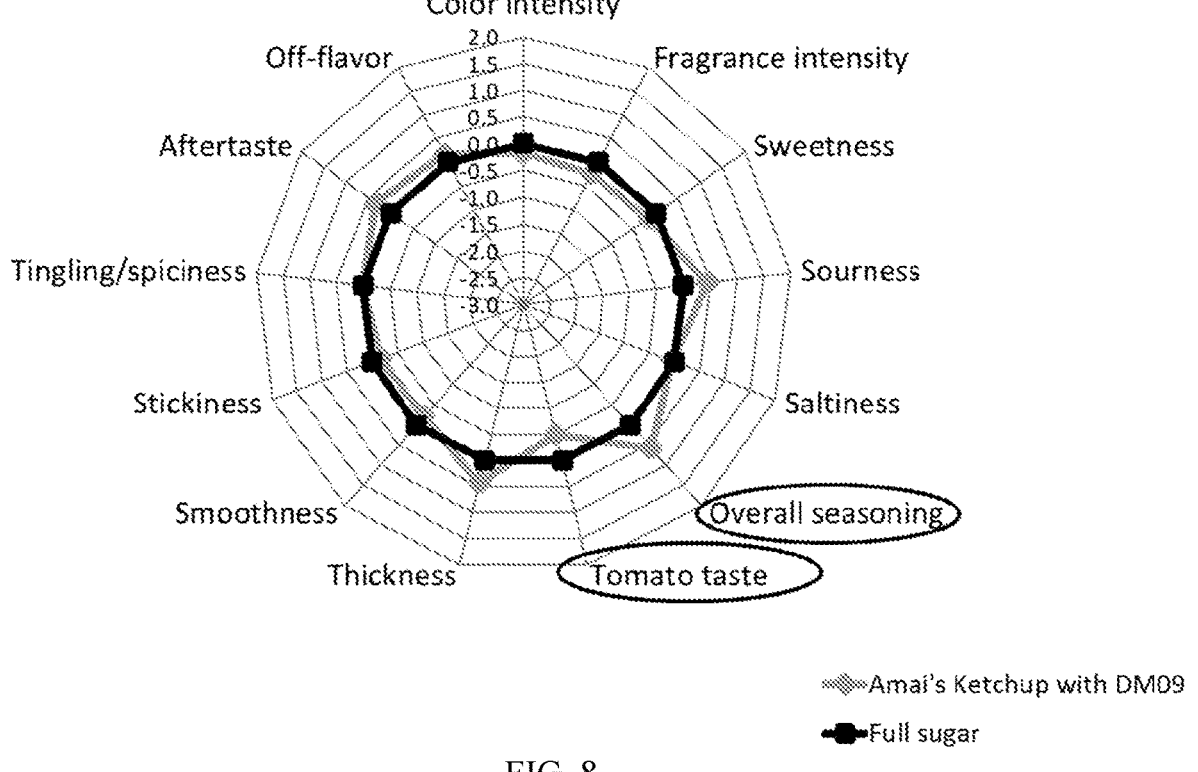
FIG. 8 is a spider graph showing that a ketchup prototype with DM09 (69% reduction of added sugar) has a very similar sensory profile to that of full sugar ketchup.

It was demonstrated that ketchup with DM09 (69% reduction of added sugar) has a very similar sensory profile to the full sugar ketchup prototype (FIG. 8).

Figure 9:
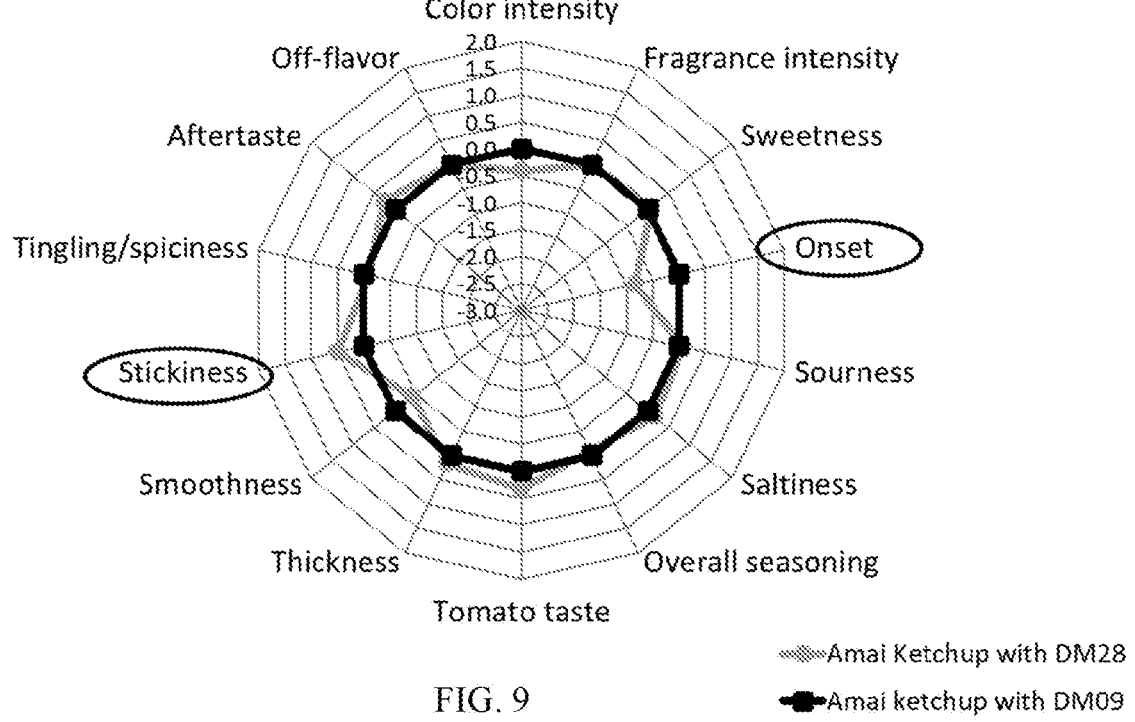
FIG. 9 is a spider graph showing that a ketchup with DM28 has a similar sensory profile compared to ketchup with DM09.

FIG. 9 demonstrates that ketchup with DM28 has a similar sensory profile compared to ketchup with DM09, except having more "late onset" and more stickiness.

Figure 18:
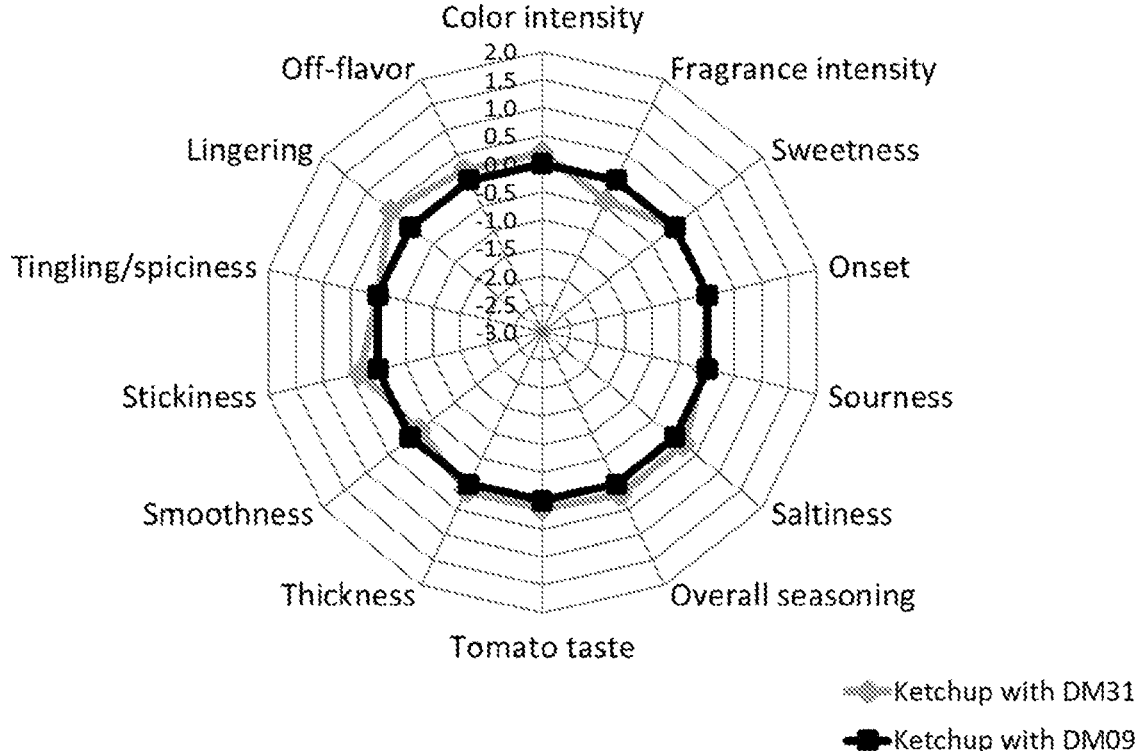
FIG. 18 is a spider graph showing that ketchup with DM031 (69% reduction of added sugar) has a very similar sensory profile to that of ketchup with DM09.

FIG. 18 demonstrates that ketchup with DM031 (69% reduction of added sugar) has a very similar sensory profile to that of the ketchup with DM09.

Figure 10:
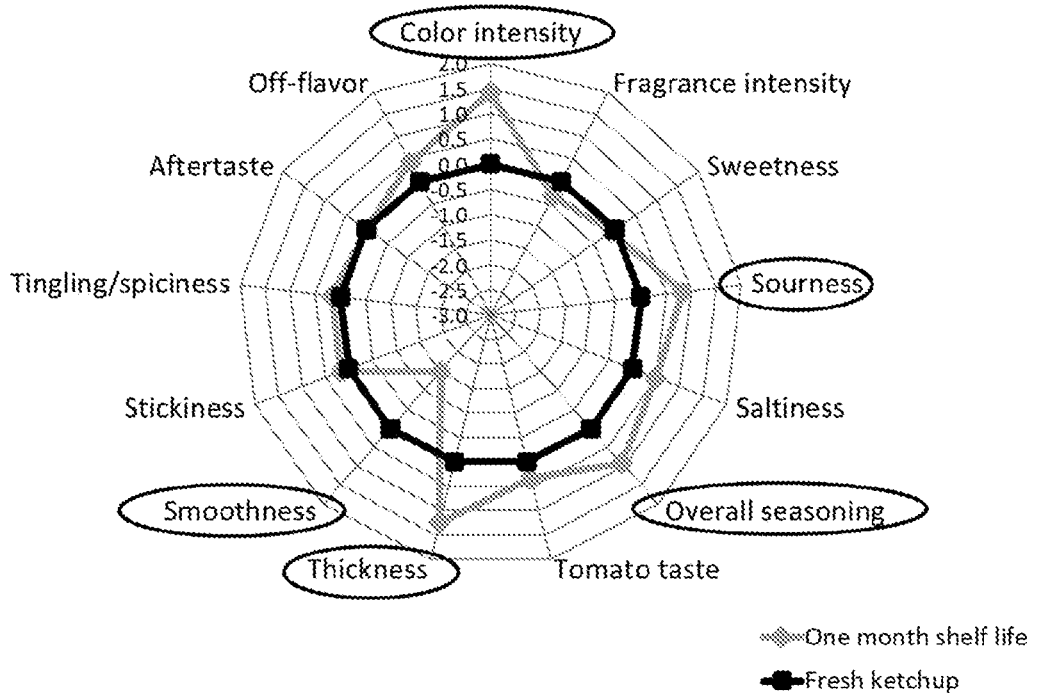
FIG. 10 is a spider graph showing that after one month of shelf life, ketchup with DM09 does not lose its sweetness. The changes that occur to the product are typical for ketchup following a shelf life of 1 month (darker color, more seasoned, more sour, thicker, and less smooth texture).

After one month of shelf life, ketchup with DM09 does not lose its sweetness. The changes that occur to the product are typical for ketchup after a shelf life of one month (darker color, more seasoned, sourer, thicker, and less smooth texture) (FIG. 10).

Yogurt Prototype

Figure 11:
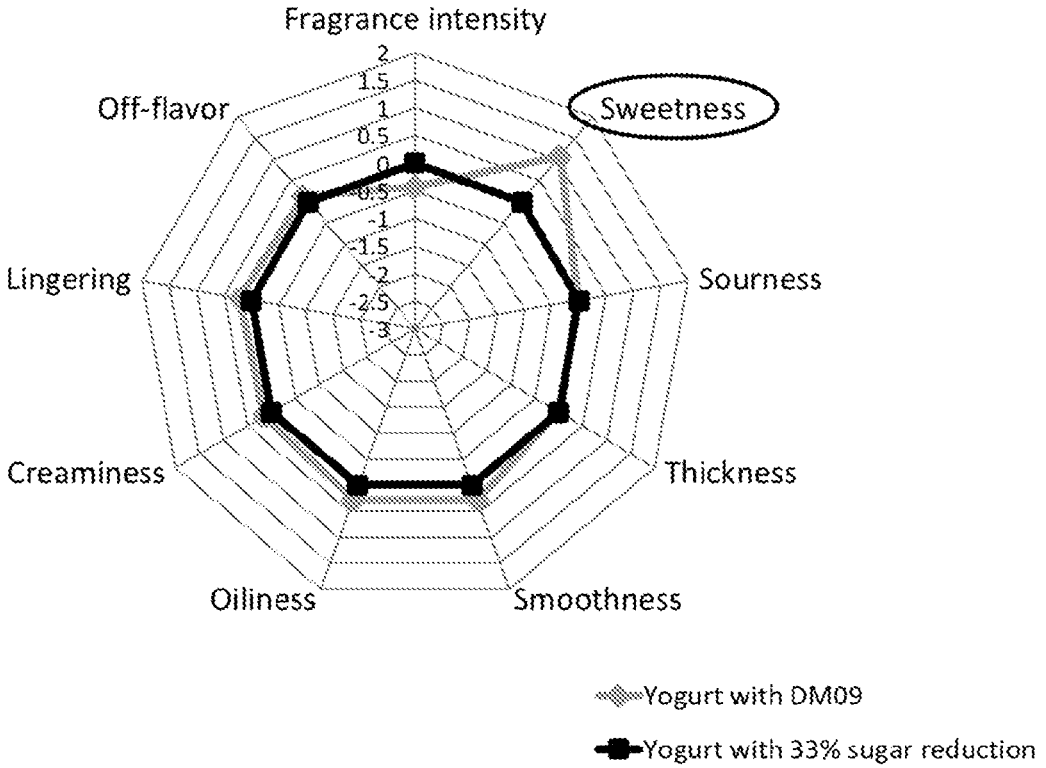
FIG. 11 is a spider graph showing that plain yogurt with a 33% reduction of added sugar is less sweet than plain yogurt with DM09 and a 33% reduction of added sugar.

As demonstrated in FIG. 11, plain yogurt with a 33% reduction of added sugar is less sweet than plain yogurt with DM09 and a 33% reduction of added sugar.

Figure 12:
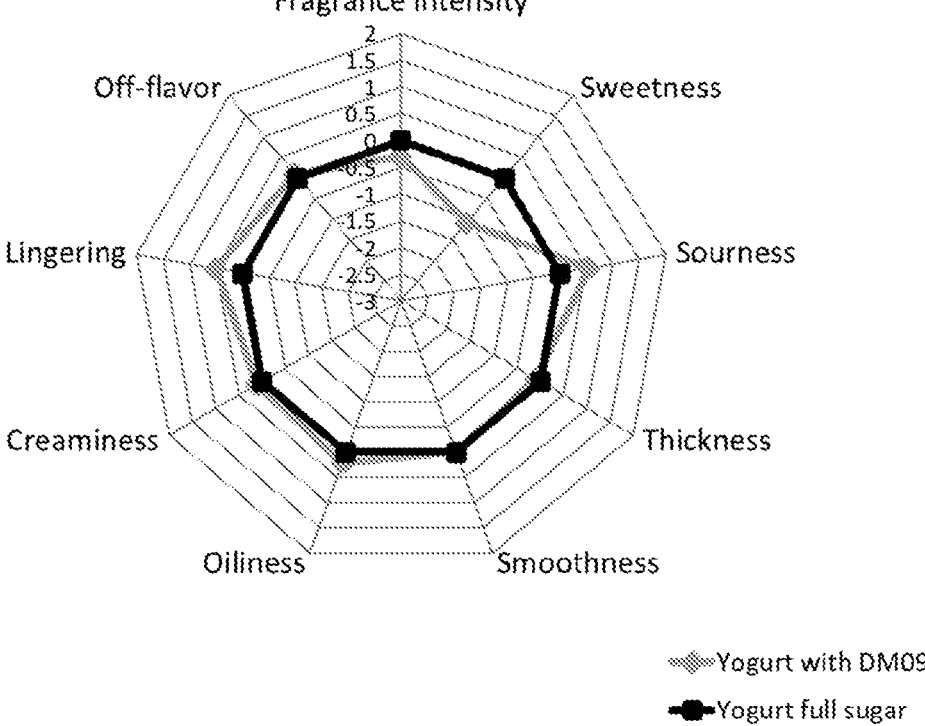
FIG. 12 is a spider graph showing that plain yogurt with DM09 (33% reduction of added sugar) has a similar sensory profile to a full sugar yogurt.

FIG. 12 demonstrates that plain yogurt with DM09 (33% reduction of added sugar) has a similar sensory profile to the full sugar yogurt prototype.

Figure 13:
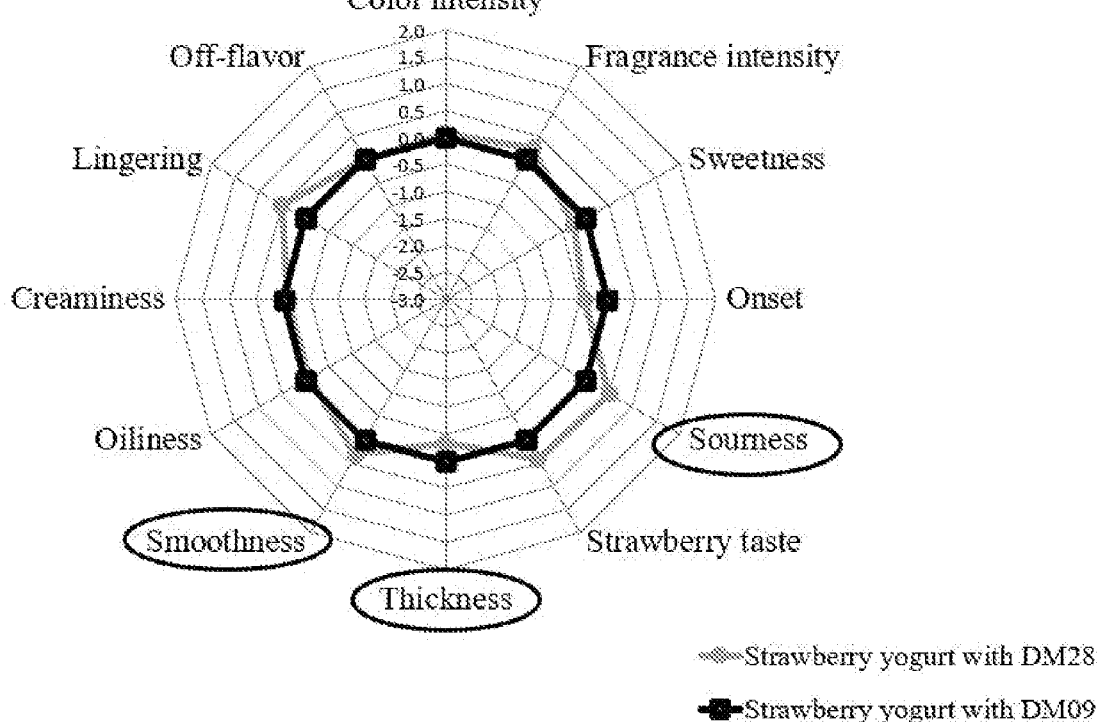
FIG. 13 is a spider graph showing that strawberry yogurt with DM28 has a similar sensory profile to strawberry yogurt with DM09.

As shown in FIG. 13, strawberry yogurt with DM28 has a similar sensory profile to strawberry yogurt with DM09, except being slightly sourer.

Figure 19:
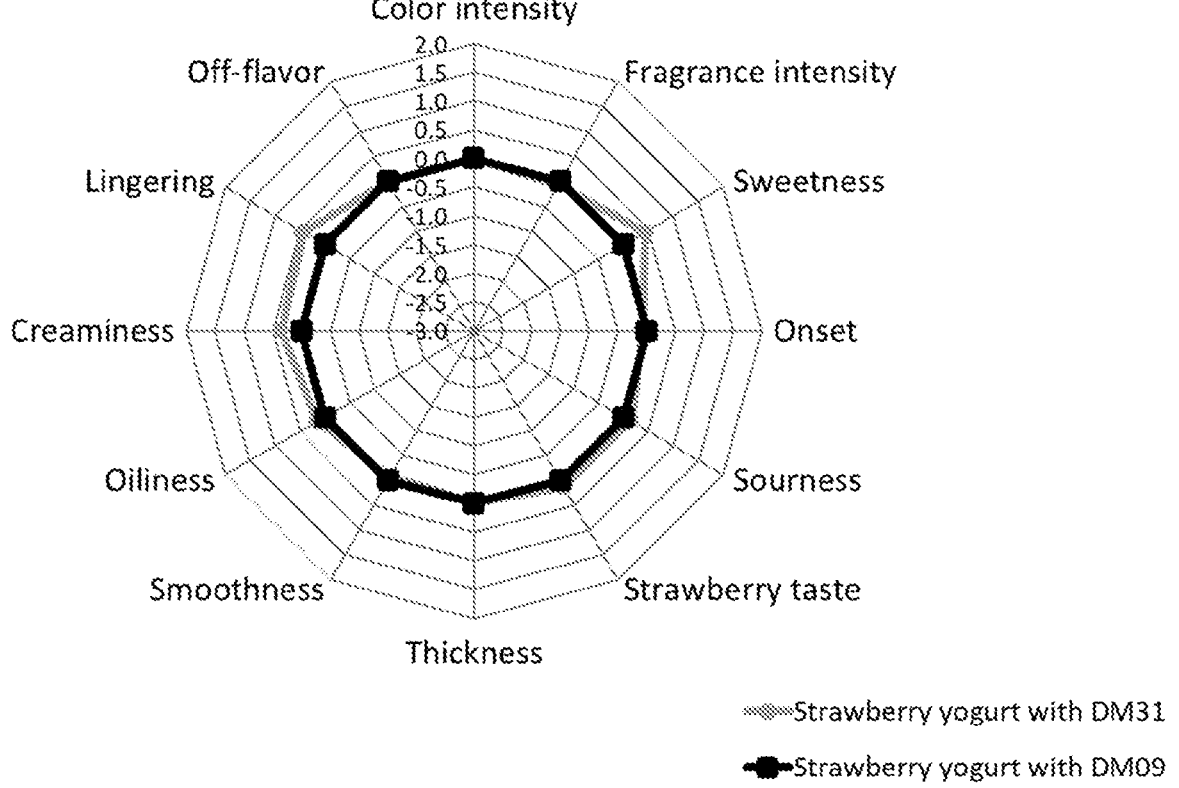
FIG. 19 is a spider graph showing that strawberry yogurt with DM31 has a similar sensory profile to strawberry yogurt with DM09.

FIG. 19 demonstrates that strawberry yogurt with DM31 has a similar sensory profile to strawberry yogurt with DM09.

Figure 14:
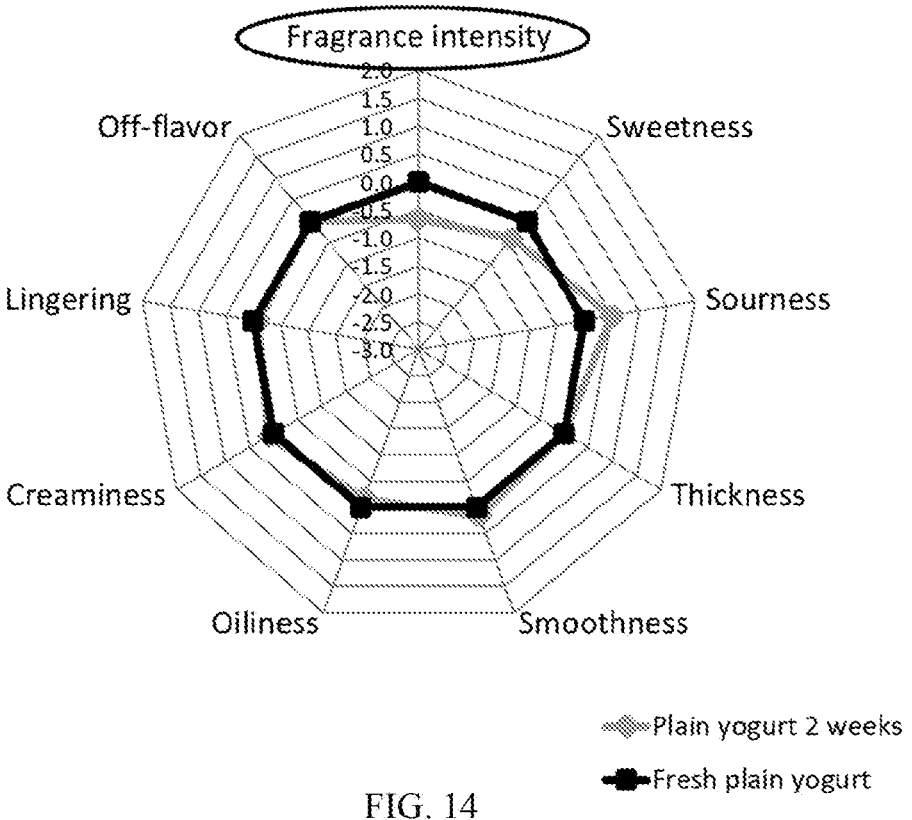
FIG. 14 is a spider graph showing that after two weeks of shelf life, plain yogurt with DM09 has a similar sensory profile to fresh plain yogurt with DM09.

FIG. 14 demonstrates that after two weeks of shelf life, a plain yogurt with DM09 has a similar sensory profile to the fresh plain yogurt with DM09.

Example 5: Combinations of Sweeteners

Sensory Profiles for Sweeteners—Testing Procedure

Many sweeteners and sweetener combinations were screened. The sweetener combinations with the best results were Stevia versus Stevia+DM09, and a combination of Monk fruit with Stevia versus Monk fruit, Stevia, and DM09. Each sweetness solution was at a final concentration equivalent to 5° Bx (in a combination of two sweeteners, each sweetener was at a concentration equivalent to 2.5° Bx and in a combination of three sweeteners, each sweetener was at a concentration equivalent to 1.7° Bx).

The sensory attributes in the questionnaire were determined by a preliminary tasting of the panelists.

Building sensory profiles for each sweetener solution: the panelists rated each tested solution (sweetener+DM09/DM28) versus a reference (the sweetener without DM09/DM28) on a two-way scale (between −3 to +3) with a fixed reference point (0) across the selected attributes. When the tested product was evaluated "more" than the reference on a specific attribute (e.g., sweeter, more lingering, and so on), it got positive rates (+1, +2, or +3) and when it was rated "less" than the reference on a specific attribute (e.g., less sweet, less lingering taste and so on), it got negative rates (−1, −2 or −3).

Before and between tasting, the tasters were requested to rinse their mouths with mineral water, eat an unsalted cracker and cucumber, and drink water again.

Lemon-flavored Drink Prototype

Formulations of lemon-flavored drinks with DM proteins are presented in Tables 7-8.

TABLE 7

| DM09 based lemon-flavored drink | | | |
|---|---|---|---|
| 10 Bx - 50% added sugar reduction | | | % |
| | water | 850 ml | 93.99 |
| | lemon flavour | 1.7 g | 0.19 |
| 5 Bx | DM09 (5.14 mg/ml) | 0.845 ml | 0.09 |
| | citric acid | 0.85 g | 0.09 |
| | Sugar | 51 g | 5.64 |
| | | 904.395 | 100.00 |

TABLE 8

| DM09 and stevia based lemon-flavored drink (10° Bx, 50% added sugar reduction) | | |
|---|---|---|
| | Application with Stevia (5° Bx equivalent) | Application with Stevia + DM09 (2.5° Bx equivalent each) |
| Water (g) | 90-112 | 90-112 |
| lemon flavor (g) | 0.18-0.224 | 0.18-0.224 |
| DM09 (5.14 mg/ml) (ml) | — | 0.046-0.056 |
| Reb M (mg) | 18-22.4 | 9-11.2 |
| citric acid (g) | 0.09-0.112 | 0.09-0.112 |
| Sugar (g) | 5.4-6.7 | 5.4-6.7 |

Results

Figure 15:
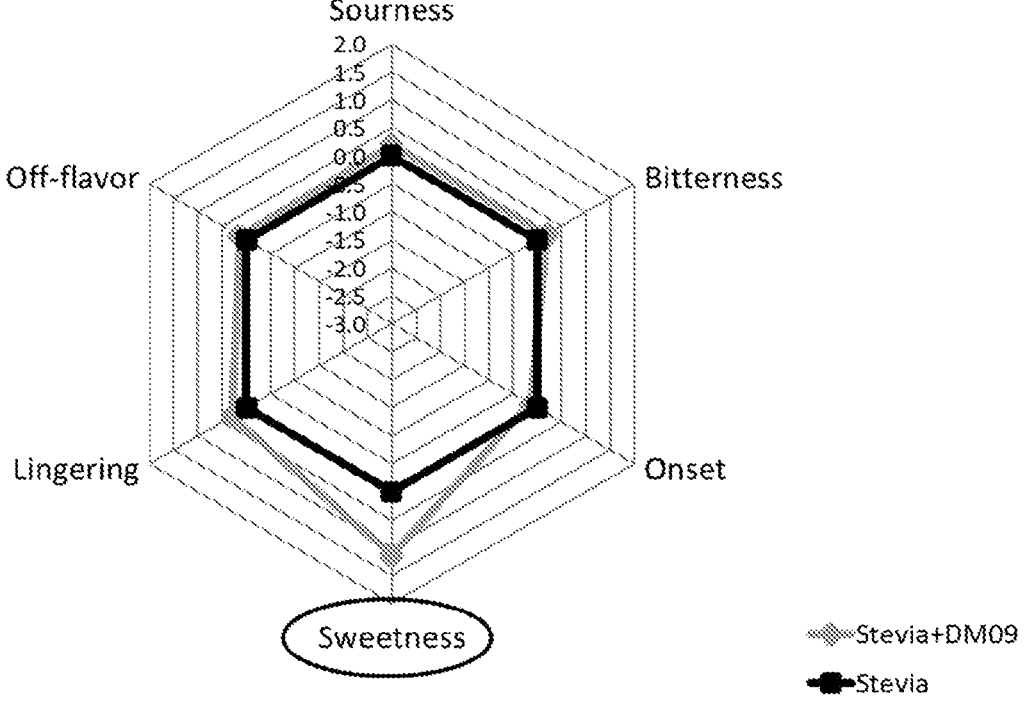
FIG. 15 is a spider graph showing that a water solution with stevia and DM09 is sweeter than a water solution with stevia alone, at the same sweetness level equivalent.
Figure 16:
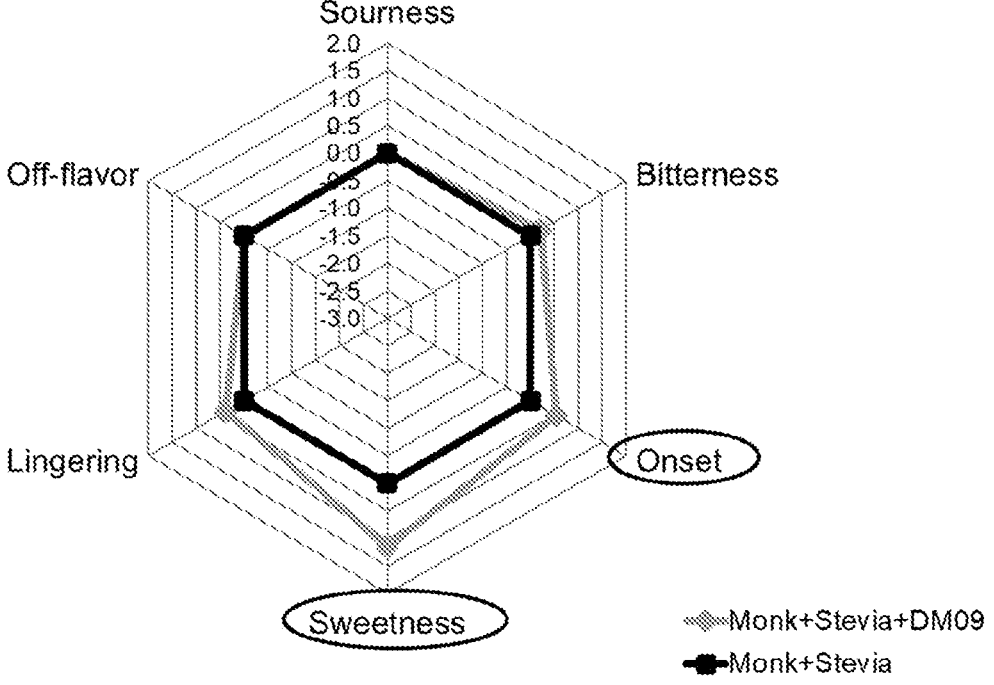
FIG. 16 is a spider graph showing that a water solution with a combination of Monk fruit, stevia, and DM09 is sweeter, with shorter "late onset" compared to a water solution with Monk fruit and stevia alone, in the same sweetness level equivalent.

As shown in FIG. 15, a water solution with stevia and DM09 is sweeter than a water solution with stevia alone, at the same sweetness level equivalent. FIG. 16 demonstrates that a water solution with a combination of Monk fruit, stevia, and DM09 is sweeter with a shorter "late onset," compared to a water solution with Monk fruit and stevia alone, at the same sweetness level equivalent.

Figure 17:
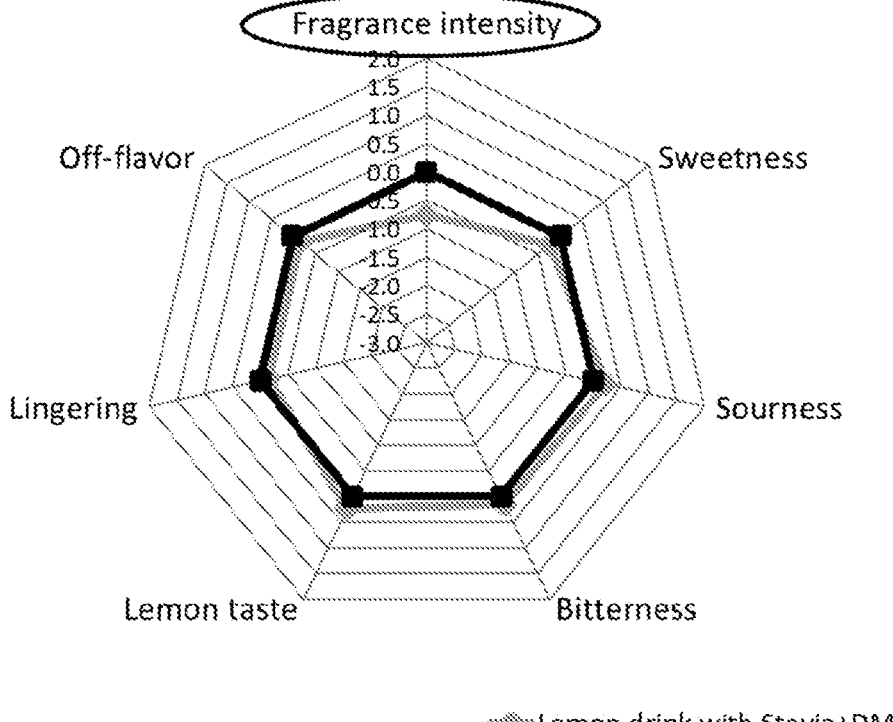
FIG. 17 is a spider graph showing that a lemon-flavored drink (50% sugar reduction with Stevia, 5° Bx equivalent) has a very similar sensory profile to Stevia and DM09 (2.5° Bx equivalent each).

As shown in FIG. 17, a lemon-flavored drink (50% added sugar reduction with Stevia (5° Bx equivalent) has a very similar sensory profile to Stevia and DM09 (2.5° Bx equivalent each).

Example 6: Chewing Gum Prototype with Designer-Monellin (DM) Proteins

Chewing gum is usually composed of gum base, softeners, sweeteners, and flavors. Gum base is what gives chewing gum its "chew." It is made of a combination of food-grade polymers, waxes, and softeners that give the gum the desired texture.

Formulations of chewing gum with DM protein is presented in Table 9.

TABLE 9

| DM09 based chewing gum | |
| --- | --- |
| Material | Percentage |
| Sorbitol | 13-17% |
| Mannitol | 9-14% |
| Syrup maltitol | 3-8% |
| Acesulfame k | 0.05-0.5% |
| Sucralose | 0.05-0.5% |
| Gum base | 14-19% |
| Glycerin | 2-4% |
| Flavors | 1-3% |
| Soy lecithin | 0.03-0.08% |
| Butylated hydroxyanisole | 0.4-0.9% |
| Water | 2-5% |
| Maltodextrin | 38-45% |
| DM09 | 0.01-0.03% |

Preparation Instructions

First, the gum base is heated, and the melted mass is placed in a mixer.

Next, ingredients 1-13 are added gradually during constant mixing.

Then, the mass is kneaded to smooth, form, and shape the gum.

The reference chewing gum sample, containing sugar alcohols and artificial sweeteners, is compared to a chewing gum sample with the same amount of sugar alcohols and artificial sweeteners to which sweet protein was added.

0.01-0.05% by weight of sweet protein was added to the recipe.

The sweet protein potency is 4000-8000, equivalent to 48-56 brix.

Sensory Panel

A sensory profile for chewing gum was built using a trained expert panel for analytical discrimination.

The panelists rated each tested chewing gum product across all attributes in a questionnaire.

The attributes were measured after 30 seconds, 2 minutes, and 4 minutes.

Before and between the products, the tasters were requested to rinse their mouths with mineral water, eat an unsalted cracker and a cucumber, and drink water again.

Results

Figure 20:
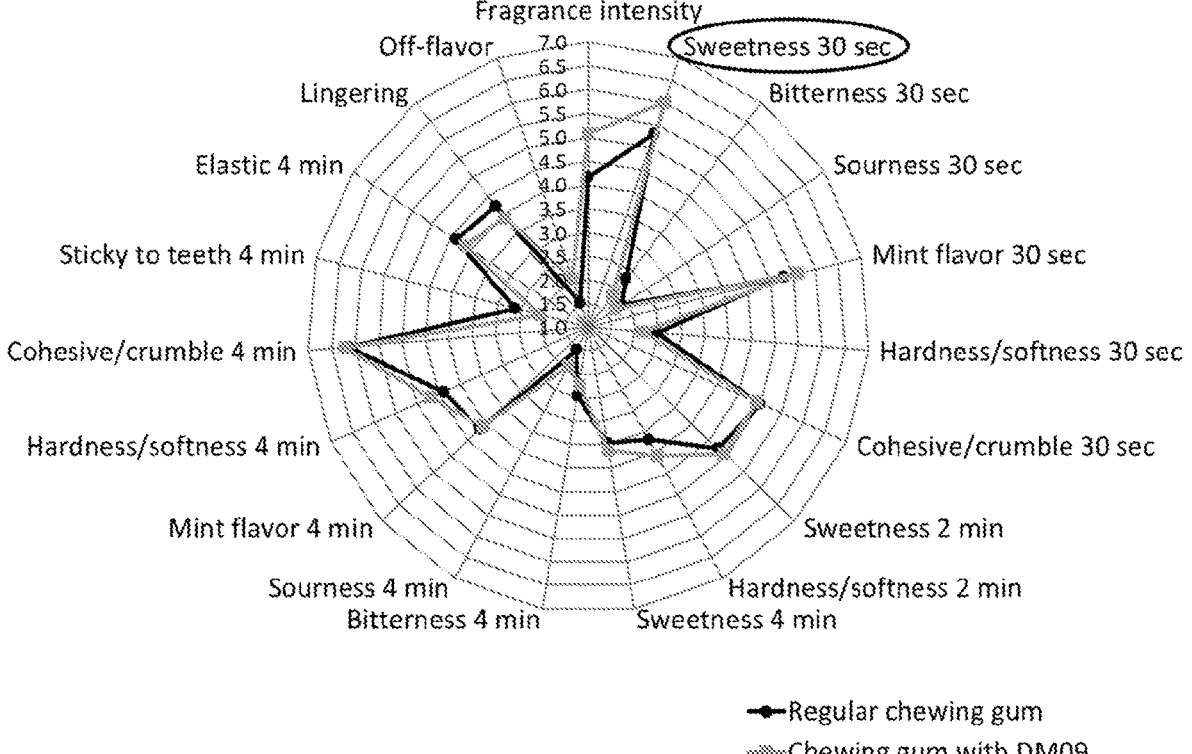
FIG. 20 is a spider graph showing that chewing gum with DM09 is sweeter than chewing gum without DM09 after 30 seconds of chewing.

As shown in FIG. 20, chewing gum with DM09 is sweeter than chewing gum without DM09 after 30 seconds of chewing

Example 7: Peanut Butter Prototype with Designer-MNEI (DM) Proteins

Formulations of peanut butter with DM protein is presented in Table 10.

TABLE 10

| DM09 based peanut butter | | |
| --- | --- | --- |
| ingredients | Full sugar | 50% sugar reduction |
| Peanut butter paste (g) | 80-100 | 80-100 |
| Fat (g) | 1-3 | 1-3 |

TABLE 10-continued

| DM09 based peanut butter | | |
| --- | --- | --- |
| ingredients | Full sugar | 50% sugar reduction |
| NaCl (g) | 0.1-0.3 | 0.1-0.3 |
| Sugar (g) | 4-6 | 1-3 |
| Maltodextrin (g) | — | 2-4 |
| Dried DM09 (g) | — | 0.0006-0.0008 |
| Fibers (g) | — | 1-3 |
| Lecithin (g) | 0-10 | 0-10 |

All the ingredients are mixed until the mixture is homogenous.

Results

Figure 21:
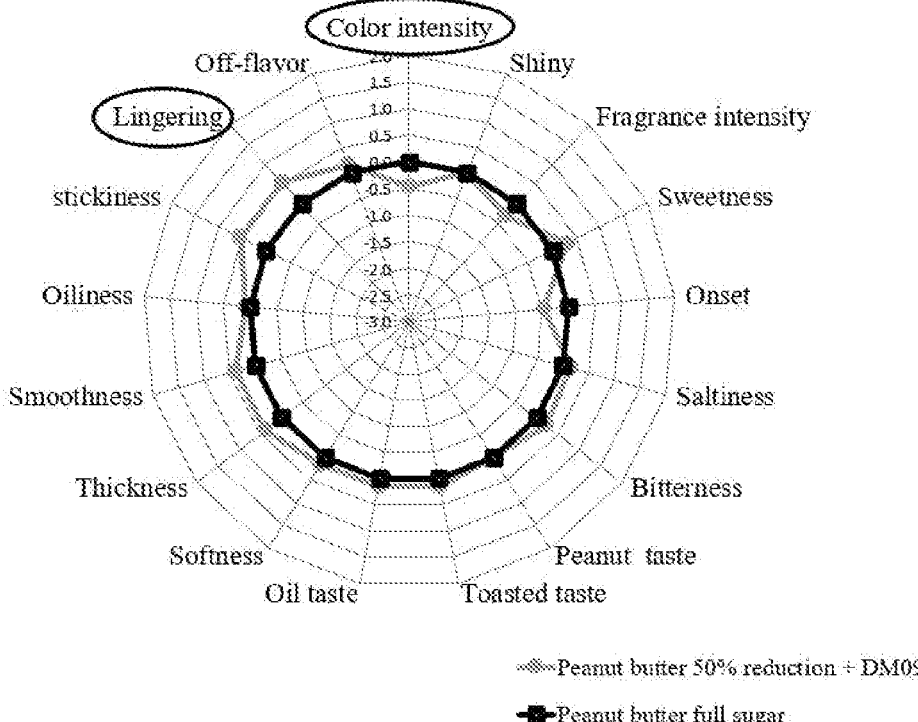
FIG. 21 is a spider graph showing that peanut butter with DM09 and a 50% sugar reduction has a similar sensory profile to that of full sugar peanut butter.

As shown in FIG. 21, peanut butter with DM09, 50% sugar reduction, has a very similar sensory profile to that of full sugar peanut butter.

Example 8: Ice Coffee Prototype with Designer-MNEI (DM) Proteins

Formulations of iced coffee with DM protein is presented in Table 11.

TABLE 11

| DM09 based ice coffee | |
| --- | --- |
| Ingredients | |
| Coffee (g) | 0.5-2 |
| Sugar (g) | 1-3 |
| Maltodextrin (g) | 4-6 |
| DM 09 (g) | 0.002-0.003 |
| Milk (g) | 92 |

Coffee, sugar, maltodextrin and DM09 are mixed to a combined mixture. Then 7-9 g of the mixture are mixed with 89-94 g milk until the mixture is homogenous.

Results

Figure 22:
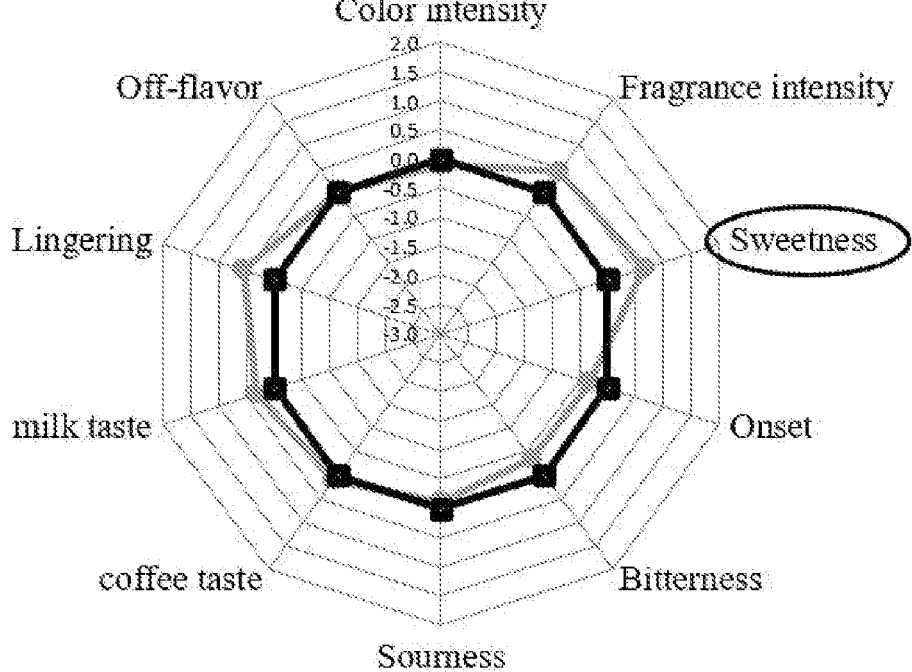
FIG. 22 is a spider graph showing that iced coffee with DM09 (70% sugar reduction) is sweeter than iced coffee without DM09 (70% sugar reduction).

As shown in FIG. 22, iced coffee with DM09 (70% sugar reduction) is sweeter than ice coffee (70% sugar reduction) without DM.

Example 9: Cranberry Juice Prototype

Formulations of Cranberry juice with DM proteins are presented in Tables 12-15.

TABLE 12

| DM09 and stevia based Cranberry juice (40% sugar reduction) | | |
| --- | --- | --- |
| | Percentage | 1000 ml |
| Cranberry JC 50 Bx | 3-6 | 30-60 (g) |
| Sucrose | 4-8 | 40-80 (g) |
| DM09 (5.14 mg/ml) | 0.08-0.24 | 0.8-2.4 (ml) |
| Reb M PureCircle | 0.0025-0.004 | 0.025-0.04 (g) |
| NaCl | 0.02-0.06 | 0.2-0.6 (g) |
| Water | 85-90 | 850-900 (g) |
| Total | 100 | 1000.061 |

TABLE 13

DM09 and DM16 based Cranberry juice
(40% sugar reduction (6° Bx))

|  | Percentage | 1000 ml | |
|---|---|---|---|
| Cranberry JC 50 Bx | 3-6 | 30-60 | (g) |
| Sucrose | 4-8 | 40-80 | (g) |
| DM09 (5.14 mg/ml) | 0.2-0.4 | 2-4 | (ml) |
| DM16 (5.8 mg/ml) | 0.08-0.14 | 0.8-1.4 | (ml) |
| NaCl | 0.02-0.06 | 0.2-0.6 | (g) |
| Water | 85-90 | 850-900 | (g) |
| Total | 100 | 1000.1 | |

TABLE 14

DM28 based Cranberry juice (40% sugar reduction (6° Bx))

|  | Percentage | 1000 ml | |
|---|---|---|---|
| Cranberry JC 50 Bx | 3-6 | 30-60 | (g) |
| Sucrose | 4-8 | 40-80 | (g) |
| DM28 (9.6 mg/ml) | 0.08-0.13 | 0.8-1.13 | (ml) |
| Reb M (PureCircle) | 0.0028-0.0042 | 0.028-0.042 | (g) |
| NaCl | 0.02-0.06 | 0.2-0.6 | (g) |
| Water | 85-90 | 850-900 | (g) |
| Total | 100 | 1000.1 | |

TABLE 15

DM31 based Cranberry juice (40% sugar reduction (6° Bx))

|  | Percentage | 1000 ml | |
|---|---|---|---|
| Cranberry JC 50 Bx | 3-6 | 30-60 | (g) |
| Sucrose | 4-8 | 40-80 | (g) |
| DM31 (3.62 mg/ml) | 0.12-0.35 | 1.2-3.5 | (ml) |
| Reb M (PureCircle) | 0.0028-0.0042 | 0.028-0.042 | (g) |
| NaCl | 0.02-0.06 | 0.2-0.6 | (g) |
| Water | 85-90 | 850-900 | (g) |
| Total | 100 | 1000.061 | |

Results

Figure 23:
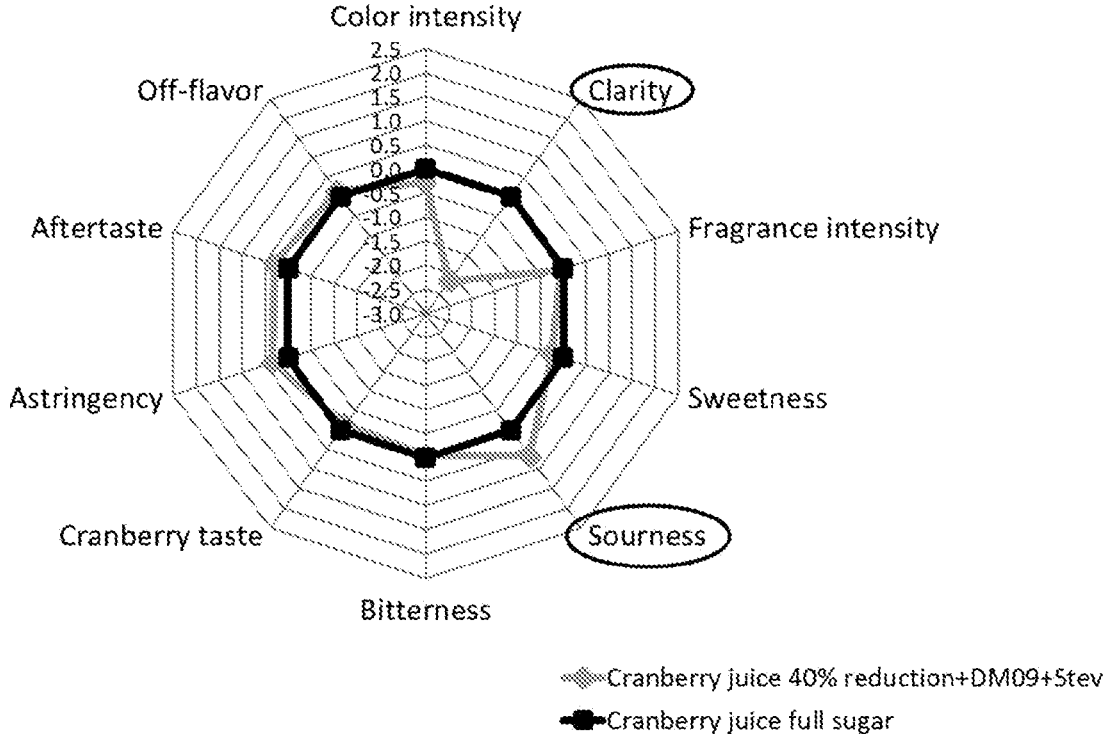
FIG. 23 is a spider graph showing that cranberry juice (40% sugar reduction, stevia, and DM09) has a similar sensory profile to full sugar cranberry juice.
Figure 24:
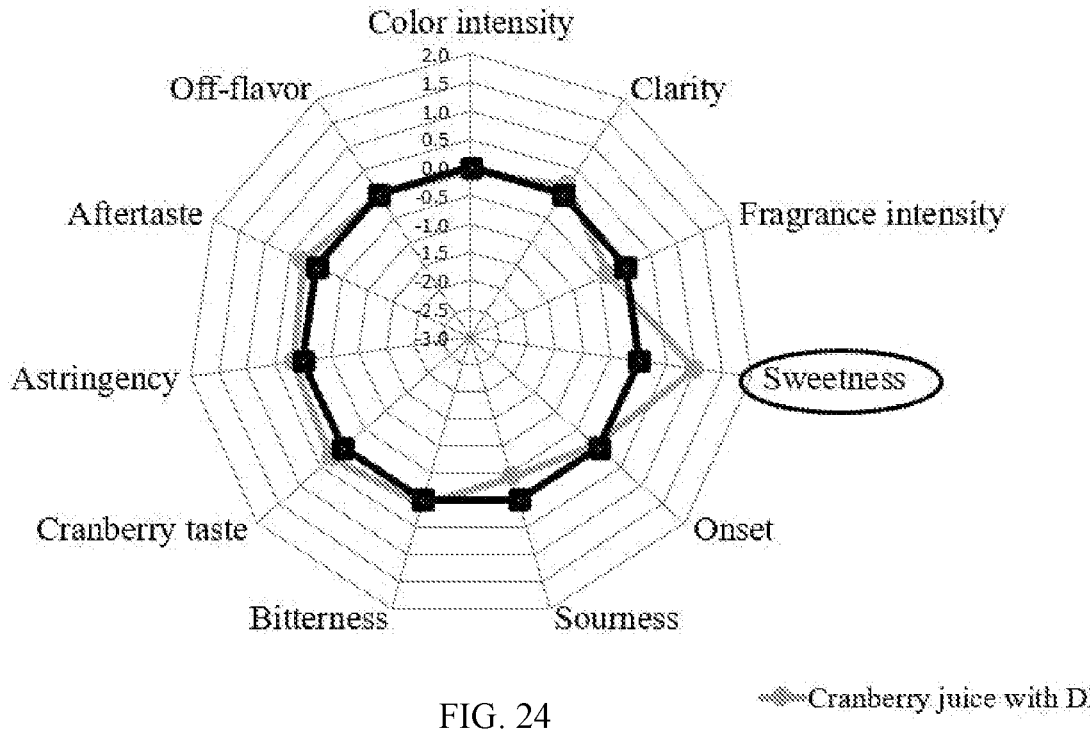
FIG. 24 is a spider graph showing that cranberry juice with DM28 is sweeter than cranberry juice with DM09.
Figure 25:
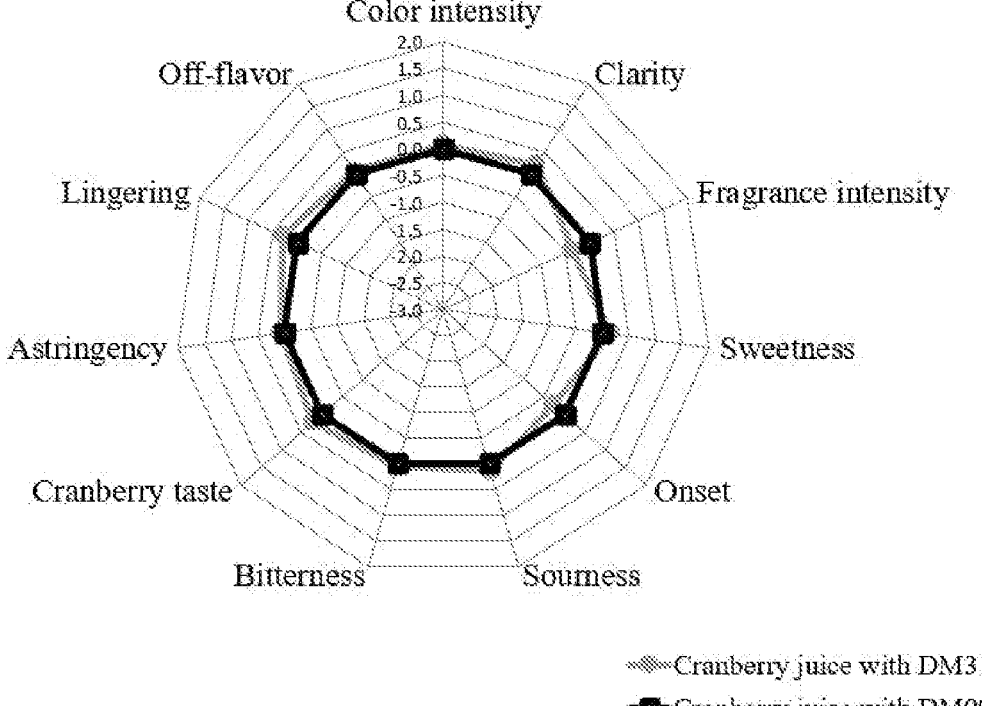
FIG. 25 is a spider graph showing that cranberry juice with 40% sugar reduction, stevia, and DM31 has a similar sensory profile to cranberry juice with 40% sugar reduction, stevia, and DM09).

FIG. 23 demonstrates that cranberry juice (40% sugar reduction, stevia and DM09) has a similar sweetness to the full sugar cranberry juice. FIG. 24 demonstrates that cranberry juice with DM28 is sweeter than cranberry juice with DM09. FIG. 25 demonstrates that cranberry juice (40% sugar reduction, stevia, and DM31) has a similar sensory profile to cranberry juice with a 40% sugar reduction, stevia, and DM09.

Example 10: Dried Cranberries and Peach Leather Prototypes

Formulations of dried cranberries with DM proteins are presented in Tables 16-18.

TABLE 16

Dried cranberries with DM proteins
(50% added sugar reduction and 45% sugar + 5% fructose)

|  | Application full sugar (100 g infusion) | Application with DM (100 g infusion) |
|---|---|---|
| Water (g) | 28-35 | 50-75 |
| 50 Brix Cranberry concentrate (g) | 4.5-5.5 | 4-8 |

TABLE 16-continued

Dried cranberries with DM proteins
(50% added sugar reduction and 45% sugar + 5% fructose)

|  | Application full sugar (100 g infusion) | Application with DM (100 g infusion) |
|---|---|---|
| DM09 (5.14 mg/ml) (ml) | — | 1.4-1.8 |
| NaCl (g) | 0.03-0.07 | 0.03-0.07 |
| Sugar (g) | 53-72 | 20-40 |
| Fructose (g) | — | 2-5 |

The cranberries were soaked in infusion syrup at a ratio of 1:3 for up to 6 hours until the cranberries reach 45-60° Bx (for full sugar application) or 20-30° Bx (for the DM application), the cranberries were then oven-dried at 70-120° C. until they reach 70-86° Bx (for full sugar application) or 33-45° Bx (for DM application).

TABLE 17

Dried cranberries prototype with DM
proteins (40% added sugar reduction)

|  | Application full sugar (100 g infusion) | Application with DM (100 g infusion) |
|---|---|---|
| Water (g) | 28-35 | 50-61 |
| 50 Brix Cranberry concentrate (g) | 4-6 | 4-8 |
| DM09 (5.14 mg/ml) (ml) | — | 1.17-1.43 |
| NaCl (g) | 0.03-0.07 | 0.03-0.07 |
| Sugar (g) | 53-72 | 31-45 |

The cranberries were soaked in infusion syrup at a ratio of 1:3 for up to 6 hours until they reached 45-60° Bx (for the full sugar application) or 25-38° Bx (for the DM application), the cranberries were then oven-dried at 70-120° C. until they reach 74-84° Bx (for full sugar application) or 42-54° Bx (for DM application).

TABLE 18

Dried cranberries prototype with DM
proteins (50% added sugar reduction)

| Infusion Syrup |  | full sugar | 50% sugar reduction |
|---|---|---|---|
|  | Sugar (g) | 63.5 | 31.75 |
|  | 50 Brix Cranberry concentrate (g) | 5 | 5 |
|  | Water (g) | 31.5 | 62.5 |
|  | DM09 (12.97 mg/ml) (ml) | — | 0.644 |
|  | NaCl (g) | 0.05 | 0.05 |
| Total |  | 100 | 100 |
| After 2 h in oven (for 100 g dried cranberries) | Maltodextrin (g) | — | 1.257 |
|  | DM09 (g) | — | 0.003174 |

The cranberries were soaked in an infusion syrup at a ratio of 1:3 for 2-6 hours until cranberries reached 45-60° Bx (for the full sugar application) or 20-30° Bx (for the DM application). The cranberries are then oven-dried at 70-120° C. Drying is considered complete when the cranberries reach 70-86° Bx for a full sugar application or 33-45° Bx for a DM application. After 2 h the cranberries are removed from the oven and the mixture (Maltodextrin & dried DM09) is sprayed on the dried cranberries (the mixture sprayed amount is equivalent to 10% added sugar-amount was calculated from the full sugar recipe). The cranberries are put back into the oven for further drying for an additional 10-30 minutes at 70-120° C.

Formulation of peach leather with DM09 is presented in Table 19.

TABLE 19

Peach leather prototype with DM-09

| Ingredients | Peach leather (Sweetness equivalent to 40 Bx) |
| --- | --- |
| Peach paste | 98-100 g |
| Citric acid | 0.1-0.2 g |
| DM09 (12.3 mg/ml) | 0.7-0.9 ml |

Peaches were peeled and the pits were removed out. The peeled peaches were blended with citric acid to a smooth paste in a food processor. Then DM09 was added to the homogenous blend. The mixture was poured and smoothed into a thin uniform layer and dried in a dehydrator oven for 9-10 hours at 40° C., until it was dry. The dried peach leather was taken out and cooled down. The leather was rolled and stored in an airtight container.

Results

Figure 26:
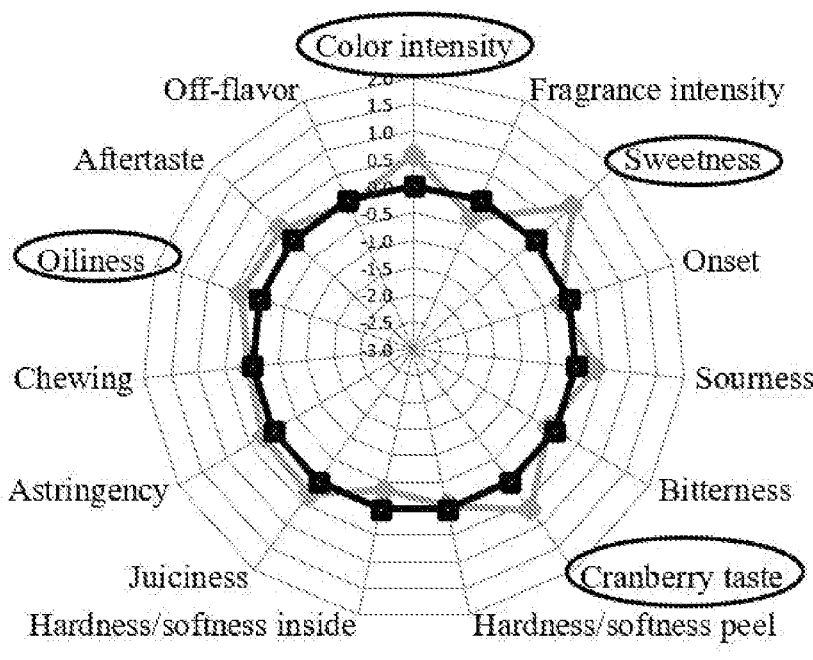
FIG. 26 is a spider graph showing that dried cranberries (50% sugar reduction and DM09) are sweeter than dried cranberries without DM09 (50% sugar reduction).

FIG. 26 demonstrates that dried cranberries (50% sugar reduction and DM09) are sweeter compared to dried cranberries (50% sugar reduction).

Figure 27:
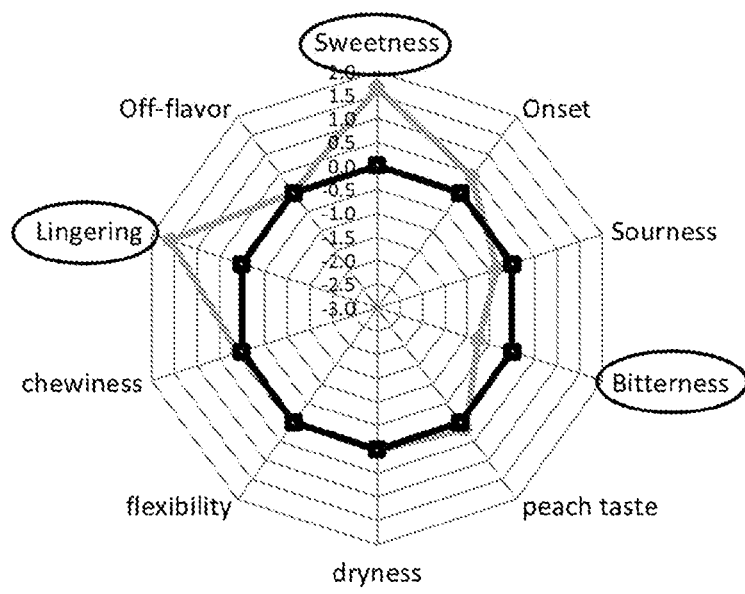
FIG. 27 is a spider graph showing that peach leather with DM09 is sweeter than peach leather without DM09.

FIG. 27 demonstrates that peach leather with DM09 is sweeter than peach leather without DM09.

Example 11: Green Iced-tea Prototype with Designer-MNEI (DM) Proteins

Formulations of green iced tea with DM protein is presented in Table 20.

TABLE 20

DM09 based iced tea

| Ingredients | 40% sugar reduction* | 40% sugar reduction + DM09 |
| --- | --- | --- |
| Green tea extract** | 86-100 (g) | 86-100 (g) |
| Sugar | 4.3-5.3 (g) | 4.3-5.3 (g) |
| Citric acid | 0.2-0.3 (g) | 0.2-0.3 (g) |
| DM09 (12.97 mg/ml) | — | 0.03-0.04 (ml) |
| Reb-M | — | 0.002-0.003 (g) |

*Full sugar ice-tea contains 8 g/100 ml
**Green tea extract is made by soaking green tea bags in water at 95° C. for 1.5 minutes.

Results

Figure 28:
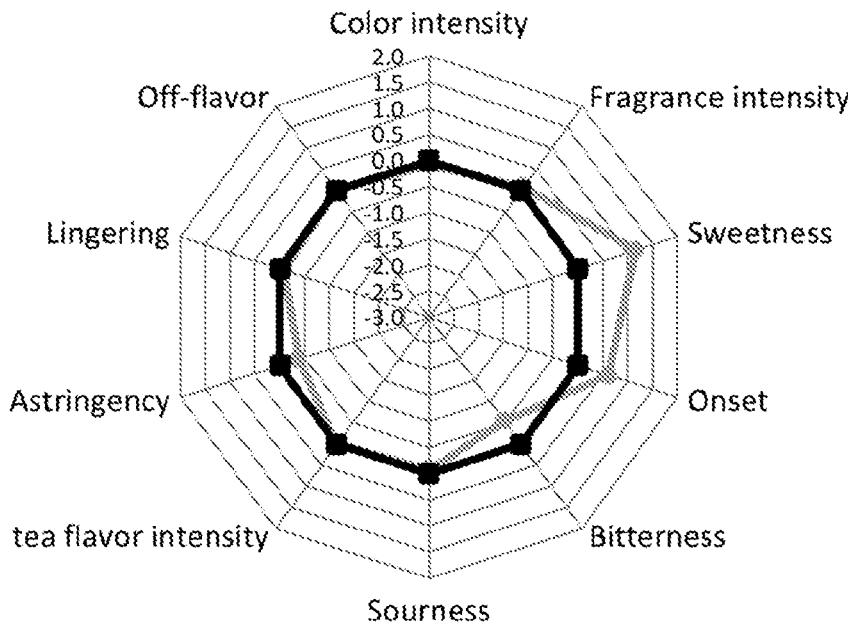
FIG. 28 is a spider graph showing that green iced tea with 40% added sugar reduction+DM09 and stevia is sweeter compared to green iced tea with 40% added sugar reduction without DM09 and stevia.

As shown in FIG. 28, green iced-tea with 40% added sugar reduction+DM09 and stevia is sweeter compared to green iced-tea with 40% added sugar reduction without stevia.

Example 12: Malabi Prototype with Designer-MNEI (DM) Proteins

Formulations of Malabi with DM protein is presented in Table 21.

TABLE 21

DM31 based Malabi prototype

| Ingredients | 50% sugar reduction | 50% sugar reduction + DM31 |
| --- | --- | --- |
| Milk | 54-66 (g) | 54-66 (g) |
| Cream | 22-28 (g) | 22-28 (g) |
| Sugar | 2-3 (g) | 2-3 (g) |
| Corn flour | 5-6 (g) | 5-6 (g) |
| Rose water | 1-2 (g) | 1-2 (g) |
| DM31 (15.88 mg/ml) | — | 0.08-0.1 (ml) |
| Water | 5-6 (g) | 5-6 (g) |

Milk, cream, sugar and rose water were heated to 100° C. Meanwhile, the corn flour was mixed with the water. When the liquids reached 100° C. the corn flour was added and mixed. When the temperature drops to 60° C., DM31 was added and mixed. The dessert was poured into serving dishes and cooled.

Results

Figure 29:
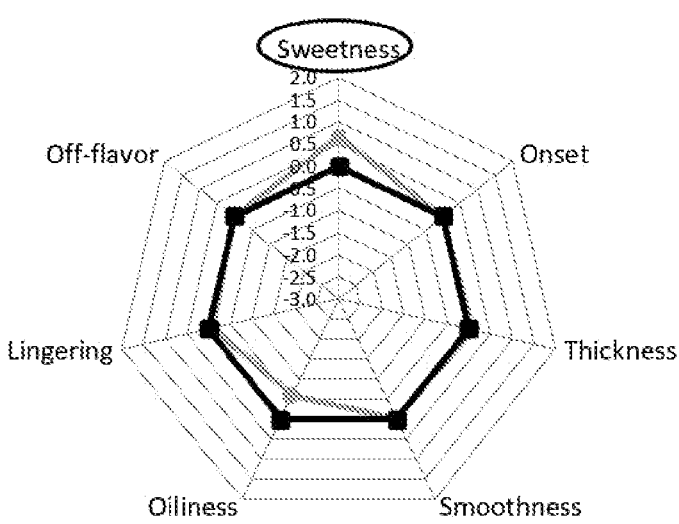
FIG. 29 is a spider graph showing that Malabi with 50% added sugar reduction+DM31 is sweeter compared to Malabi with 50% added sugar reduction without DM31.

As shown in FIG. 29, Malabi with 50% added sugar reduction+DM31 is sweeter compared to Malabi with 50% added sugar reduction.

Example 13: In-vitro Digestibility Study

The aim of the digestibility study was to determine the fate of the DM protein, to be used as a sweetener, in the gastrointestinal tract following digestion. The tested protein was the DM31 protein, produced by Precision Fermentation in *Escherichia coli* (*E. coli*) BL21 (DE3).

The in vitro digestibility static model was conducted according to INFOGEST protocol (Nature Protocols 14, 991-1014 (2019)).

In silico allergenicity analysis was performed on the digested peptides obtained at the end of the digestion models.

The digestibility cycles include Oral digestion (M), Gastric digestion (G) and Duodenal gut digestion (D). The Digestion enzymes used: Gastric pepsin (prepared in Simulated Gastric Fluids (SGF)—(2,000 U/ml SGF)), Digestion duodenal enzymes were prepared in Simulated Duodenal Fluids (SDF)—Trypsin (100 U/mL SDF), and chymotrypsin (25 U/mL SDF). Positive control was a known, fully digestible protein, α-lactalbumin. Negative control had no protein present.

Sample analyses used: Protein SDS gels—protein samples at each digestibility phase were run on 16.5% SDS PAGE Tricine protein gels, stained using Coomassie blue.

Mass spectrometry peptides identification: two repeats of each cycle, G and D, were analyzed by LC-MS/MS at the Smoller Proteomics Center, Technion using Q-Exactive plus (Thermo) and identified by Discover software against the sequence of DMs and host microorganism (*E-coli*) database.

Results

As shown in FIG. 34, the DM31 protein is partly digested at the end of the Gastric phase and fully digested at the end of the Duodenal phase. The results obtained by the static model using the INFOGEST protocol clearly demonstrate the digestibility of the DM protein during the physiological digestibility process.

During DM-31 digestion, the peptides that are generated within the intestinal track have no allergenicity risk. The results demonstrate that DM-31 digestion is not associated with any safety concerns.

---

The invention claimed is:

1. A modified single chain Monellin (MNEI) protein, comprising an amino acid sequence that has two or more amino acids deletions and/or two or more amino acids insertions, to that of a reference MNEI protein, wherein the modified MNEI protein has at least one improved food-related property compared to the reference MNEI protein, and wherein the reference MNEI protein comprises the amino acid sequence set forth in SEQ ID NO:45, wherein the modified MNEI protein comprises one or more amino acid replacements wherein the one or more amino acid replacement comprises an amino acid replacement of residue L70 and/or K36.

2. The modified MNEI protein, according to claim 1, wherein the at least two or more amino acid deletions are located within a MNEI loop and beta strand edges, optionally in residues 46-56 of the reference MNEI protein.

3. The modified MNEI protein according to claim 1, wherein the two or more amino acids deletions comprise a deletion of E50, F52 and/or R53 of the reference MNEI protein.

4. The modified MNEI protein, according to claim 1, wherein the at least one food-related property is at least one of sweetness potency, sweetness kinetics, masking effect, enhancing taste and off-taste.

5. The modified MNEI protein, according to claim 1, characterized by at least one of the following compared with the reference MNEI protein: (1) increased thermal stability, (2) improved functional thermal stability, (3) increased pH stability, (4) increased solubility, (5) decreased binding to hydrophobic regions, (6) high pressure stability, and (7) increased shelf-life stability.

6. A food product or a beverage comprising salt and the modified protein according to claim 1.

7. The modified MNEI protein, according to claim 1, wherein L70 is replaced with an aliphatic or beta-branched residue.

8. The modified MNEI protein, according to claim 4, wherein the improved sweetness potency is at least 1.5-fold increased sweetness potency compared with the reference protein.

9. A modified single chain Monellin (MNEI) protein, comprising an amino acid sequence that has two or more amino acids deletions and/or two or more amino acids insertions, to that of a reference MNEI protein, wherein the modified MNEI protein has at least one improved food-related property compared to the reference MNEI protein, and wherein the reference MNEI protein comprises the amino acid sequence set forth in SEQ ID NO:45, wherein the modified MNEI protein comprises an amino acid sequence selected from the group consisting of SEQ ID NO:16, SEQ ID NO:17, SEQ ID NO: 19, SEQ ID NO:20 and SEQ ID NO:21.

10. A product for human consumption comprising the modified MNEI protein according to claim 9, with at least one additional ingredient for human consumption.

11. The product of claim 10, wherein the additional ingredient is at least one selected from (i) *stevia*, sucrose, agave nectar, brown rice syrup, date sugar, honey, maple syrup, molasses, monk fruit, sugar alcohols, rare sugars, aspartame, sucralose, acesulfame potassium, saccharin, neotame, advantame, fructose, glucose, steviol glycosides and dietary fibers, (ii) artificial or natural flavors, food additives, food coloring, preservatives, bulking agents, sugars, and sweetness enhancers or (iii) salt.

12. The product of claim 10, wherein (i) the one or more modified MNEI proteins is in a range of between about 0.2 mg and about 30 mg per 100 gr or 100 ml, and wherein (ii) the product has a pH in the range of between about 2 and about 8.5.

13. The product of claim 10, wherein the product is a beverage or a food product and wherein (i) the beverage is selected from the group consisting of a carbonated soft drink, a non-carbonated soft drink, a fountain beverage, a frozen ready-to-drink beverage, a coffee beverage, a tea beverage, a dairy beverage, a fruit beverage, a flavored water, an enhanced water, a sports drink, an energy drink, an isotonic drink, low-calorie drink, and an alcoholic beverage, (ii) the food product is selected from the group consisting of bakery products, cookies, biscuits, baking mixes, cereals, confectioneries, candies, toffees, chewing gum, bubble gum, dairy products, yogurts, flavored yogurts, peanut butter, soy sauce and other soy base products, nondairy products, salad dressings, ketchup, mayonnaise, vinegar, frozen-desserts, meat products, fish-meat products, bottled and canned foods, tabletop sweeteners, chocolate, fruits, dry fruits, and vegetables.

14. The product of claim 10, wherein the product is (i) reduced sugar or no-sugar added soft drink beverage, (ii) reduced sugar or no-sugar added dairy product, (iii) reduced sugar or no-sugar added sauce product, (iv) reduced sugar or no-sugar added dried fruits, (v) reduced sugar or no-sugar added gum product, (vi) reduced sugar or no-sugar added spread product, (vii) reduced sugar or no-sugar added syrup product, (viii) a food supplementary product, (ix) a medicament, or (x) wherein the product is a flavor modifying agent, a flavor enhancing agent, or a flavor masking agent.

15. A sweetening composition comprising the modified MNEI protein according to claim 9 and at least one further ingredient, wherein the at least one further ingredient comprises at least one of a sweetness enhancer, sweetness blocker and sweetness modifier.

16. A food product or a beverage comprising salt and the sweetening composition of claim 15.

17. The modified MNEI protein, according to claim 9, wherein the at least one food-related property is at least one of sweetness potency, sweetness kinetics, masking effect, enhancing taste and off-taste.

18. The modified MNEI protein, according to claim 17, wherein the improved sweetness potency is at least 1.5-fold increased sweetness potency compared with the reference protein.

19. The modified MNEI protein, according to claim 9, characterized by at least one of the following compared with the reference MNEI protein: (1) increased thermal stability, (2) improved functional thermal stability, (3) increased pH stability, (4) increased solubility, (5) decreased binding to hydrophobic regions, (6) high pressure stability, and (7) increased shelf-life stability.

\* \* \* \* \*